United States Patent [19]

Kluender et al.

[11] 4,220,795
[45] Sep. 2, 1980

[54] CYCLOBUTYL SUBSTITUTED DERIVATIVES OF PROSTAGLANDIN ANALOGS

[75] Inventors: Harold C. Kluender; Henry C. Arndt, both of Madison, Wis.

[73] Assignee: Miles Laboratories, Inc., Elkhart, Ind.

[21] Appl. No.: 933,663

[22] Filed: Aug. 14, 1978

Related U.S. Application Data

[60] Division of Ser. No. 808,279, Jun. 20, 1977, abandoned, which is a continuation-in-part of Ser. No. 693,643, Jun. 6, 1976, abandoned.

[51] Int. Cl.² .............................................. C07L 179/00
[52] U.S. Cl. ............................. 560/118; 260/410.9 R; 260/473; 260/544 L; 424/305; 424/311; 424/317; 424/371; 424/343; 542/426; 560/123; 560/231; 562/500; 562/505; 568/878; 568/833; 568/834; 568/838; 568/839; 556/485; 568/367
[58] Field of Search ......................... 560/118; 562/500

[56] References Cited

U.S. PATENT DOCUMENTS

| 4,028,396 | 6/1977 | Schaub et al. | 560/821 |
| 4,066,834 | 1/1978 | Woessner et al. | 560/121 |
| 4,117,119 | 9/1978 | Kurono et al. | 424/180 |
| 4,152,524 | 5/1979 | Schaub et al. | 560/118 |

*Primary Examiner*—Robert Gesstl
*Attorney, Agent, or Firm*—Jerome L. Jeffers

[57] ABSTRACT

Novel C15 cyclobutyl analogs or derivatives of prostaglandins of the E-, A- and F-classes are useful modifiers of smooth muscle activity. The compounds have valuable pharmacological properties such as platelet antiaggregating agents, gastric antisecretory agents and brochodilating agents.

6 Claims, No Drawings

CYCLOBUTYL SUBSTITUTED DERIVATIVES OF PROSTAGLANDIN ANALOGS

CROSS REFERENCED TO RELATED APPLICATION

This is a division of application Ser. No. 808,279, filed June 20, 1977 which in turn is a continuation-in-part application of Ser. No. 693,643 filed on June 6, 1976, both abandoned.

BACKGROUND OF THE INVENTION

Field of the Invention

Compounds of this invention are analogs of natural prostaglandins.

Natural prostaglandins are twenty-carbon atom alicyclic compounds related to prostanoic acid which has the following structure:

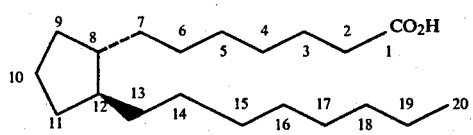
(I)

By convention, the carbon atoms of I are numbered sequentially from the carboxylic carbon atom. An important stereochemical feature of I is the trans-orientation of the sidechains $C_1$-$C_7$ and $C_{13}$-$C_{20}$. All natural prostaglandins have this orientation. In I, as elsewhere in this specification, a dashed line (---) indicates projection of a covalent bond below the plane of a reference carbon atom (alpha-configuration), while a wedged line (◂■) represents direction above that plane (beta-configuration). Those conventions apply to all compounds subsequently discussed in this specification.

In one system of nomenclature suggested by N. A. Nelson (J. Med. Chem., 17: 911 (1974), prostaglandins are named as derivatives or modifications of the natural prostaglandins. In a second system, the I.U.P.A.C. (International Union of Pure and Applied Chemistry) system of nomenclature, prostaglandins are named as substituted heptanoic acids. Yet a third system of nomenclature is frequently used by those skilled in the prostaglandin art. In this third system (also described by Nelson), all prostaglandins are named as derivatives or modifications of prostanoic acid (structure I) or prostane (the hydrocarbon equivalent of structure I). This system is used by Chemical Abstracts and may become an I.U.P.A.C. accepted system.

Natural prostaglandins have the structures,

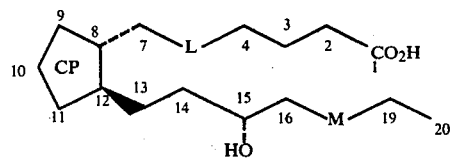
(II)

in which: L and M may be ethylene or cis-vinylene radicals and the five-membered ring

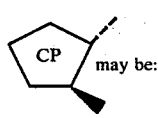 may be:

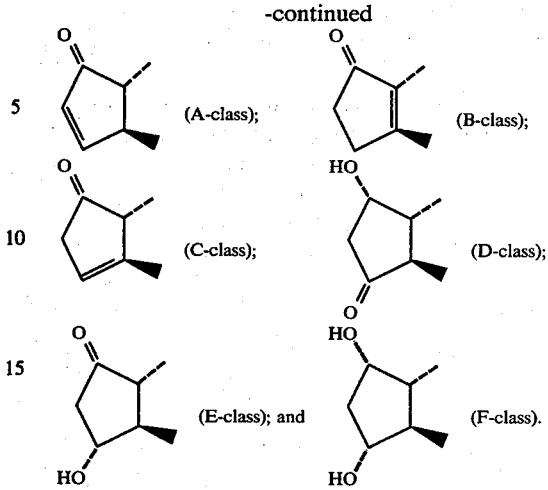

Prostaglandins are classified according to the functional groups present in the fivemembered ring and the presence of double bonds in the ring or chains. Prostaglandins of the A-class (PGA or prostaglandin A) are characterized by an oxo group at $C_9$ and a double bond at $C_{10}$-$C_{11}$ ($\Delta^{10,11}$); those of the B-class (PGB) have an oxo group at $C_9$ and a double bond at $C_8$-$C_{12}$ ($\Delta^{8,12}$); compounds of the C-class (PGC) contain an oxo group at $C_9$ and a double bond at $C_{11}$-$C_{12}$ ($\Delta^{11,12}$); members of the D-class (PGD) have an oxo group at $C_{11}$ and an alpha-oriented hydroxy group at $C_9$; prostaglandins of the E-class (PGE) have an oxo group at $C_9$ and an alpha-oriented hydroxyl group at $C_{11}$; and members of the F-class (PGF) have an alpha-directed hydroxyl group at $C_9$ and an alpha-oriented hydroxyl group at $C_{11}$. Within each of the A-, B-, C-, D-, E-, and F-classes of prostaglandins are three subclassifications based upon the presence of double bonds in the side-chains at $C_5$-$C_6$, $C_{13}$-$C_{14}$, or $C_{17}$-$C_{18}$. The presence of a trans-unsaturated bond only at $C_{13}$-$C_{14}$ is indicated by the subscript numeral 1; thus, for example, $PGE_1$ (or prostaglandin $E_1$) denotes a prostaglandin of the E-type (oxo group at $C_9$ and an alpha-hydroxyl at $C_{11}$) with a trans-double bond at $C_{13}$-$C_{14}$. The presence of both a trans-double bond at $C_{13}$-$C_{14}$ and a cis-double bond at $C_5$-$C_6$ is denoted by the subscript numeral 2; for example, $PGE_2$. Lastly, a trans-double bond at $C_{13}$-$C_{14}$, a cis-double bond at $C_5$-$C_6$ and a cis-double bond at $C_{17}$-$C_{18}$ is indicated by the subscript numeral 3; for example, $PGE_3$. The above notations apply to prostaglandins of the A-, B-, C-, D-, and F-series as well, however, in the latter the alpha-orientation of the hydroxyl group at $C_9$ is indicated by the subscript Greek letter $\alpha$ after the numerical subscript.

The three systems of nomenclature as they apply to natural $PGF_{3\alpha}$ are shown below:

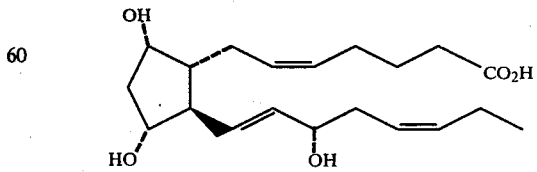

Nelson System:
  Prostaglandin $F_{3\alpha}$ or $PGF_{3\alpha}$ (shortened form)
I.U.P.A.C. System:

7-[3R,5S-Dihydroxy-2S-(3S-hydroxy-1E,5Z-octadienyl)-cyclopent-1R-yl]-5Z-heptenoic acid Third System (Chemical Abstracts):

(5Z, 9α, 11α, 13E, 15S, 17Z)-9,11,15-trihydroxyprosta-5,13,17-trien-1-oic acid.

It is important to note that in all natural prostaglandins there is an alpha-oriented hydroxyl group at $C_{15}$. In the Cahn-Ingold-Prelog system of defining stereochemistry, that $C_{15}$ hydroxyl group is in the S-configuration. The Cahn-Ingold-Prelog system is used to define stereochemistry of any asymmetric center outside of the carbocyclic ring in all three systems of nomenclature described above. This is in contrast to some prostaglandin literature in which the α,β designations are used, even at $C_{15}$.

11-Deoxy derivatives of PGE and PGF molecules do not occur as such in nature, but constitute a class of compounds which possess biological activity related to the parent compounds. Formula II represents 11-deoxy PGE and PGF compounds when:

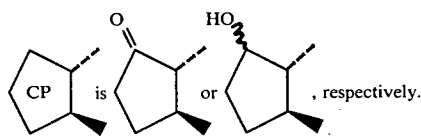
, respectively.

In this formula, and others of this patent specification a swung dash or serpentine line (∼) denotes a covalent bond which can be either in the alpha configuration (projecting below the plane of a reference carbon atom) or in the beta configuration (projecting above the plane of a reference carbon atom).

PGF$_\beta$ molecules also do not occur as such in nature, but constitute a class of compounds which possess biological activity related to the parent comounds. Formula II represents PGF$_\beta$ compounds when:

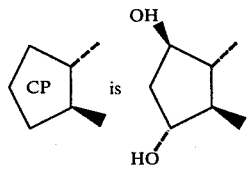

9-Deoxy derivatives of PGE do not occur as such in nature, but constitute a class of compounds which possess biological activity related to the parent compounds. Formula II represents 9-deoxy PGE compounds when:

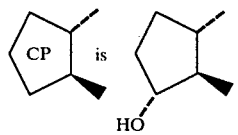

9-Deoxy-Δ$^{9,10}$ derivatives of PGE do not occur as such in nature, but constitute a class of compounds which possess biological activity related to the parent compounds. Formula II represent 9deoxy-Δ$^{9,10}$ PGE compounds when:

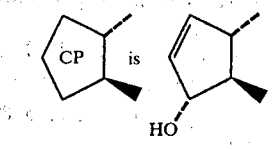

9a-Homo- and 9a-homo-11-deoxy-derivative of PGE and PGF molecules do not occur as such in nature, but constitute a class of compounds which possess biological activity related to the parent compounds. Formula II represents 9a-homo- and 9a-homo-11-deoxy-compounds of PGE and PGF when:

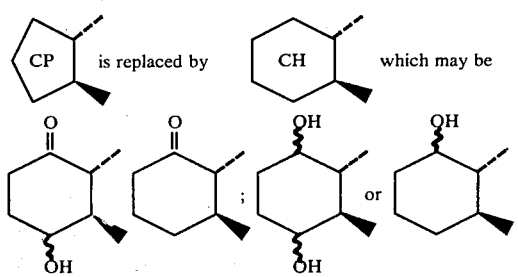

11a-Homo- derivatives of PGE, PGF and PGA molecules do not occur as such in nature, but constitute classes of compounds which are expected to posses biological activity related to the parent compounds. Formula II represents 11a-homo- derivatives of PGE, PGF and PGA molecules when:

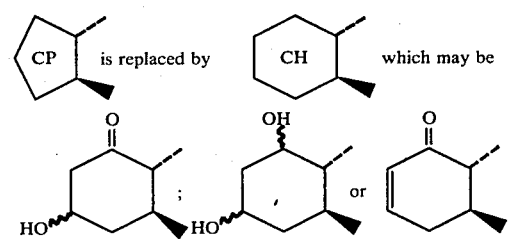

11-Epi-PGE and PGF molecules do not occur as such in nature, but constitute classes of compounds which possess biological activity related to the parent compounds. Formula II represents 11-epi-compounds of PGE and PGF when:

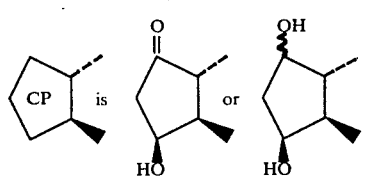

8iso-, 12iso or 8,12-bis iso (ent) prostaglandins do not occur as such in nature, but constitute classes of compounds which possess biological activity related to the parent compounds. Formula II represents 8iso-, 12iso- or 8,12-bis iso (ent) compounds when:

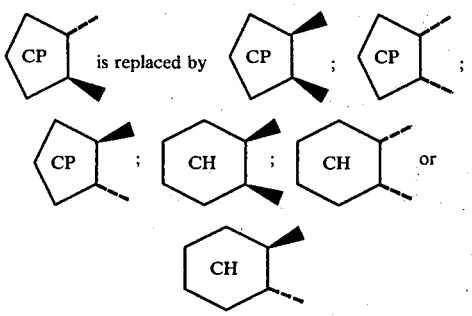

These iso modifications of Formula II may be divided into all of the sub-classes with varying ring oxygenation as described above.

Recent research indicates that prostaglandins are ubiquitous in animal tissues and that prostaglandins, as well as their synthetic analogs, have important biochemical and physiological effects in mammalian endocrine, reproductive, central and peripheral nervous, sensory, gastrointestinal, hematic, respiratory, cardiovascular, and renal systems.

In mammalian endocrine systems, experimental evidence indicates prostaglandins are involved in the control of hormone synthesis or release in hormone-secretory glands. In rats, for example, $PGE_1$ and $PGE_2$ increase release of growth hormone while $PGA_1$ increased synthesis of that hormone. In sheep, $PGE_1$ and $PGF_{1\alpha}$ inhibit ovarian progesterone secretion. In a variety of mammals, $PGF_{1\alpha}$ and $PGF_{2\alpha}$ act as luteolytic factors. In mice, $PGE_1$, $PGE_2$, $PGF_{1\alpha}$ and $PGF_{1\beta}$ increase thyroid activity. In hypophysectomized rats, $PGE_1$, $PGE_2$ and $PGF_{1\alpha}$ stimulate steroidogenesis in the adrenal glands.

In the mammalian male reproductive system, $PGE_1$ contracts the smooth muscle of the vas deferens. In the female reproductive system, PGE and $PGF_\alpha$ compounds contract uterine smooth muscle. In general, PGE, PGB and PGA compounds relax in vitro human uterine nuscle strips, whle those of the $PGF_\alpha$ class contract such isolated preparations. PGE compounds in general promote fertility in the female reproductive system while $PGF_{2\alpha}$ has contragestational effects. $PGF_{2\alpha}$ also appears to be involved in the mechanism of menstruation. In general, $PGF_2$ exerts potent oxytocic effects in inducing labor, while $PGF_{2\alpha}$ induces spontaneous abortions in early pregnancy $PGF_\alpha$ and PGE compounds have been isolated from a variety of nervous tissue and they seem to act as neurotransmitters. $PGE_1$ retards whereas $PGF_{2\alpha}$ facilitates transmission in motor pathways in the central nervous system. It has been reported that $PGE_1$ and $PGE_2$ inhibit transmitter release from adrenergic nerve endings in the guinea pig.

Prostaglandins stimulate contraction of gastrointestinal smooth muscle to vivo and in vitro. In dogs, $PGA_1$, $PGE_1$ and $PGE_2$ inhibit gastric secretion. $PGA_1$ exhibits similar activity in man.

In most mammalian respiratory tracts, compounds of the PGE and PGF class relax in vitro preparations of tracheal smooth muscle. In that preparation, $PGE_1$ and $PGE_2$ relax while $PGF_{2\alpha}$ contracts the smooth muscle. PGE and PGF compounds are normally found in the human lung, and it is postulated that some cases of bronchial asthma involve an imbalance in the production or metabolism of those compounds.

Prostaglandins are involved in certain hematic mechanisms in mammals, $PGE_1$, for example, inhibits thrombogenesis in vitro through its effects on blood platelets.

In a variety of mammalian cardiovascular systems, compounds of the PGE and PGA class are vasodilators whereas those of the $PGF_\alpha$ class vasoconstrictors, by virtue of their action on vascular smooth muscle.

Prostaglandins are naturally found in the kidney and reverse experimental and clinical renoprival hypertension.

The clinical implications of prostaglandins and their analogs are far-ranging and include, but are not limited to the following: in obstetrics and gynecology, they may be useful in fertility control, treatment of menstrual disorders, induction of labor, and correction of hormone disorders; in gastroenterology, they may be useful in the treatment of peptic ulcers and various disorders involving motility, secretion, and absorption in the gastrointestinal tract; in the respiratory area, they may be beneficial in therapy of bronchial asthma and other diseases involving bronchoconstriction; in hematology, they may have utility as anticlotting agents in diseases such as venous thrombosis, thrombotic coronary occlusion and other diseases involving thrombi; in circulatory diseases they have therapeutic utility in hypertension, peripheral vasopathies, and cardiac disorders.

For a more complete review of chemical, physiological and pharmacological aspects of the prostaglandin, consult the following references: The Prostaglandins, Vol. I., P. Ramwell, Ed., New York, Plenum Press, 1973; Ann. N.Y. Acad. Sci., 180: 1–568 (1971): and Higgins and Braunwald, J. Am. Med. Assn., 53: 92–112 (1972).

DESCRIPTION OF THE PRIOR ART

South African Patent No. 7,308,595 discloses 15-substituted-ω-pentanorprostaglandins, wherein the substituent is a cycloalkyl of from three to ten carbon atoms, 1-adamantyl, 2-norbornyl or 2-indanyl and possesses increased tissue specificity of action over the parent prostaglandins. Especially preferred are the 16-(1-adamantyl)-ω-tetranorprostaglandins and the 16-(cyclohexyl)-υ-tetranorprostaglandins of the $PGE_2$ and the $PGF_{2\alpha}$ classes.

U.S. Pat. No. 3,884,969 discloses selected 15-substituted-11-deoxy-$PGE_1$ and $PGE_2$ acids and esters, wherein the substituent is a cycloalkyl having from 3 to 9 carbon atoms, cycloalkenyl having from 5 to 9 carbon atoms, mono or di-lower alkyl substituted cycloalkenyl groups having from 5 to 9 carbon atoms in the ring and adamantyl groups.

German Patent No. 2,510,818, laid open Sept. 18, 1975, discloses 15-cyclobutyl-prostaglandin acids and esters as having selective gastric acid secretory and bronchodilatory effects.

U.S. Pat. No. 3,867,375 discloses various reagents for preparing and method of preparing natural prostaglandins.

SUMMARY

Novel and useful 15-cyclobutyl analogs of prostaglandin primary alcohols having the following structural Formula III are included in the subject matter of this invention:

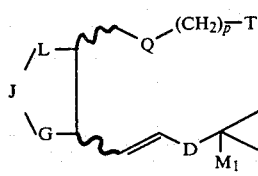

(III)

In Formula III:
- D is a R-hydroxymethylene, S-hydroxymethylene or acetoxymethylene radical;
- G is a methylene, α-hydroxymethylene, β-hydroxymethylene or methine radical such that G is methine only when J is methine;
- J is a methylene, ethylene or methine radical such that J is ethylene only when G is methylene and J is methine only when G is methine to form a carbon-carbon double covalent bond between G and J;
- L is carbonyl, α-hydroxymethylene or β-hydroxymethylene radical;
- Q is ethylene or Z-vinylene radical;
- p is an integer having a value of from 1 to 4, preferably a value of 2 or 3;
- T is a hydroxymethyl or acetoxymethylene radical;
- $M_1$ is hydrogen or lower alkyl having from 1 to 5 carbon atoms;
- $M_2$ is hydrogen or -(CH$_2$)$_{\overline{n}}$M$_4$ where n is zero or an integer having a value of from 1 to 5 and where $M_4$ is hydrogen or cycloalkyl having from 3 to 12 carbon atoms; and
- $M_3$ is hydrogen or lower alkyl having 1 to 3 carbon atoms.

The numbering system and stereochemistry nomenclature used for the prostaglandins of this invention are according to the Chemical Abstracts system which employs prostane or prostanoic acid as the stereoparent compound. In Formula III, a dashed line (--) indicates projection of a covalent bond below the plane of a reference carbon atom (alpha configuration); a wedged line (▶) represents direction above that plane (beta configuration) and a swung dash or serpentine line (~) denotes a covalent bond which can be either the alpha or beta configuration. As used herein cis or trans isomerism around double bonds respectively is designated by affixes Z (zusammen) and E (entgegen). Chirality around asymmetric carbon atoms in the carbocyclic ring is designated by affixes α (alpha) and β (beta). Chirality around asymmetric carbon atoms in the alkyl side chains is designated by affixes R (rectus) and S (sinister) according to the Cahn-Ingold-Prelog system of defining stereochemistry.

Analogs or derivatives of the E-, A- and F-classes of the natural prostaglandin primary alcohols are represented by Formula III. Thus, when L is carbonyl, J is methylene or ethylene and G is methylene or hydroxymethylene such that J is ethylene only when G is methylene and T, p, Q, D, $M_1$, $M_2$ and $M_3$ are as defined above, III represents analogs of the E-class, 11-deoxy-E-class or 9α-homo-11-deoxy-E-class ($E_1$ when Q is ethylene and $E_2$ when Q is Z-vinylene) of prostaglandins:

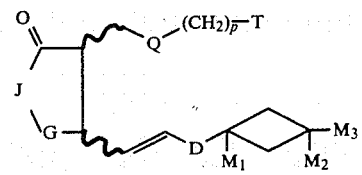

(IIIa)

When L is carbonyl, J is methylene and G is α-hydroxymethylene or β-hydroxymethylene and T is as defined above, III represents analogs of the E-class of prostaglandins:

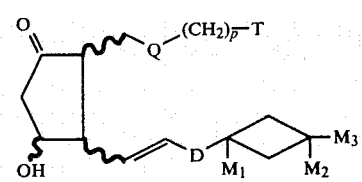

(IIIb)

When L is carbonyl and both J and G are methylene and T is as defined above, III represents analogs of the 11-deoxy-E-class of prostaglandins:

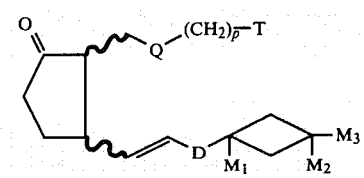

(IIIc)

When L is carbonyl, J is ethylene, G is methylene and T is as defined above, III represents analogs of 9α-homo-II-deoxy-prostaglandin $E_2$:

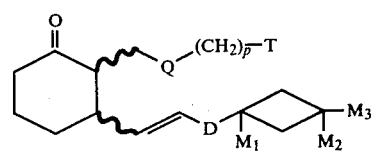

(IIId)

When L is carbonyl and both J and G are methine radicals, III represents analogs of the A-class ($A_1$ when Q is ethylene and $A_2$ when Q is Z-vinylene) of prostaglandins:

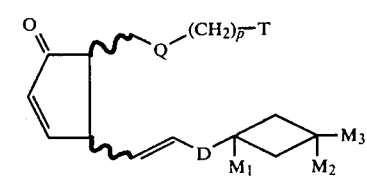

(IIIe)

When L is α-hydroxymethylene or β-hydroxymethylene; J is methylene or ethylene; G is α-hydroxymethylene, β-hydroxymethylene or methylene such that J is ethylene only when G is methylene, III represents analogs of PGF$_\alpha$, PGF$_\beta$, 11-deoxy-PGF$_\alpha$, 11-deoxy-PGF$_\beta$, 9a-homo-11-deoxy PGF$_\alpha$ and 9a-homo-11-deoxy-PGF$_\beta$ (F$_1$ when Q is ethylene and F$_2$ when Q is Z-vinylene);

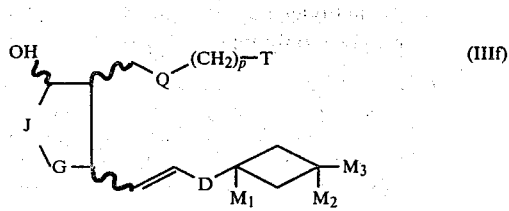

When L is α-hydroxymethylene or β-hydroxymethylene; J is methylene; and G is α-hydroxymethylene, III represents analogs of PGF$_\alpha$ and PGF$_\beta$:

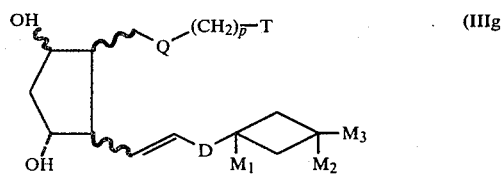

Also included in the subject matter of this invention are the novel and useful C-15-cyclobutyl analogs of prostaglandins acids and esters of structural Formula III.

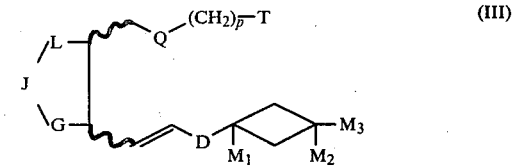

In Formula III:
D is a R-hydroxymethylene, S-hydroxymethylene or acetoxymethylene radical;
G is an α-hydroxymethylene, β-hydroxymethylene or methine radical such that G is methine only when J is methine;
J is a methylene or methine radical such that J is methine only when G is methine to form a carbon-carbon double covalent bond between G and J;
L is carbonyl, α-hydroxymethylene or β-hydroxymethylene radical;
Q is ethylene or Z-vinylene radical;
p is an integer having a value of 2 or 3;
T is an alkoxycarbonyl having from 1 to 3 carbon atoms inclusive in the alkyl chain, carboxyl or pharmacologically acceptable nontoxic carboxy salts thereof;
M$_1$ is hydrogen or lower alkyl having from 1 to 5 carbon atoms;
M$_2$ is hydrogen or -(CH$_2$)$_{\overline{n}}$M$_4$ where n is 0 or an integer having a value of from 1 to 5 and where M$_4$ is hydrogen or cycloalkyl having from 3 to 12 carbon atoms, provided that M$_1$ and M$_2$ are not both hydrogen at the same time and M$_4$ is not hydrogen when n=0; and
M$_3$ is hydrogen or lower alkyl having from 1 to 5 carbon atoms.

Analogs or derivatives of the E-, A- and F-classes of the natural prostaglandin acids and esters are represented by the above Formula III. Thus when L is carbonyl, J is methylene and G is α-hydroxymethylene or β-hydroxymethylene and T is an alkoxycarbonyl, carboxyl or salts thereof, III represents analogs of the E-class (E$_1$ when Q is ethylene and E$_2$ when Q is Z-vinylene) of prostaglandin acids and esters:

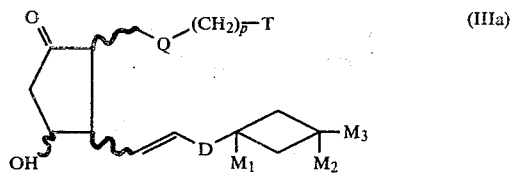

When L is carbonyl and both J and G are methine radicals, III represents analogs of the A-class (A$_1$ when Q is ethylene and A$_2$ when Q is Z-vinylene) of prostaglandin acids and esters:

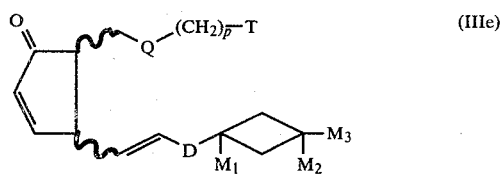

When L is α-hydroxymethylene or β-hydroxymethylene; J is methylene; and G is α-hydroxymethylene, III represents analogs of PGF$_\alpha$ and PGF$_\beta$ (F$_1$ when Q is ethylene and F$_2$ when Q is Z-vinylene):

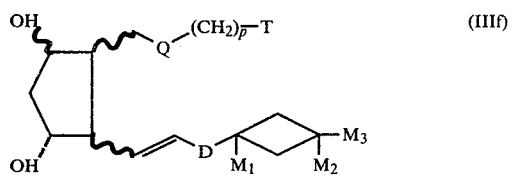

Useful intermediates in the preparation of compounds of Formula III are represented by the formula:

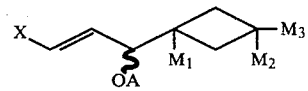

In Formula IV;
X is an iodo or bromo radical;
A is an acid-labile hydroxyl-protecting group selected from the class consisting of 1-ethoxyethyl; trimethylsilyl; tert-butyl-dimethylsilyl; 2-ethoxyprop-2-yl; tetrahydropyran-2-yl or triphenylmethyl radicals;
M$_1$ is hydrogen or lower alkyl having from 1 to 5 carbon atoms;
M$_2$ is hydrogen, lower alkyl having from 1 to 3 carbon atoms, or -(CH$_2$)$_{\overline{n}}$M$_4$ where n is 0 or an integer having a value of from 1 to 5 and where M$_4$ is hydrogen or cycloalkyl having from 3 to 12 carbon atoms, provided that M$_1$ and M$_2$ are not both hydrogen at the same time; and
M$_3$ is hydrogen or lower alkyl having from 1 to 5 carbon atoms.

A useful process, included in this invention, for preparing compounds of the formula

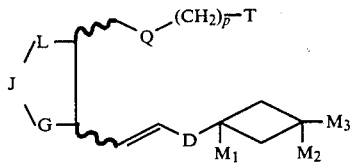

is disclosed wherein:
D is a R-hydroxymethylene or S-hydroxymethylene or acetoxy-methylene radical;
G is a methylene, α-hydroxymethylene, β-hydroxymethylene or methine radical such that G is methine only when J is methine;
J is a methylene, ethylene or methine radical such that J is ethylene only when G is methylene and J is methine only when G is methine to form a carbon-carbon double bond between G and J;
L is a carbonyl, α-hydroxymethylene or β-hydroxymethylene radical;
Q is an ethylene or Z-vinylene radical;
p is an integer having a value of 1 to 4 inclusive;
T is a hydroxymethyl or acetoxymethylene radical;
$M_1$ is hydrogen or lower alkyl having from 1 to 5 carbon atoms;
$M_2$ is hydrogen or $-(CH_2)_n M_4$ where n is zero or an integer having a value of from 1 to 5 and $M_4$ is a cycloalkyl having from 3 to 12 carbon atoms; and
$M_3$ is hydrogen or lower alkyl having from 1 to 3 carbon atoms; which comprises contacting a compound of the formula:

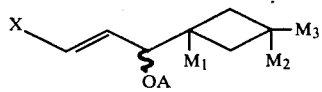

wherein:
X is an iodo- or bromo-radical;
A is an acid-labile hydroxyl-protecting group selected from the class consisting of 1-ethoxyethylene, trimethylsilyl, tert-butyldimethylsilyl, 2-ethoxyprop-2-yl, tetrahydropyran-2-yl or triphenylmethyl radicals; and the substituent $M_1$, $M_2$ and $M_3$ are as hereinabove defined, with a reagent selected from the class consisting of metallic lithium, lower alkyl lithium, magnesium or lower alkyl magnesium in an inert solvent under an inert atmosphere; contacting the reaction mixture with a solvent soluble copper(I) complex such as copper(I) pentyne, tri-n-butylphosphine-copper(I) iodide, hexamethylphosphorus triamide-copper(I) iodide or copper(I) thiophenolate; and contacting the resultant reaction mixture with a compound of the formula:

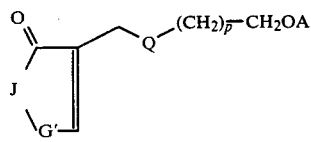

wherein:
G' is methylene, α- or β-hydroxymethylene radical protected with an acid-labile-protecting group A;

J is a methylene or ethylene radical such that J is ethylene only when G' is methylene; and
Q, p and A are as defined above;
in an inert solvent for a period of time sufficient for a substantial degree of conjugate 1,4 addition to take place to form an acid-labile hydroxyl-protected intermediate compound, hydrolyzing the so-formed intermediate compound and recovering the so-formed compounds having Formula III from the reaction mixture.

Another useful process, included in this invention, for preparing compounds of the formula:

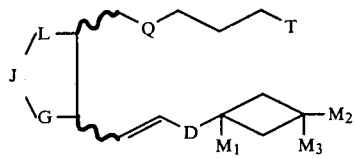

is disclosed wherein:
D is a R-hydroxymethylene, S-hydroxymethylene or acetoxymethylene radical;
G is an α-hydroxymethylene, β-hydroxymethylene or methine radical such that G is methine only when J is methine;
J is a methylene or methine radical such that J is methine only when G is methine to form a carbon-carbon double bond between G and J;
L is a carbonyl, α-hydroxymethylene or β-hydroxymethylene radical;
Q is an ethylene or Z-vinylene radical;
T is an alkoxycarbonyl having from 1 to 3 carbon atoms inclusive in the alkyl chain, carboxyl or pharmacologically acceptable nontoxic carboxy salts thereof;
$M_1$ is hydrogen or lower alkyl having from 1 to 5 carbon atoms;
$M_2$ is hydrogen or $-(CH_2)_n M_4$ where n is 0 or an integer having a value of from 1 to 5 and where $M_4$ is hydrogen or cycloalkyl having from 3 to 12 carbon atoms, provided that $M_1$ and $M_2$ are not both hydrogen at the same time; and
$M_3$ is hydrogen or lower alkyl of 1 to 5 carbon atoms; which comprises contacting a compound of the formula:

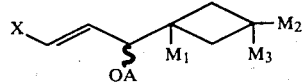

wherein:
X is an iodo- or bromo-radical;
A is an acid-labile hydroxyl-protecting group selected from the class consisting of 1-ethoxyethylene, trimethylsilyl, tert-butyldimethylsilyl, 2-ethoxyprop-2-yl, tetrahydropyran-2-yl, or triphenylmethyl radical; and
the substituents $M_1$, $M_2$ and $M_3$ are as defined above, with a reagent selected from the glass consisting of metallic lithium, lower alkyl lithium metallic magnesium or lower alkyl magnesium, in an inert solvent under an inert atmosphere; contacting the reaction mixture with a solvent soluble copper(I) complex such as copper(I) pentyne, tri-n-butylphosphine-copper(I) iodide, hexamethylphosphorus triamidecopper(I) iodide or copper(I) thiophendate; and contacting the resultant reaction mixture with a compound of the formula:

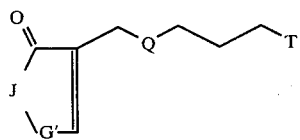

wherein:

G' is methylene, α- or β-hydroxymethylene radical protected with an acid-labile protecting group-A;

J is a methylene or ethylene radical such that J is ethylene only when G' is methylene;

T is an alkoxycarbonyl having from 1 to 3 carbon atoms inclusive in the alkyl chain; and Q is as defined above; in an inert solvent for a period of time sufficient for substantial degree of conjugate 1,4 addition to take place to form an acid-labile hydroxyl-protected intermediate compound, hydrolyzing the so-formed intermediate compound and recovering the so-formed coumpounds having Formula III from the reaction mixture.

DESCRIPTION OF THE INVENTION

Compounds having Formula III are prepared via the 1,4-conjugate addition of organocopper reagents to cyclopentenones as reported by Sih, et. al. (J. Amer. Chem. Soc., 97: 857, 865 [1975], and references cited therein). The novel compounds of Formula III are prepared according to the reaction sequence depicted in Table A.

TABLE A

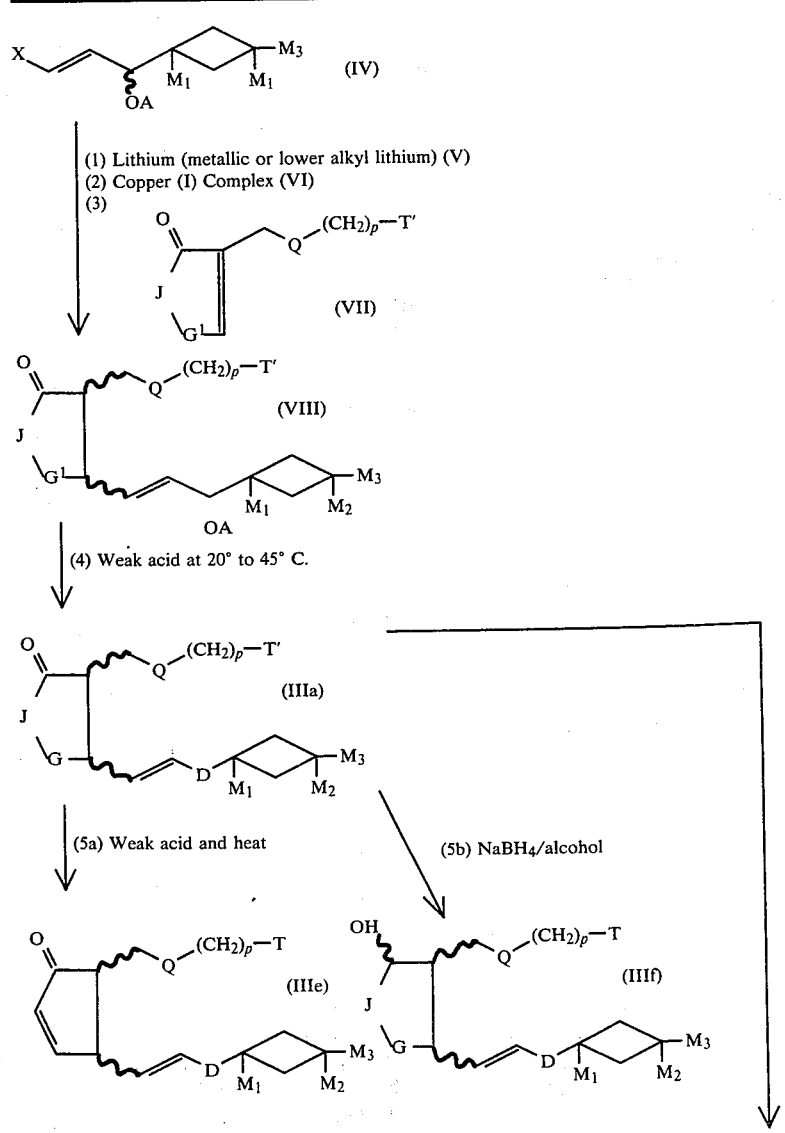

TABLE A-continued

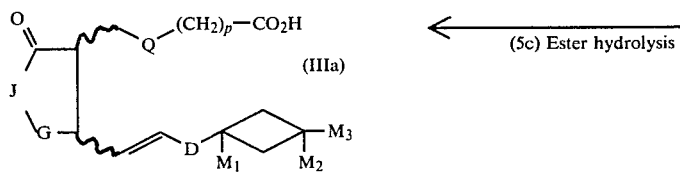

(5c) Ester hydrolysis

In Table A, Compound IV, where X is an iodo or bromo radical and A is an acid-labile hydroxyl-protecting group, is contacted and reacted with metallic lithium or a lower alkyl lithium (Compound V) at from about −80° to 0° C. for about 0.25 to 3.0 hr in an inert solvent, such as ether, tetrahydrofuran, hexane, pentane, toluene, mixtures thereof and the like, under an inert atmosphere, such as argon, nitrogen and the like. Copper(I) complex (Compound VI) is added, usually as a solution in an inert solvent, to the reaction mixture and the mixture is then stirred at less than about −20° C. for about 0.25 to 1.0 hr. A solution of Compound VII, where G' is methylene or =CHOA and T' is —$CH_2OA$ or alkoxycarbonyl, usually in an inert solvent, is added to the reaction mixture which is then allowed to warm to about −20° to 25° C. over a 0.5 to 5 hr period to yield the intermediate Compound VIII after quenching with a proton donor. Treatment of the latter compound under hydrolysis conditions such as with a weakly-acidic water mixture, such as acetic acid-water (65:35 V/V) with 10% tetrahydrofuran, under an inert atmosphere at a temperature of about 20° to 45° C. for about 0.5 to 48 hr cleaves the acid-labile hydroxyl-protecting groups (described in *J. Amer. Chem. Soc.;* 94:6194 [1972]) to yield Compound IIIa.

Where G and J of Compound IIIa are respectively hydroxymethylene and methylene, dehydration of Compound IIIa with a weakly-acidic water mixture, such as acetic acid-water, at about 60° to 80° C. (described in *J. Org. Chem.;* 34:3553 [1969]) yields Compound IIIe. Compound IIIe is also obtained as a by-product of the acidic hydrolysis of Compound VIII.

Reduction of Compound IIIa with sodium borohydride in an inert alcoholic or other suitable polar solvent (described in *J. Org. Chem.;* 34:3552 [1969]) yields Compound IIIf.

When T and G of Compound IIIa are respectively alkoxycarbonyl and methylene, and when T of Compound IIIf is alkoxycarbonyl, cleavage of the ester group with a base, such as sodium hydroxide or potassium hydroxide in a mixed organic solvent such as water-tetrahydrofuran, water-p-dioxane or water-alcohol (described in *J. Amer. Chem. Soc.,* 94:7823 [1973]) yields the corresponding acid, i.e. where T is carboxyl. Where G and T of Compound IIIa are respectively hydroxymethylene and alkoxycarbonyl, cleavage of the ester group by exposure to Rhizopus oryzae (described in *J. Amer. Chem. Soc.;* 95:1676 [1973]) or with a suitable esterase or lipase (described in U.S. Pat. No. 3,769,166 and German Patent application No. 2,242,792) yields the corresponding acid, i.e. where T is carboxyl.

Treatment of Compounds IIIa or IIIe where T is carboxyl or alkoxycarbonyl group, with a suitable carbonyl protecting group followed by reduction and treatment with nitrous acid yields the corresponding primary alcohol, i.e. where T is hydroxymethyl (described in U.S. Pat. No. 3,636,120). Suitable carbonyl protecting groups include lower alkoxyamines, semicarbazide or thiosemicarbazides. Suitable reducing agents include lithium aluminum hydride, lithium borohydride, and diisobutyl aluminum hydride.

Non-toxic, pharmacologically acceptable salts of Compound III can be prepared by neutralization of III, where T is carboxyl, with an equivalent or an excess amount of the corresponding non-toxic salt-forming organic or inorganic base. The salts are prepared by procedures which are well-known in the art. Suitable salts include sodium, potassium, ammonium and the like. The salts may be isolated by lyophilization of the resulting mixture, or by filtration if sufficiently insoluble, or by similar well-known techniques.

All compounds of this invention can be isolated from reaction mixtures and purified by well-known organic chemistry procedures. For example, the compounds can be isolated by dilution of the reaction mixture with water, extraction with a water-immiscible solvent such as benzene, cyclohexane, ether, ethyl acetate, methylene chloride, toluene and the like; chromatography; distillation or a combination of these procedures. Purification of these compounds can be accomplished by the methods which are well-known in the art for the purification of prostaglandins, lipids, fatty acids, and fatty esters. For example, such methods as reverse phase partition chromatography; counter-current distribution; adsorption chromatography on acid washed magnesium silicate, neutral or acid washed silica gel, alumina or silicic acid; preparative paper chromatography; preparative thin layer chromatography; high pressure liquid-liquid chromatography; gas-liquid chromatography; and combinations thereof can be used to purify the compounds produced by the processes of this invention.

The starting reactants used in the above procedures are well-known or easily prepared by known methods. For instance, in the reaction sequence depicted in Table A, Compound V, i.e. metallic lithium or lower alkyl lithium such as t-butyllithium, sec-butyllithium or n-butyllithium are commercially available or prepared by well-known organic chemistry methods. Examples of Compound VI, i.e. copper(I) complexes, include: [hexamethylphosphorous triamide]$_2$ copper(I) pentyne (preparation described in *J. Amer. Chem. Soc.;* 94:7210 [1972]); and *J. Org. Chem.;* 31:4071 [1966]); tri-n-butylphosphine-copper(I) iodide (preparation described in *Inor. Synth.;* 7:9 [1963]); hexamethylphosphorus triamidecopper(I) iodide (preparation described in Prostaglandins; 7:387 [1974]); copper(I) thiophenolate (preparation described in Synthesis, 662 [1974]) and the like. Examples of Compound VII which are employed in the synthesis of III, where T is hydroxymethyl or acetoxymethylene radical, include: 1-(tetrahydropyran-2-yloxy)-7-(5-oxocyclopent-1-enyl) heptane (preparation described in *Tet. Let.,* 24:2435 [1972]); 1-(tetrahydropyran-2-yloxy)-7-(5-oxocyclopent-1-enyl) hept-5Z-ene; 1-(tetrahydropyran-2-yloxy)-6-(5-oxocyclopent-1-enyl) hexane; 1-(tetrahydropyran-2-yloxy)-6-(5-oxocyclopent-1-enyl) hex-4Z-ene; 1-(tetrahydropyan-2-yloxy)-7-[3R-(tetrahydropyran-2-yloxy)-5-oxocyclopent-1-enyl] heptane; 1-(tetrahydorpyran-2-yloxy)-7-[3R-tetrahydropyran-2-yloxy)-5-oxocyclopent-1-enyl] hept-5Z-ene; 1-(tetrahydropyran-2-yloxy)-6-[3R-tetrahydropyran-2-yloxy)-5-oxocyclopent-1-enyl] hexane; 1-tetrahydropyran-2-yloxy)-6-[3R-tetrahydropyran-2-yloxy)-5-oxocyclopent-1-enyl] hex-4Z-ene; 1-(tetrahydropyran-2-yloxy)-7-(6-oxocyclohex-1-enyl) heptane; 1-(tetrahydropyran-2-yloxy)-7-(6-oxocyclohex-1-enyl) hept-5Z-ene; 1-(tetrahydropyran-2-yloxy)-6-(6-oxocyclohex-1-enyl) hexane; and 1-(tetrahydropyran-2-yloxy)-6-(6-oxocyclohex-1-enyl) hex-4Z-ene.

Examples of Compound VII which are employed in the synthesis of III, where T is alkoxycrbonyl, carboxyl or salts thereof, include methyl 7-[3R-(tetrahydropyran-2-yloxy)-5-oxocyclopent-1-enyl] heptanoate (preparation described in *J. Amer. Chem. Soc.;* 95:1676 [1973]); methyl 7-(6-oxocyclohex-1-enyl)hept-5Z-enoate; methyl 7-[3R-(tetrahydropyran-2-yloxy)-5-oxocyclopent-1-enyl] hept-5Z-enoate (preparation described in *Tet. Let.,* 2313 [1973]); methyl 7-[3S-(tetrahydropyran-2-yloxy)-5-oxocyclopent-1-enyl] heptanoate (preparation described in *J. Amer. Chem. Soc.;* 97:865 [1975]); and methyl 7-[3S-(tetrahydropyran-2-yloxy)-5-oxocyclopent-1-enyl] hept-5Z-enoate (preparation described in *J. Amer. Chem. Soc.;* 97:865 [1975]).

The examples of Compound VII disclosed above which are employed in the synthesis of III where T is a hydroxymethyl or acetoxymethylene radical, can be prepared from well-known materials by various methods including the following:

wherein G is a methylene, α- or β-hydroxymethylene radical; J is a methylene or ethylene radical such that J is ethylene only when G is methylene; $T_2$ is an alkoxycarbonyl having from 1 to 3 carbon atoms inclusive in the alkoxy chain; A is an acid-labile hydroxyl-protecting group; G' is methylene, α- or β-hydroxymethylene radical protected with an acid-labile hydroxyl-protecting group-A; and Q and p are as defined above. In IX→X, Compound IX is reacted with hydroxylamine to form the corresponding oxime-protected carbonyl, Compound X, using conditions which are well-known in the art (see U.S. Pat. No. 3,636,120 and Australian Patent No. 5,108,173). In X→XI, Compound X is reacted with a suitable reducing agent such as lithium aluminum hydride, or the like, at a temperature below about 30° C. to reduce the ester or carboxyl group at T to the corresponding alcohol, Compound XI (where T is hydroxymethyl). In XI→XII, Compound XI is reacted with nitrous acid at a temperature of about −10° to about 50° C. to remove the oxime protecting group and to regenerate the carbonyl. The nitrous acid is formed by adding an aqueous solution of an alkali metal or alkaline earth metal nitrite, such as sodium nitrite, to a liquid alkonoic acid such as acetic or propionic acid. In XII→VII, Compound XII is reacted with a suitable acid-labile hydroxyl-protecting groups (A) such as dihydropyran or ethylvinyl ether in the presence of an acid catalyst such as p-toluensulfonic acid, 98% sulfuric acid or phosphorus oxychloride to form Compound VII and the product is isolated by standard procedures.

Compound IV of Table A is prepared according to the reaction sequence depicted in Tables B and C. Examples of Compounds having Formula IV which are used in the reaction

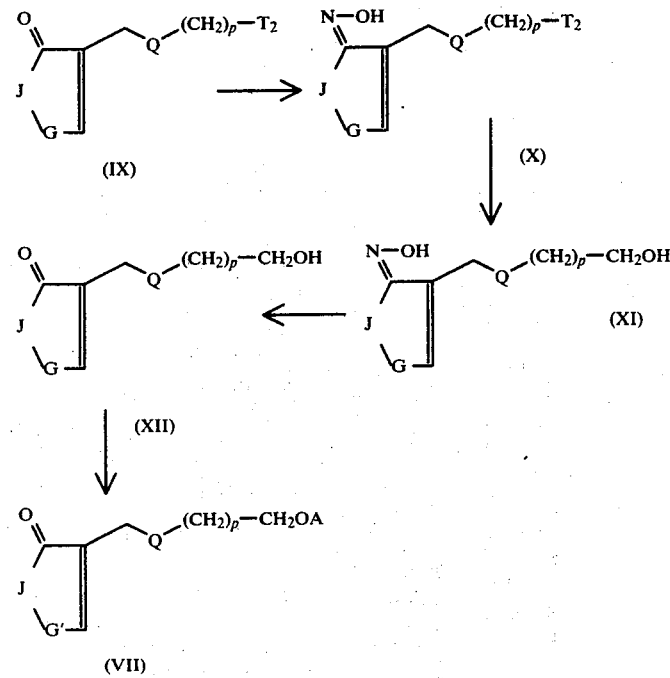

TABLE B

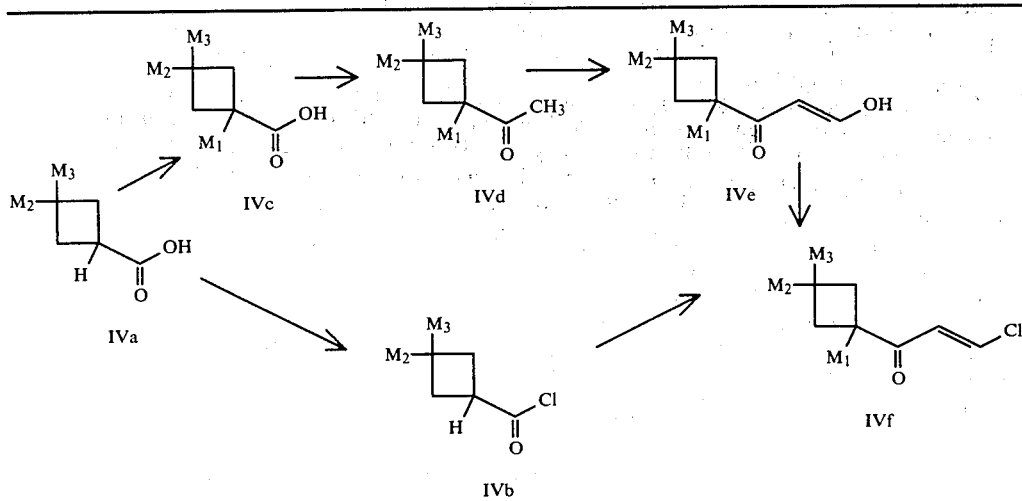

IV→III include: 1-iodo-3-(1-ethoxyethoxy)-3-(3-ethyl-cyclobutyl)-1E-propene; 1-iodo-3-(1-ethoxyethoxy)-3-(3-ethyl-1-methylcyclobutyl)-1E-propene; 1-iodo-3-(1-ethoxyethoxy)-3-(1-methylcyclobutyl)-1E-propene; 1-iodo-3-(1-ethoxyethoxy)-3-(1-butylcyclobutyl)-1E-propene; 1-iodo-3-(1-ethoxyethoxy)-3-[3-(3-cyclohexyl-propyl)cyclobutyl]-1E-propene; 1-iodo-3-(1-ethoxyethoxy)-3-[3-(cyclobutylmethyl)cyclobutyl]-1E-propene; 1-iodo-3-(1-ethoxyethoxy)-3-[3-(5-cyclododecyl-pentyl)cyclobutyl]-1E-propene, 1-iodo-3-(1-ethoxyethoxy)-3-[3-ethyl-3-(3-cyclohexylpropyl)cyclobutyl]-1E-propene and 1-iodo-3-(1-ethoxyethoxy)-3-(3-cyclobutyl-cyclobutyl)-1E-propene. The synthesis of Compound IV from the corresponding cyclobutane carboxylic acid IVa can be accomplished via the reaction sequence of Table B and C by well-known organic chemistry procedures.

Using the Reaction sequence, IVa→IVb→IVf, depicted in Table B, the cyclobutane carboxylic acid is converted into the β-chlorovinyl ketone IVf where $M_1$ is hydrogen. In IVa→IVb, the cyclobutane carboxylic acid is converted to the acid chloride IVb using an acid chloride forming reagent such as thionyl chloride, oxalyl chloride, phosphorus trichloride and the like as described in Fieser & Fieser, *Reagents for Organic Synthesis*, I:1158, J. Wiley & Sons, Inc. (1967). In IVb→IVf, the acid chloride IVb is reacted with acetylene in an inert solvent such as carbon tetrachloride, methylene chloride or the like, in the presence of a Lewis acid such as aluminum chloride, stannic chloride or the like to produce the β-chlorovinyl ketone IVf as described in *Chem. Rev.*, 161 (1965) and *Org. Synth., Coll. Vol.* IV:186, J. Wiley & Sons, Inc. (1963).

TABLE C

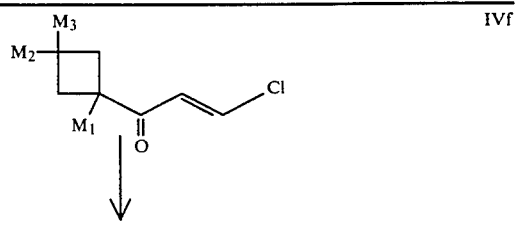

TABLE C-continued

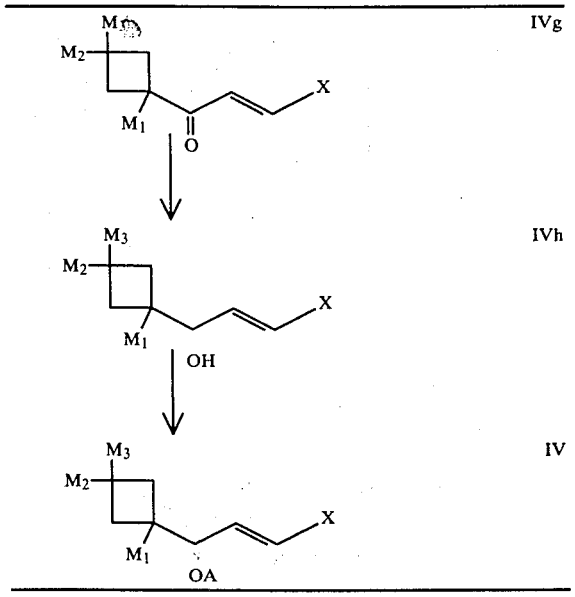

Using the reaction sequence, IVa→IVc→IVd-→IVe→IVf, depicted in Table B, the cyclobutanecarboxylic acid is converted into the β-chlorovinyl ketone IVf where $M_1$ is a lower alkyl of 1 to 5 carbon atoms. In IVa→IVc, the cyclobutanecarboxylic acid is converted to the lower alkyl substituted $M_1$ cyclobutanecarboxylic acid IVc using lithium diisopropylamine in an aprotic solvent such as tetrahydrofuran followed by treatment with a lower alkyl halide as described in *J. Amer. Chem. Soc.*, 92:1397 (1970). Lithium diisopropyl amine can be generated by mixing n-butyllithium with diisporopylamine in tetrahydrofuran. Sutitable lower alkyl halides include methyl iodide, ethyl bromide, 1-iodopropane, 2-iodopropane, 1-bromopropane, 2-bromopropane, 1-iodobutane, 1-bromopentane and 2-bromopentane. In IVc→IVd, the lower alkyl substituted $M_1$ cyclobutanecarboxylic acid IVc is converted to the corresponding methyl ketone IVd using methyl lithium as described in *J. Amer. Chem. Soc.*, 55:1258 (1933). In IVd→IVe, the lower alkyl substituted cyclobutyl methyl ketone (IVd) is converted to the corresponding hydroxy vinyl ketone (IVe) by treatment of a mixture of compound IVd and methyl formate with sodium hydride followed by treatment of the enolate in ether with hydrochloric acid to obtain the free enol as described in *Org. Syn. Coll. Vol.* 4:536 (1963) and *J. Amer. Chem. Soc.*, 76:552 (1954). In IVe→IVf, compound IVe is converted into the β-chlorovinyl ketone cyclohexylpropyl)-cyclobutanecarboxylic acid, 3-cyclobutylcyclobutane-1-carboxylic acid and the like. The cyclobutanecarboxylic acid of Formula IVa are either commercially available or are prepared by well-known organic chemistry techniques from commercially available materials. One such procedure is depicted by the reaction sequence of Table D.

TABLE D

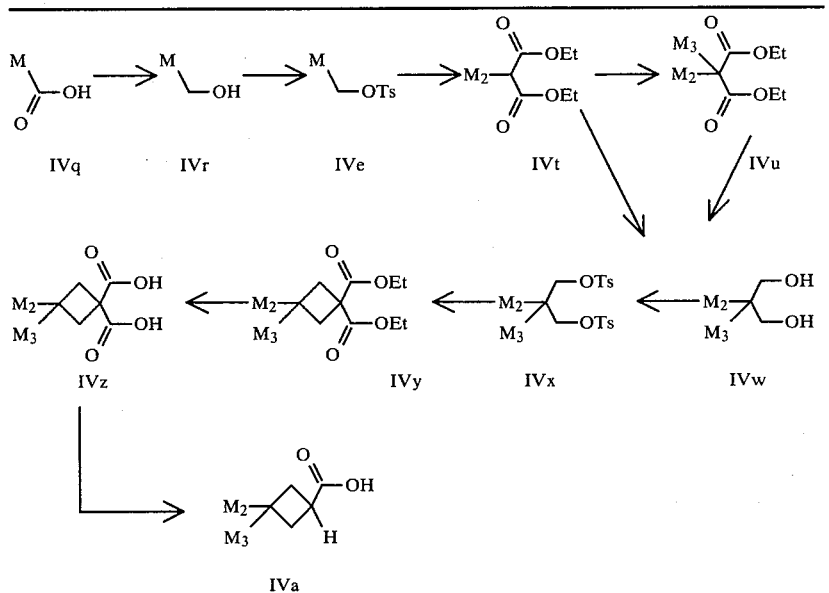

IVf using a chloride forming reagent, such as thionyl chloride in benzene as described in *Chem. Abstr.*, 49:10830f (1955).

In IVf→IVg (Table C), the β-chlorovinyl ketone (IVf) is converted to the corresponding β-iodo- or β-bromo-vinyl ketone IVg, where X is an iodo or bromo radical, using a soluble salt, such as sodium iodide, sodium bromide, lithium bromide or the like in a polar inert solvent, such as acetone, acetonitrite or the like, as described in *J. Amer. Chem. Soc.*, 94:7210 (1972). In IVg→IVh, compound IVg is reduced to the corresponding β-iodo- or β-bromo-vinyl alcohol using a suitable reducing agent, such as sodium borohydride in alcohol solvent or lithium aluminum hydride in ether solvent as described in *J. Amer. Chem. Soc.*, 94:7210 (1972). In IVh→IV, compound IVh is treated with a suitable hydroxyl-protecting agent (A) such as dihydropyran or ethylvinyl ether in the presence of an acid catalyst such as p-toluenesulfonic acid, 98% sulfuric acid or phosphorus oxychloride; or a trialkylsilylchloride, such as trimethylsilychloride or t-butyldimethylsilylchloride, or triphenylmethylbromide in the presence of a basic catalyst such as triethylamine or imidazole. Any hydroxyl-protecting group that is removable under mildly acid conditions and is stable to alkyllithium and alkylcopper(I) reagents can also be suitably used, see *J. Org. Chem.*, 37:1947 (1972).

Examples of the corresponding cyclobutanecarboxylic acids having formula IVa include: cyclobutanecarboxylic acid; 3-methylcyclobutanecarboxylic acid; 3-ethylcyclobutanecarboxylic acid; 3-propylcyclobutanecarboxylic acid; 3-butylcyclobutanecarboxylic acid; 3-pentylcylcobutanecarboxylic acid; 3-(3-cyclohexylpropyl)cyclobutanecarboxylic acid; 3-(cyclobutylmethyl)cyclobutanecarboxylic acid; 3-(5-cyclododecylpentyl)cyclobutane; 3-ethyl-3-(3-

In Table D, the reaction steps IVq to IVz are described in *Justus Liebigs Ann. Chem.*, 685:74 (1965) and *J. Org. Chem.*, 31:4069 (1966). In IVq→IVr, a carboxylic acid IVq, where M is hydrogen or —(CH$_2$)$_n$M$_4$ and n is zero or an integer from 1 to 4 and M$_4$ is as defined above, is reduced to the corresponding alcohol IVr, where M is as defined above, using a suitable reducing agent such as lithium aluminum hydride (see Fieser & Fieser, *Reagents for Organic Synthesis*, 1:581, J. Wiley & Sons (1967). In IVr→IVs, the alcohol IVr is treated with p-toluensulfonyl chloride in pyridine to form the tosylate IVs (see Fieser & Fieser, *Reagents for Organic Synthesis*, 1:1179, J. Wiley & Sons, [1967]). In IVs→IVt, the tosylate IVs is treated with the sodium enolate of diethylmalonate, prepared from sodium and diethylmalonate in xylene (see *Organic Reactions*, 9:107 [1957]) to form the diethyl alkylated malonate IVt. In IVt→IVw, the diethyl alkylated malonate IVt is reduced to the corresponding bis-hydroxymethyl derivative IVw using lithium aluminum hydride (see *Modern Synthetic Reactions*, 2nd Ed., 84, W. A. Benjamin, Inc. [1972]). Alternatively, in IVt→IVu, the diethyl alkylated malonate IVt is alkylated by treatment of the sodium enolate of diethyl alkylated malonate IVt with an alkylating agent such as a lower alkyl-tosylate, halide, carbonate, sulfonate or the like in xylene to form the diethyl dialkylated malonate IVu (see *Organic Reactions*, 9:107 [1957]). In IVu→IVw, the diethyl dialkylated malonate IVu is reduced as in IVt→IVw above, to the corresponding bis-hydroxymethyl derivative IVw using a reducing agent such as lithium aluminum hydride. In IVw→IVx, the bis-hydroxymethyl derivative IVw is converted to the ditosylate IVx by treatment with p-toluensulfonyl chloride as above. In IVx→IVy, the ditosylate IVx is converted to the 3-substituted cyclobutane-1,1-diethylester IVy by treatment with the sodium enolate of diethyl malonate as above. In IVy→IVz, compound IVy is hydrolyzed in a suitable base to yield the cyclobutane 1,1-dicarboxylic acid IVz. In IVz→IVa, the cyclobutane 1,1-dicarboxylic acid is decarboxylated by heating (see *Modern Synthetic Reactions,* 2nd Ed.; 513, W. A. Benjamin, Inc. [1972]) to produce the cyclobutanecarboxylic acid IVa.

In Table D, where $M_2$ is $-(CH_2)_n-M_4$ and n is 0, then the reaction step IVs to IVt is preferrably accomplished by reacting the tosylate IVs with sodium cyanide in Dimethylsulfoxide to form the mitrile-M CN ($IVs_1$) (see *J. Amer. Chem. Soc.,* 92, 336 [1970]). The nitrile $IVs_1$ is then treated with aqueous ethanol and aqueous potassium hydroxide to form the acid-M $CO_2H$ ($IVs_2$) (see *J. Amer. Chem. Soc.,* 98, 222 [1976]. The acid $IVs_2$ is then treated with sulfuric acid and absolute ethanol in a simple Fischer esterification step to form the ester M $CO_2Et$ ($IVs_3$). The ester $IVs_3$ is then treated with ethyl chloroformate and lithium dissopropylamide to form the diethyl alkylated malonate (IVt) (see *J. Org. Chem.,* 39, 2114 [1974]).

The compounds represented by Formula III inhibit aggregation of human platelets in vitro as demonstrated in the following Example 17. It is that feature which distinguishes the compounds of this invention over the natural prostaglandins. Of the natural prostaglandins, only $PGE_1$ displays a similar activity. The prostaglandin analogs of this invention also stimulate in vitro and in vivo smooth muscle preparations derived from a variety of tissues and organs of experimental animals. In particular, preferred prostaglandin analogs of this invention also exhibit selective gastric antisecretory and bronchodilatory activity. It has been found that the compounds of this invention exhibit fewer undesirable side activities than the natural prostaglandins. Such smooth muscle and in vivo assays are widely utilized to determine the activity of natural prostaglandins as well as prostaglandin analogs (Bundy et al., *Ann. N.Y. Acad. Sci.,* 180:76 [1961]; Bergstrom et al., *Pharmacal. Revs.,* 20:1 [1968]). Details of the activity of selected compounds having Formula III are presented in Example 43 below.

In order to further illustrate the novel aspects of the present invention, the following examples are presented. It should be recognized that these examples are provided by way of illustration only and are not intended to limit in any way the invention disclosed herein.

EXAMPLE 1

This example illustrates the preparation of 1-iodo-3-(1-ethoxyethoxy)-3-(3-ethylcyclobutyl)-1E-propene.

A. Preparation of 2-Ethylpropan-1,3-diol

Lithium aluminum hydride (15.5 g, 0.4 mole) was slurried in 600 ml of dry ether (distilled from benzophenone-ketyl, generated in situ from sodium and benzophenone). The slurry was cooled in an ice-water bath and then a solution of 37.6 g (0.2 mole) of diethyl ethylmalonate (Aldrich Chemical Company; Beilstein 2: 644) in 100 ml of dry ether was added thereto. The mixture was heated to reflux for 3 hr and then it was cooled in an ice-water bath. Ethyl acetate (52 ml) was carefully added, followed by water (15.5 ml), followed by the addition of 15.5 ml of 15% aqueous sodium hydroxide solution and then 31 ml of water. This mixture was filtered and the solvents were removed from the filtrate by evaporation in vacuo to yield 12.3 g of the title compound having the following physical characteristics:

Analysis—NMR($CDCl_3$): $\delta$0.6–2.0(6H,multiplet) and 3.1 to 3.9 ppm (6H,multiplet).

B. Preparation of 2-Ethylpropyl-1,3-ditosylate

A mixture containing 12.3 g (0.118 mole) of 2-ethylpropan-1,3-diol (prepared in 1A) and 350 ml of dry pyridine (distilled from calcium hydride) was prepared and cooled in an ice-water-salt bath. To this mixture there was then added 67.5 g (0.354 mole) of p-toluenesulfonyl chloride and the mixture was stirred for 3 hr at $-15°$ C. This mixture was then poured into 3 l of ice-cold 6 N hydrochloric acid. The resultant mixture was extracted with 1800 ml ($3 \times 600$ ml) of ether. The ether extracts were combined and dried over anhydrous potassium carbonate-sodium sulfate, filtered and the solvent removed in vacuo to yield 48.1 g of the title compound having the following physical characteristics:

Analysis—NMR($CDCl_3$): $\delta$0.8(3H,triplet,J=6 Hz), 1.35 (3H,triplet,J=6 Hz), 1.9(1H,quart), 2.48(6H,singlet), 3.9(4H,doublet,J=6 Hz), and 7.5 ppm (8H,AB,J=10 Hz).

C. Preparation of 3-Ethyl-1,1-dicarbethoxycyclobutane

Sodium metal (7.6 g, 0.33 g/atom) was dispersed in 50 ml of dry xylene (distilled from sodium hydride) by heating to 130° C. with rapid stirring. Dry xylene (168 ml) and 47.8 g (45.2 ml, 0.298 mole) of diethyl malonate were then added thereto and the mixture was allowed to react at 120° C. To the resultant mixture there was then added 48.1 g (0.116 mole) of 2-ethyl-propyl-1,3-ditosylate (prepared in 1B) dissolved in 120 ml of dry xylene. This reaction mixture was heated to about 150° C. and stirred for 18 hr. The mixture was cooled and poured into 500 ml of water and extracted with 600 ml ($3 \times 300$ ml) of ether. The aqueous material was made acidic with 10% aqueous HCl and then extracted with 600 ml ($2 \times 300$ ml) of ether. The combined ether extract was washed with 200 ml of saturated aqueous sodium chloride, dried over anhydrous magnesium sulfate, filtered and the solvent was removed in vacuo. Distillation of the product at reduced pressure yielded 7.0 g of the title compound having the following physical characteristics:

Analysis—NMR($CDCl_3$): $\delta$0.6(3H,triplet,J=7 Hz), 1.2 (6H,triplet,J=8 Hz), 1.9–2.8(7H,multiplet), and 4.3 ppm (4H,overlapping quartets,J=8 Hz).

D. Preparation of 3-Ethylcyclobutane-1,1-dicarboxylic acid

A solution of 7.0 g (0.031 mole) of 3-ethyl-1,1-dicarbethoxycyclobutane (prepared in 1C) dissolved in 7 ml of absolute ethanol was prepared. To this solution there was added 6.87 g (0.123 mole) of potassium hydroxide dissolved in 76 ml of absolute ethanol and the mixture was heated to reflux with stirring for 1.5 hr. The mixture was then filtered and the filter cake was washed with 10 ml of absolute ethanol and 75 ml of ether. The resulting filter cake was dissolved in 30 ml of ice water and acidified with 36 ml of 50% aqueous sulfuric acid. The resulting mixture was cooled, filtered and dried to yield 4.5 g of the title compound having the following physical characteristics:

Analysis—NMR($CDCl_3$): $\delta$0.85(3H,triplet,J=7 Hz), 1.1–1.7(3H,multiplet) and 1.8–2.8 ppm(4H,multiplet).

E. Preparation of 3-Ethylcyclobutane carboxylic acid

The 3-ethylcyclobutane-1,1-dicarboxylic acid (4.5 g, 0.026 mole; prepared in 1D) was decarboxylated by heating the compound to 190° C. for about 15 min. Frothing accompanied this decarboxylation and when this ceased the mixture was cooled to yield ca. 3.3 g of the title compound having the following physical characteristics:

Analysis—NMR(CDCl$_3$): δ0.8(3H,triplet,J=7 Hz), 1.1–3.4(11H,multiplet), and 12.3 ppm(1H,broad singlet).

F. Preparation of 3-Ethylcyclobutanecarboxylic acid chloride

A mixture of 3.3 g (0.027 mole) of 3-ethylcyclobutanecarboxylic acid (prepared in 1E) and 9.4 g (5.7 ml, 0.080 mole) of thionyl chloride was prepared and allowed to stir at room temperature for about 15 hr. Excess thionyl chloride was removed by distillation at atmospheric pressure. The residue was distilled at reduced pressure to yield 2.4 g of the title compound having the following physical characteristics:

Analysis—NMR(CDCl$_3$): δ0.8(3H,triplet,J=7 Hz), 1.1–1.6(3H,multiplet) and 1.8–2.8 ppm(4H,multiplet).

G. Preparation of 3-Ethylcyclobutyl-trans-β-chlorovinyl ketone

A solution of 8.4 g (0.058 mole) of 3-ethylcyclobutanecarboxylic acid chloride (prepared as in 1E) in 10 ml of carbon tetrachloride was added, under an acetylene atmosphere, to 9.7 g (0.072 mole) of anhydrous aluminum chloride slurried in 100 ml of carbon tetrachloride while being cooled in an ice-water bath. Acetylene was bubbled through the stirred mixture for 4 hours. The resultant mixture was then poured into 150 ml of ice and 150 ml of saturated aqueous sodium chloride. The phases which formed were separated and the aqueous phase was extracted with 300 ml (2×150 ml) of ether. The combined ether extracts were successively washed with 100 ml of 10% aqueous hydrochloric acid, 100 ml of saturated aqueous sodium bicarbonate and 100 ml of saturated aqueous sodium chloride. The resultant ether extract was dried over anhydrous magnesium sulfate, filtered and the solvent was removed in vacuo. The residue was chromatographed on silica gel 60 (0.063–0.2 mm, 70–230 mesh, ASTM) using benzene as the eluant to yield 3.92 g of the title compound having the following physical characteristics:

Analysis—NMR(CDCl$_3$): δ0.7(3H,triplet,J=8 Hz), 1.0–2.7(7H,multiplet)3.0(1H,multiplet), 6.4(1H,doublet, J=16 Hz), and 7.3 ppm(1H,doublet,J=16 Hz).

H. Preparation of 3-Ethylcyclobutyl-trans-β-iodovinyl ketone

A mixture containing 3.92 g (0.0228 mole) of 3-ethylclobutyl-trans-β-chlorovinyl ketone (prepared in 1F), and 13.6 g (0.091 mole) of sodium iodide and 70 ml of dry acetone (distilled from anhydrous potassium carbonate) was prepared and heated at reflux temperature with stirring for 18 hr. The mixture was cooled and the solvent was removed in vacuo. The solid residue was taken up in 50 ml of water and the products extracted with 150 ml (3×50 ml) of ether. The combined ether extract was successively washed with 30 ml of aqueous sodium thiosulfate solution and 30 ml of saturated aqueous sodium chloride. The washed ether extract was then dried over anhydrous magnesium sulfate, filtered and the solvent was removed in vacuo to yield 5.3 g of the title compound having the following characteristics:

Analysis—NMR(CDCl$_3$): δ0.8(3H,triplet,J=8 Hz), 1.0–2.6(7H,multiplet), 3.1(1H,multiplet), 7.0 (1H,doublet, J=15 Hz), and 7.6 ppm (1H,doublet,J=15 Hz).

I. Preparation of 1-(3-Ethylcyclobutyl)-trans-3-iodoprop-2-en-1-ol

A solution of 5.3 g (0.02 mole) of 3-ethylcyclobutyl-trans-β-iodovinyl ketone (prepared in 1H) dissolved in 200 ml of absolute ethanol was prepared and cooled in a salt-ice-water bath. Sodium borohydride (1.51 g, 0.04 mole) was slurried in 50 ml of absolute ethanol and added to the cooled solution. The resulting mixture was allowed to stir for 1 hr at 0° C. The solvent was removed in vacuo and the residue was taken up in 100 ml of water. The aqueous mixture was then extracted with 150 ml (3×50 ml) of ether. The combined ether extract was washed with 50 ml of saturated aqueous sodium chloride, dried over anhydrous magnesium sulfate, filtered, and the solvent removed in vacuo to yield 4.8 g of the title compound having the following physical characteristics:

Analysis—NMR (CDCl$_3$): δ0.8(3H,triplet,J=8 Hz), 1.0–2.3(3H,multiplet), 4.0(2H,multiplet), and 6.1–6.7 ppm (2H,multiplet).

J. Preparation of 1-iodo-3-(1-ethoxyethoxy)-3-(3-ethylcyclobutyl)-1E-propene A mixture containing 4.8 g (0.018 mole) of 1-(3-ethylcyclobutyl)-trans-3-iodoprop-2-en-1-ol (prepared in 1I) and 38.2 g (50 ml, 0.51 mole) of ethylvinyl ether (Aldrich Chemical Company; Beilstein 1:433) was prepared. One drop of phosphorus oxychloride was added thereto and the mixture was allowed to stir for about 15 hr at room temperature. The mixture was poured into 50 ml of saturated aqueous sodium bicarbonate and the products were extracted with 150 ml (3×50 ml) of ether. The combined ether extract was washed with 50 ml of saturated aqueous sodium chloride, dried over anhydrous magnesium sulfate, filtered, and the solvent was removed in vacuo. The residue was chromatographed on silica gel 60 (0.063–0.2 mm, 70–230 mesh, ASTM) using chloroform as the eluant to yield 4.2 g of the title compound having the following physical characteristics:

Analysis—NMR (CDCl$_3$): δ0.7 (3H,triplet,J=8 Hz), 1.0–1.5 (6H,multiplet), 1.5–2.5 (7H,multiplet), 3.5 (3H, multiplet), 4.5 (1H,quartet,J=6 Hz) and 6.1–6.5 ppm (2H,multiplet).

EXAMPLE 2

A. Preparation of 1-Methyl-3-ethylcyclobutanecarboxylic acid

A solution of 19.9 ml (140 mmol) of dry diisopropylamine in 100 ml of dry tetrahydrofuran was stirred in under an argon atmosphere and 63.6 ml (140 mmol) of a solution of n-butyllithium (2.2 M) in hexane was added dropwise thereto while maintaining the temperature below about 5° C. The resultant mixture was then stirred for 15 min with ice-bath cooling. A solution of 8.2 g (64 mmol) of 3-ethylcyclobutanecarboxlic acid (prepared in Example 1E) in 15 ml of dry tetrahydrofuran was added dropwise to the reaction mixture and stirred with cooling for 15 min. Methyl iodide (4.36 ml, 70 mmol) was added to the reaction mixture dropwise and the resultant mixture was stirred without cooling for 2 hr. The mixture was then stirred with ice-methanol bath cooling as 10% hydrochloric acid was added dropwise until the resultant aqueous phase was acidic (about 25 ml was used). The aqueous phase was separated and extracted twice with ether. The combined ether extract was dried over anhydrous magnesium sulfate and the solvent removed in vacuo to yield 10 g of the title compound having the following physical characteristics:

Analysis—NMR (CDCl$_3$): δ0.8 (3H,broad triplet,J=7.0 Hz), 1.0 to 3.0 (7H,multiplet), 1.37 and 1.47 (3H,total two singlets, two isomers), 10.6 ppm (1H,broad singlet).

B. Preparation of 1-Methylcyclobutanecarboxylic acid

The title compound was prepared as in Example 2A by replacing 3-ethylcyclobutanecarboxylic acid with cyclobutanecarboxylic acid (Aldrich Chemical Company; Beilstein: 9,5). The resultant product had the following physical characteristics:

Analysis—NMR (CDCl$_3$): δ1.43 (3H,singlet), 1.5–2.7 (6H,multiplet), 12.5 ppm (1H,singlet); IR(CHCl$_3$)ν: 660, 730, 760, 1210, 1700 and 2400 to 3300 cm$^{-1}$ (broad).

C. Preparation of 1-Butylcyclobutanecarboxylic acid

The title compound was prepared as in Example 2A by replacing 3-ethylcyclobutanecarboxylic acid and methyl iodide respectively with cyclobutanecarboxylic acid and 1-iodobutane (Aldrich Chemical Company; Beilstein 1: 123). The resultant product had the following physical characterisics:

Analysis—NMR(CDCl$_3$): δ0.92 (3H,broad triplet,J=6 Hz), 1.0 to 2.8 (12H,multiplet), 12.3 ppm (1H, broad singlet) IR(CHCl$_3$)ν: 1250, 1695 and 2400 to 3500 cm$^{-1}$ (broad).

EXAMPLE 3

A. Preparation of (1-Methyl-3-ethylcyclobutyl) methyl ketone

A solution of 5.0 g (35 mmol) of 1-methyl-(3-ethyl)-cyclobutanecarboxylic acid (prepared in Example 2A) in 35 ml of dry ether was stirred with ice-bath cooling under an argon atmosphere and 40 ml of a 2 M solution of methyllithuim in ether was added thereto. The resultant mixture was stirred without cooling for 3 hr. This mixture was then quenched by pouring the mixture into a vigorously stirred solution of 30 ml of methanol and 70 ml of water. The aqueous phase was separated and extracted twice with ether. The combined ether extract was dried over anhydrous magnesium sulfate and evaporated. The residue was distilled at reduced pressure to yield 2.5 g of the title compound having the following physical characteristics:

Analysis—NMR(CDCl$_3$): δ0.79 (3H,broad triplet, J=6.5 Hz), 1.33 and 1.38 (3H,total,two singlet, isomers), 1.0 to 2.8 (7H,multiplet), 2.07 and 2.16 ppm (3H, total, two singlets, isomers).

B. Preparation of (1-Methylcyclobutyl) methyl ketone

The title compound was prepared according to the procedure of Example 3A by replacing 1-methyl-3-ethylcyclobutanecarboxylic acid with 1-methylcyclobutanecarboxylic acid (prepared in Example 2B). The resultant product had the following physical characteristics:

Analysis—NMR(CDCl$_3$): δ1.36 (3H,singlet), 2.09 (3H, singlet), 1.4 to 2.6 ppm (6H,multiplet); IR(CHCl$_3$)ν: 1120, 1350, 1700, 2870 and 2960 cm$^{-1}$.

C. Preparation of (1-Butylcyclobutyl) methyl ketone

The title compound was prepared according to the procedure of Example 3A by replacing 1-methyl-3-ethylcyclobutanecarboxylic acid with 1-butylcyclobutanecarboxylic acid (prepared in Example 2C). The resultant product had the following physical characteristics:

Analysis—NMR(CDCl$_3$): δ0.90 (3H,broad triplet,J=6 Hz), 1.0 to 2.8 (12H, multiplet), 2.07 (3H, singlet); IR(CHCl$_3$)ν: 1130, 1360, 1695, 2860, 2940 and 2960 cm$^{-1}$.

EXAMPLE 4

A. Preparation of 1-Hydroxy-3-(3-ethyl-1-methylcyclobutyl)-prop-1-en-3-one

Sodium hydride (1.25 g of 50% mineral oil dispersion, 50 mmol) was washed with dry hexane and then stirred under an argon atmosphere with 12.5 ml of dry ether. A solution of 5 ml of methyl formate and 2.4 g of (1-methyl-3-ethylcyclobutyl) methyl ketone (prepared in Example 3A) in 5 ml of ether was then added to the reaction mixture along with about 0.5 ml of methanol. As a voluminous precipitate formed, sufficient ether was added to make the reaction mixture more easily stirred. The resultant mixture was stirred for 1 hr and then quenched by the addition of water. The ether phase was separated and extracted three times with 1 M sodium hydroxide. The combined aqueous extraction phases were acidified with concentrated hydrochloric acid and extracted three times with ether. The combined ether extract was evaporated in vacuo. Traces of water were removed by twice addition of benzene which was removed by evaporation in vacuo. The title compound had the following physical characteristics:

Analysis—NMR(CDCl$_3$): δ0.8 (3H,broad triplet, J=6.5 Hz), 1.3 and 1.37 (3H total,two singlets, isomers), 1.0 to 2.8 (7H,multiplet), 5.57 and 5.73 (1H total,two doublets, J=4.5 Hz,isomer), 7.5 (1H, singlet), 8.00 and 8.04 ppm (1H,total, two doublets, J=4.5 Hz,isomers).

B. Preparation of 1-Hydroxy-3-(1-methylcyclobutyl)-prop-1-en-3-one

The title compound was prepared according to the procedure of Example 4A by replacing (1-methyl-3-ethylcyclobutyl) methyl ketone with (1-methylcyclobutyl) methyl ketone prepared in Example 3B. The resultant product had the following physical characteristics:

Analysis—NMR(CDCl$_3$): δ1.40 (3H,singlet), 1.5 to 2.7 (6H,multiplet), 5.61 (1H,doublet,J=4.5 Hz), 7.45 (1H, singlet), 8.04 ppm (1H,doublet,J=4.5 Hz); IR(CHCl$_3$)ν: 660, 740, 1075, 1255, 1595, 1635, 2880 and 2970 cm$^{-1}$.

C. Preparation of 1-Hydroxy-3-(1-butylcyclobutyl)-prop-1-en-3-one

The title compound was prepared according to the procedure of Example 4A by replacing (1-methyl-3-ethylcyclobutyl) methyl ketone with (1-butylcyclobutyl) methyl ketone prepared in Example 3C. The resultant product had the following physical characteristics:

Analysis—NMR(CDCl$_3$): δ0.88 (3H,broad triplet, J=6 Hz), 1.0 to 2.8 (12H,multiplet), 5.62 (1H,doublet, J=4.5 Hz), 7.98 (1H,doublet,J=4.5 Hz), 7.8 ppm (1H,very broad singlet); IR(CHCl$_3$)$\nu$: 1080, 1250, 1450, 1590, 1630, 2860, 2930 and 2960 cm$^{-1}$.

EXAMPLE 5

A. Preparation of trans-1-Chloro-3-(3-ethyl-1-methylcyclobutyl)-prop-1-en-3-one A solution of 5.8 g of 1-hydroxy-3-(3-ethyl-1-methylcyclobutyl)-prop-1-en-3-one (prepared in Example 4A) in 100 ml of benzene was stirred under an argon atmosphere and 7 ml of thionyl chloride in 10 ml of benzene was added dropwise. The resulting solution was stirred for about 15 hr. Excess solvent was removed by distillation at atmospheric pressure and the residue was then distilled in vacuo to yield 4.2 g of the title compound having the following physical characteristics:

Analysis—NMR(CDCl$_3$): $\delta$0.80 (3H,broad triplet,J=6.5 Hz), 1.0 to 3.0 (7H,multiplet), 1.33 and 1.40 (3H total, singlet,isomers), 6.72 and 6.87 (1H total,two doublet, J=13.5 Hz,isomers), 7.48 and 7.51 ppm (1H total, two doublets, J=13.5 Hz).

B. Preparation of trans-1-Chloro-3-(1-methylcyclobutyl)-prop-1-en-3-one

The title compound was prepared according to the procedure of Example 5A by replacing 1-hydroxy-3-(3-ethyl-1-methylcyclobutyl)-prop-1-en-3-one with 1-hydroxy-3-(1-methylcyclobutyl)-prop-1-en-3-one prepared in Example 4B. The resultant product had the following physical characteristics:

Analysis—NMR (CDCl$_3$): $\delta$1.38 (3H,singlet), 1.5 to 2.7 (6H,multiplet), 6.73 (1H,doublet,J=12.5 Hz), 7.46 ppm (1H,doublet,J=12.5 Hz); IR(CHCl$_3$)$\nu$: 660, 760, 1210, 1590, 1710, 2880 and 2970 cm$^{-1}$.

C. Preparation of trans-1-chloro-3-(1-butylcyclobutyl)-prop-1-en-3-one

The title compound was prepared according to the procedure of Example 5A by replacing 1-hydroxy-3-(3-ethyl-1-methylcyclobutyl)-prop-1-en-3-one with 1-hydroxy-3-(1-butylcyclobutyl)-prop-1-en-3-one prepared in Example 4C. The resultant product had the following physical characteristics:

Analysis—NMR(CDCl$_3$): $\delta$0.88 (3H,broad triplet, J=6 Hz), 1.0 to 2.9 (12H,multiplet), 6.72 (1H,doublet, J=13.5 Hz), 7.48 ppm (1H,doublet,J=13.5 Hz); IR(CHCl$_3$)$\nu$: 940, 1085, 1590, 1690, 2860, 2940 and 2970 cm$^{-1}$.

EXAMPLE 6

A. Preparation of trans-1-iodo-3-(3-ethyl-1-methylcyclobutyl)-prop-1-en-3-one A solution of 4.2 g of trans-1-chloro-3-(3-ethyl-1-methylcyclobutyl)-prop-1-en-3-one (prepared in Example 5A) and 10 g of anhydrous sodium iodide in 60 ml of acetone was refluxed with about 0.5 ml H$_2$SO$_4$ for 4 hr under an argon atmosphere. The solvent was removed by evaporation in vacuo. The residue was diluted with water and the aqueous mixture was extracted several times with ether. The combined ether extract was washed with aqueous sodium thiosulfate solution and then dried over anhydrous magnesium sulfate and evaporated in vacuo to yield 6.8 g of the title compound having the following physical characteristics:

Analysis—NMR(CDCl$_3$): $\delta$0.80 (3H,broad triplet,J=6.5 Hz), 1.32 and 1.39 (3H total, two singlets,isomers), 1.0 to 2.8 (7H,multiplet), 7.32 and 7.45 (1H total, two doublets, J=14.5 Hz,isomers), 8.00 and 8.03 ppm (1H total, two doublets,J=14.5 Hz, isomers).

B. Preparation of trans-1-Iodo-3-(1-methylcyclobutyl)-prop-1-en-3-one

The title compound was prepared according to the procedure of Example 6A by replacing trans-1-chloro-3(3-ethyl-1-methylcyclobutyl)-prop-1-en-3-one with trans-1-chloro-3-(1-methylcyclobutyl)-prop-1-en-3-one prepared in Example 5B. The resultant product had the following physical characteristics:

Analysis—NMR(CDCl$_3$): $\delta$1.38 (3H,singlet, 1.5 to 2.7 (6H,multiplet), 7.36 (1H,doublet,J=15 Hz), 7.98 ppm (1H,doublet,J=15 Hz); IR(CHCl$_3$)$\nu$: 950, 1080, 1570, 1690, 2870 and 2960 cm$^{-1}$.

C. Preparation of trans-1-Iodo-3-(1-butylcyclobutyl)-prop-1-en-3-one

The title compound was prepared according to the procedure of 6A by replacing trans-1-chloro-3-(3-ethyl-1-methylcyclobutyl)-prop-1-en-3-one with trans-1-chloro-3-(1-butylcyclobutyl)-prop-1-en-3-one prepared in Example 5C. The resultant product had the following physical characteristics:

Analysis—NMR(CDCl$_3$): $\delta$0.9 (3H,broad triplet,J6 Hz), 1.0 to 2.8 (12H,multiplet), 7.37 (1H,doublet,J=15 Hz), 8.02 ppm (1H,doublet,J=15 Hz); IR(CHCl$_3$)$\nu$: 940, 1080, 1565, 1685, 2870, 2940 and 2870 cm$^{-1}$.

EXAMPLE 7

A. Preparation of trans-1-Iodo-3-hydroxy-3-(3-ethyl-1-methylcyclobutyl)-prop-1-ene The title compound was prepared according to Example 1I by replacing 3-ethylcyclobutyl-trans-$\beta$-iodovinyl ketone with trans-1-iodo-3-(3-ethyl-1-methylcyclobutyl-prop-1-en-3-one (prepared in Example 6A). The resultant product was purified by chromatography on silica gel 60 using a chloroform elution and had the following physical characteristics:

Analysis—NMR(CDCl$_3$): $\delta$0.78 (3H,broad triplet,J=6.5 Hz), 1.01 and 1.10 (3H total,two singlets,isomers), 1.0 to 2.7 (8H,multiplet), 4.0(1H,multiplet) and 6.15 to 6.95 ppm (2H,multiplet).

B. Preparation of trans-1-Iodo-3-hydroxy-3-(1-methylcyclobutyl)-prop-1-ene

The title compound was prepared according to the procedure of Example 1I by replacing 3-ethylcyclobutyl-trans-$\beta$-iodo-vinyl ketone with trans-1-iodo-3-(1-methylcyclobutyl)-prop-1-en-3-one prepared in Example 6B. The resultant product had the following physical characteristics:

Analysis—NMR(CDCl$_3$): $\delta$1.10 (3H,singlet), 1.3 to 2.7 (6H,multiplet), 4.02(1H,doublet,J=5 Hz) and 6.2 to 7.2 ppm (2H,multiplet); IR(CHCl$_3$)$\nu$: 910, 1610, 2880, 2950, 3200 to 3600 (broad) and 3610 cm$^{-1}$.

C. Preparation of trans-1-Iodo-3-hydroxy-3-(1-butylcyclobutyl)-prop-1-ene

The title compound was prepared according to the procedure of Example 1I by replacing 3-ethylcyclobutyl-trans-$\beta$-iodo-vinyl ketone with trans-1-iodo-3-(1- butylcyclobutyl)-prop-1-en-3-one (prepared in Example 6C). The resultant product had the following physical characteristics:

Analysis—NMR(CDCl₃): δ0.92 (3H,broad triplet,J=5 Hz), 1.0 to 2.7 (12H,multiplet), 4.1 (1H,triplet,J=5 Hz), 6.43 (1H,doublet,J=14 Hz), 6.79 ppm (1H,doublet, J=14.5 Hz); IR(CHCl₃)ν: 905, 950, 1610, 2870, 2940, 2970, 3200 to 3600 (broad) and 3605 cm⁻¹.

EXAMPLE 8

A. Preparation of 1-Iodo-3-(1-ethoxyethoxy)-3-(3-ethyl-1-methylcyclobutyl)-1E-propene A solution of 2.25 g (8.0 mmol) of trans-1-iodo-3-hydroxy-3-(3-ethyl-1-methylcyclobutyl)-prop-1-ene (prepared in Example 7A) in 8.0 ml of dry ether was stirred under an argon atmosphere and 1.2 ml of ethylvinylether was added thereto followed by about 5 mg of toluenesulfonic acid. The resultant solution was stirred under argon for 1.5 hr at 25° C. Saturated aqueous sodium bicarbonate was added to the reaction mixture and the aqueous mixture was then extracted with ether. The ether phase was separated and washed with saturated aqueous sodium chloride, dried over anhydrous magnesium sulfate and evaporated in vacuo to yield 2.7 g of the title compound having the following physical characteristics:

Analysis—NMR(CDCl₃): δ0.8 (3H,broad triplet,J=6.5 Hz), 0.9 2.5(16H,multiplet), 3.7(3H,multiplet), 4.8 (1H, broad quarter,J=5.3 Hz), 6.5 ppm (2H,multiplet); IR (CHCl₃)ν: 945, 1020, 1090, 1120, 1380, 1460, 1605, 2870, 2930 and 2960 cm⁻¹.

B. Preparation of 1-Iodo-3-(1-ethoxyethoxy)-3-(1-methylcyclobutyl)-1E-propene

The title compound was prepared according to the procedure of Example 8A by replacing trans-1-iodo-3-hydroxy-3-(3-ethyl-1-methylcyclobutyl)-prop-1-ene with trans-1-iodo-3-hydroxy-3-(1-methylcyclobutyl)-prop-1-ene prepared in Example 7B. The resultant product had the following physical characteristics:

Analysis—NMR(CDCl₃): δ1.10 (3H,singlet), 1.0 to 2.4 (12H,multiplet), 3.4 to 4.2 (3H,multiplet), 4.77 (1H,multiplet), 6.2 to 6.8 ppm (2H,multiplet); IR (film)ν: 945, 1015, 1095, 1130, 1380, 1605, 2870, 2930 and 2980 cm⁻¹.

C. Preparation of 1-Iodo-3-(1-ethoxyethoxy)-3-(1-butylcyclobutyl)-1E-propene

The title compound was prepared according to the procedure of Example 8A by replacing trans-1-iodo-3-hydroxy-3-(3-ethyl-1-methylcyclobutyl)-prop-1-ene with trans-1-iodo-3-hydroxy-3-(1-butylcyclobutyl)-prop-1-ene prepared in Example 7C. The resultant product had the following physical characteristics:

Analysis—NMR(CDCl₃): δ0.7 to 2.6 (21H,multiplet), 3.2 to 4.2(3H,multiplet), 4.8(1H,multiplet), 6.2 to 6.9 ppm (2H,multiplet); IR(CHCl₃)ν: 950, 1020, 1095, 1125, 1385, 1610, 2870 and 2940 cm⁻¹.

EXAMPLE 9

A. Preparation of 3-Cyclohexylpropan-1-ol

Lithium aluminum hydride (24.2 g, 0.64 mole) was slurried into 300 ml of dry ether (distilled from benzophenone ketyl, generated in situ from sodium and benzophenone). The slurry was cooled in an ice-water bath and a solution of 100 g (0.64 mole) of 3-cyclohexylpropionic acid (Bielstein 9:[2]13) in 250 ml of dry ether was slowly added. The resultant mixture was heated to reflux for 1 hr and then cooled in an ice-water bath. Ethyl acetate (100 ml) was slowly added to the mixture. This addition was followed by the addition of 24.2 ml of water, 24.2 ml of 15% aqueous sodium hydroxide solution and 72.6 ml of water. The mixture was filtered and the solvent was removed in vacuo. Distillation of this mixture at reduced pressure resulted in 71.6 g (78.7%) of pure 3-cyclohexylpropan-1-ol having the following physical characteristics:

Analysis—NMR(CDCl₃): δ0.7–2.1 (15H,multiplet) 3.63 ppm (2H,triplet,J=6 Hz).

B. Preparation of Cyclobutylmethanol

The title compound was prepared according to the procedure of Example 9A by reducing cyclobutanecarboxylic acid (Aldrich; Bielstein 9:5) with lithium aluminum hydride in ether. The resulting product had the following physical characteristics:

Analysis—NMR(CDCl₃): δ1.0–2.9 (7H,multiplet) δ3.6 (2H,doublet,J-7 Hz) 3.9 ppm (1H,broad singlet).

C. Preparation of 5-Cyclododecylpentan-1-ol i. 5-cyclododecylidenepentanoic acid Dry dimethylsulfoxide (50 ml, distilled from calcium hydride) and 24.1 ml (0.06 mole) of the sodium salt of dimethylsulfoxide (2.49 M in dimethylsulfoxide, Fieser and Fieser, "Reagents for Organic Synthesis", 1:310 [1967]) were mixed together and cooled in an ice-water bath. Then 13.29 g (0.03 mole) of (4-carboxybutyl) triphenylphosphonium bromide (Aldrich Chemical Co.) was added thereto and the mixture was stirred for 30 min. Cyclododecanone (3.64 g, 0.02 mole; Aldrich Chemical Co.: Beilstein 7[2],36) was dissolved in 10 ml of dry dimethylsulfoxide and added to the above mixture and the mixture was stirred for 15 hr at room temperature. The resulting mixture was then poured into 500 ml of water. This aqueous mixture was extracted with 900 ml (3×300 ml) of ether-ethyl acetate (1:1 V/V). The aqueous phase was acidified (pH 1 to 2) with 30 ml of concentrated hydrochloric acid. The aqueous phase was then extracted with 900 ml (3×300 ml) of ether-hexane (1:1 V/V). The ether-hexane extract was then dried over anhydrous magnesium sulfate, filtered, and the solvent removed in vacuo. The resultant product was recrystallized from ethanol-water to yield 2.0 g (36.2%) of 5-cyclododecylidenepentanoic acid (mp 70°–72° C.) having the following physical characteristics:

Analysis—NMR(CDCl₃): δ1.0–2.5 (28H,multiplet); 5.2(1H, triplet,J=7 Hz); 10.0 ppm (1H,broad singlet).

ii. 5-Cyclododecylpentanoic acid

From Example 9Ci above, 0.276 g (0.001 mole) of 5-cyclododecylidene pentanoic acid was dissolved in 30 ml of glacial acetic acid. Platinum oxide (0.027 g) was added and the mixture was hydrogenated on a sloping-manifold hydrogenation apparatus for 3 hr at room temperature. The resultant mixture was then filtered through Celite (diatomaceous earth). The solvent was removed in vacuo to yield 0.26 g (93.8%) of 5-cyclododecylpentanoic acid having the following physical characteristics:

Analysis—NMR(CDCl$_3$): δ1.0–2.2 (31H, multiplet), 11.8 ppm (1H, broad singlet).

iii. 5-Cyclododecylpentan-1-ol

The title compound was prepared according to the procedure described in Example 9A by reducing the 5-cyclododecylpentanoic acid (9Cii above) with lithium aluminum hydride in ether. The resultant product had the following physical characteristics:

Analysis—NMR(CDCl$_3$): δ0.7–2.0 (31H, multiplet), 3.7 (2H, triplet, J=6 Hz), 4.1 ppm (1H, broad singlet).

EXAMPLE 10

A. Preparation of 3-Cyclohexylpropyl-1-tosylate

3-Cyclohexylpropan-1-ol (1.42 g, 0.01 mole; prepared according to Example 9A) was mixed with 25 ml of freshly distilled pyridine (distilled from calcium hydride). The mixture was cooled in an ice-water bath and 3.80 g (0.02 mole) of p-toluene sulfonyl chloride was added with stirring. The mixture was poured into 150 ml of ice water and the aqueous mixture was extracted with 150 ml (3×50 ml) of ether. The combined ether extracts were washed with 100 ml (2×50 ml) of ice cold 6 N hydrochloric acid and 100 ml of ice water. The resultant ether extract was dried over anhydrous sodium sulfate-anhydrous potassium carbonate, filtered, and the solvent was removed in vacuo to yield 2.87 g (96.9%) of the title compound having the following physical characteristics:

Analysis—NMR(CDCl$_3$): δ0.6–2.1 (15H, multiplet), 2.48 (3H, singlet), 4.0 (2H, triplet, J=6 Hz), 7.5 ppm (4H, quartet, J=8 Hz).

B. Preparation of (Cyclobutylmethyl) tosylate

The title compound was prepared according to the procedure of Example 10A by replacing 3-cyclohexylpropan-1-ol with (cyclobutyl) methanol (prepared in Example 9B). The resultant product had the following physical characteristics:

Analysis—NMR(CDCl$_3$): δ0.9–2.1 (10H, multiplet), 2.4 (6H, singlet), 3.8 (4H, doublet, J=5 Hz), 7.4 ppm (8H, multiplet).

C. Preparation of 5-Cyclododecylpentyl-1-tosylate

The title compound was prepared according to the procedure of Example 10A by replacing 3-cyclohexylpropan-1-ol with 5-cyclododecylpentan-1-ol prepared in Example 9Ciii). The resultant product had the following physical characteristics:

Analysis—NMR(CDCl$_3$): δ0.6–2.0 (31H, multiplet), 2.5 (3H, singlet), 4.1 (2H, triplet, J=6 Hz), 7.55 ppm (4H, AB, J=8 Hz).

EXAMPLE 11

A. Preparation of Diethyl-2-(3-cyclohexylpropyl) malonate

Sodium metal (0.39 g, 0.0172 g/atom) was granulated by heating in 4.11 ml of dry xylene (distilled from sodium hydride) under nitrogen with rapid stirring. The slurry was diluted with 16.44 ml of dry xylene. Diethyl malonate (4.95 g, 4.70 ml, 0.031 mole) was added and the mixture was heated to 150° C. until the sodium was consumed. 3-Cyclohexylpropyl-1-tosylate (2.69 g, 0.01 mole; prepared by Example 11A) was dissolved in 8.22 ml of dry xylene and added to the sodiodethyl malonate. This mixture was then heated to 150° C. for 6 hr. The reaction mixture was cooled and 50 ml of water was added. The phases were separated and the aqueous phase was extracted with 70 ml (2×35 ml) of xylene. The xylene extract was washed with 50 ml of 6 N hydrochloric acid and 50 ml of water. The resulting extract was dried over anhydrous magnesium sulfate, filtered, and the solvent was removed in vacuo. The product was distilled at reduced pressure to yield 2.2 g (78.5%) of the title compound having the following physical characteristics:

Analysis—NMR(CDCl$_3$): δ0.7–2.2 (23H, multiplet), 3.42 (1H, triplet, J=7 Hz), 4.3 ppm (4H, quarter, J=8 Hz).

B. Preparation of Diethyl (cyclobutylmethyl) malonate

The title compound was prepared according to Example 11A by replacing 3-cyclohexylpropyl-1-tosylate with the (cyclobutylmethyl) tosylate prepared in Example 10B. The resultant product had the following physical characteristics:

Analysis—NMR(CDCl$_3$): δ1.0–2.8 (20H, multiplet), 4.2 ppm (4H, two overlapping quarters, J=8 Hz).

C. Preparation of Diethyl (5-cyclododecylpentyl) malonate

The title compound was prepared according to Example 11A by replacing 3-cyclohexylpropyl)-1-tosylate with the 5-cyclododecylpentyl-1-tosylate prepared in Example 10C. The resultant product had the following physical characteristics:

Analysis—NMR(CDCl$_3$): δ0.6–2.0 (39H, multiplet), 3.3 (1H, triplet, J=8 Hz), 4.2 ppm (4H, quartet, J=6 Hz).

EXAMPLE 12

A. Preparation of 2-(3-Cyclohexylpropyl)-propane-1,3-diol

The title compound was prepared according to the procedure of Example 1A by replacing diethyl ethylmalonate with diethyl-2-(3-cyclohexylpropyl) malonate (prepared in Example 11A). The resultant product had the following physical characteristics:

Analysis—NMR(CDCl$_3$: δ0.6–2.0 (18H, multiplet), and 3.1 to 4.3 ppm (6H, multiplet).

B. Preparation of 2-(Cyclobutylmethyl)-propane-1,3-diol

The title compound was prepared according to the procedure of Example 12A by replacing diethyl-2-(3-cyclohexlpropyl) malonate with diethyl-(cyclobutylmethyl) malonate (prepared in Example 11B). The resultant product had the following physical characteristics:

Analysis—NMR(CDCl$_3$): δ1.2–2.8 (10H, multiplet), 3.1 (2H, broad singlet), and 3.8 ppm (4H, multiplet).

C. Preparation of 2-(5-Cyclododecylpentyl)-propane-1,3-diol

The title compound was prepared in 84.7% yield according to the procedure of Example 12A by replacing diethyl-2-(3-cyclohexylpropyl) malonate with the diethyl-5-(cyclododecylpentyl) malonate prepared in Example 11C.

D. Preparation of 2-(3-Cyclohexylpropyl)-2-ethylpropane-1,3-diol i. Diethyl-2-ethyl-2-(3-cyclohexylpropyl)-malonate

Sodium metal (3.16 g, 0.137 g/atom) was dispersed by heating with rapid stirring in 80 ml of dry xylene at 110° to 120° C. The mixture was cooled and the xylene was removed with a filter stick. Dry toluene (300 ml distilled from calcium hydride) was added thereto and followed by the addition of 28.17 g (0.149 mole) of diethyl ethylmalonate. This mixture was slowly heated to 150° C. 3-Cyclohexylpropyl-1-tosylate (28.3 g, 1.1956 mole; prepared by Example 10A) was dissolved in 80 ml of dry toluene. This solution was then added to the sodiodiethylethylmalonate above and the mixture was stirred at 150° C. for 10 hr. The mixture was cooled and poured into 500 ml of water. The phases were separated and the aqueous phase was extracted with 500 ml (2×250 ml) of ether. The ether extract was washed with 250 ml of saturated sodium chloride solution, dried over a anhydrous magnesium sulfate and filtered. The solvents were removed in vacuo. The product was distilled at reduced pressure to yield 19.4 g of the title compound having the following physical characteristics:

Analysis—NMR(CDl$_3$): δ0.6–2.0 (28H, multiplet), 4.1 ppm (4H, quartet, J=8 Hz).

ii. 2-(3-Cyclohexylpropyl)-2-ethyl-propane-1,3-diol

The title compound was prepared according to the procedure of Example 12A by replacing diethyl-2-(3-cyclohexylpropyl) malonate with the diethyl-2-ethyl-2-(3-cyclohexylpropyl) malonate prepared in Example 11Di. The resultant product had the following physical characteristics:

Analysis—NMR(CDCl$_3$): δ0.5–1.9 (22H, multiplet), 3.1 (2H, broad multiplet), 3.5 ppm (2H, multiplet).

EXAMPLE 13

A. Preparation of 2-(3-Cyclohexylpropyl)-propane-1,3-ditosylate

The title compound was prepared according to the procedure of Example 1B by replacing 2-ethylpropane-1,3-diol with 2-(3-cyclohexylpropyl)-propane-1,3-diol (prepared in Example 12A). The resultant product had the following physical characteristics:

Analysis—NMR(CDCl$_3$): δ0.6–2.1 (18H, multiplet), 2.5 (6H, singlet), 3.95 (4H, doublet, J=5 Hz), and 7.55 ppm (8H, AB, J=8 Hz).

B. Preparation of 2-(Cyclobutylmethyl)-propane-1,3-ditosylate

The title compound was prepared according to the procedure of Example 13A by replacing 2-(3-cyclohexylpropyl)-propane-1,3-diol with 2-(cyclobutylmethyl)-propane-1,3-diol prepared in Example 12B. The resultant product had the following physical characteristics:

Analysis—NMR(CDCl$_3$): δ1.4–2.3 (7H, multiplet), 2.55 (3H, singlet), 40.5 (1H, doublet, J=6 Hz), 7.55 ppm (4H, AB, J=8 Hz).

C. Preparation of 2-(5-Cyclododecylpentyl)-propane-1,3-ditosylate

The title compound was prepared according to the procedure of Example 13A by replacing 2-(3-cyclohexylpropyl)-propane-1,3-diol with 2-(5-cyclododecylpentyl)-propane-1,3-diol (prepared in Example 12C). The resultant product had the following physical characteristics:

Analysis—NMR(CDCl$_3$): δ0.8–2.2 (34H, multiplet), 2.48 (6H, singlet), 4.05 (4H, multiplet), 7.55 ppm (8H, AB, J=8 Hz).

D. Preparation of 2-(3-Cyclohexylpropyl)-2-ethylpropane-1,3-ditosylate

The title compound was prepared according to the procedure described in Example 13A by replacing 2-(3-cyclohexylpropyl)-propane-1,3-diol with 2-(3-cyclohexylpropyl)-2-ethylpropane-1,3-diol (prepared in Example 12D). The resultant product had the following physical characteristics:

Analysis—NMR(CDCl$_3$): δ0.5–1.8 (22H, multiplet), 2.47 (6H, singlet), 3.85 (4H, singlet), 7.7 ppm (8H, AB, J=10 Hz).

EXAMPLE 14

A. Preparation of 3-(3-Cyclohexylpropyl)-1,1-dicarbethoxycyclobutane

The title compound was prepared according to the procedure of Example 1C by replacing 2-ethylpropane-1,3-ditosylate with 2-(3-cyclohexylpropyl)-propane-1,3-ditosylate (prepared in Example 13A). The resultant product had the following physical characteristics:

Analysis—NMR(CDCl$_3$): δ0.6–2.8 (26H, multiplet), and 4.4 ppm (4H, quartet, J=5 Hz); bp 115° C./0.05 mm.

B. Preparation of 3-(Cyclobutylmethyl)-1,1-dicarbethoxycyclobutane

The title compound was prepared according to Example 14A by replacing 2-(3-cyclohexylpropyl)-propane-1,3-ditosylate with 2-(cyclobutylmethyl)-propane-1,3-ditosylate prepared in Example 13B. The resultant product had the following physical characteristics:

Analysis—NMR(CDCl$_3$): δ0.8–2.9 (20H, multiplet).

C. Preparation of 3-(5-Cyclododecylpentyl)-1,1-dicarbethoxycyclobutane

The title compound was prepared according to Example 14A by replacing 2-(3-cyclohexylpropyl)-propane-1,3-ditosylate with 2-(5-cyclododecylpentyl)-propane-1,3-ditosylate prepared in Example 13C. The resulting product had the following physical characteristics:

Analysis—NMR(CDCl$_3$): δ0.6–2.5 (44H, multiplet), 4.2 ppm (4H, A, J=6 Hz).

D. Preparation of 3-Ethyl-3-(3-cyclohexylpropyl)-1,1-dicarbethoxycyclobutane The title compound was prepared according to the procedure of Example 14A by replacing 2-(3-cyclohexylpropyl)-propane-1,3-ditosylate with 2-ethyl-2-(3-cyclohexylpropyl)-propane-1,3-ditosylate prepared in Example 13D. The resultant product had the following physical characteristics:

Analysis—NMR(CDCl$_3$): δ0.6–2.0 (26H, multiplet), 2.35 (4H, singlet), 4.25 ppm (4H, quartet, J=9 Hz); bp 150°–155° C. C/0.2 mm.

EXAMPLE 15

A. Preparation of 3-(3-Cyclohexylpropyl)-cyclobutane-1,1-dicarboxylic acid

The title compound was prepared according to the procedure of Example 1D by replacing 3-ethyl-1,1-dicarbethoxycyclobutane with 3-(3-cyclohexylpropyl)-1,1-dicarbethoxycyclobutane (prepared in Example 14A). The resultant product had the following physical characteristics:

Analysis—NMR(CDCl$_3$): δ0.6–2.8 (22H, multiplet) and 7.1 ppm (2H, singlet).

B. Preparation of 3-(Cyclobutylmethyl)-cyclobutane-1,1-dicarboxylic acid

The title compound was prepared according to the procedure of Example 15A by replacing 3-(3-cyclohexylpropyl)-1,1-dicarbethoxycyclobutane with 3-(cyclobutylmethyl)-1,1-dicarboethoxycyclobutane (prepared in Example 14B). The resultant product had the following physical characteristics:

Analysis—NMR(CDCl$_3$): δ1.0–3.0 (14H, multiplet) and 8.95 ppm (2H, broad singlet).

C. Preparation of 3-(5-Cyclododecylpentyl)-cyclobutane-1,1-dicarboxylic acid The title compound was prepared according to Example 15A by replacing 3-(3-cyclohexylpropyl)-1,1-dicarboethoxycyclobutane with 3-(5-cyclododecylpentyl)-1,1-dicarboethoxycyclobutane (prepared in Example 14C). The resulting product had the following physical characteristics:

Analysis—NMR(CDCl$_3$): δ0.7–2.8 (38H, multiplet), 8.0 ppm (2H, broad singlet).

D. Preparation of 3-Ethyl-3-(3-cyclohexylpropyl)-cyclobutane-1,1-dicarboxylic acid The title compound was prepared according to Example 15A by replacing 3-(3-cyclohexylpropyl)-1,1-dicarboethoxycyclobutane with 3-ethyl-3-(3-cyclohexylpropyl)-1,1-dicarboethoxycyclobutane (prepared in Example 14D). The resultant product had the following physical characteristics:

Analysis—NMR(CDCl$_3$): δ0.65–0.9 (3H, triplet, J=8 Hz), 0.8–2.0 (22H, multiplet), 2.45 (4H, singlet), 8.25 ppm (2H, broad singlet).

EXAMPLE 16

A. Preparation of 3-(3-Cyclohexylpropyl)-cyclobutanecarboxylic acid

The title compound was prepared according to the procedure of Example 1E by replacing 3-ethylcyclobutane-1,1-dicarboxylic acid with 3-(3-cyclohexylpropyl)-cyclobutane-1,1-dicarboxylic acid (prepared in Example 15A). The resultant product had the following physical characteristics:

Analysis—NMR(CDCl$_3$): δ0.5–3.3 (23H, multiplet) and 11.3 ppm (1H, singlet).

B. Preparation of 3-(Cyclobutylmethyl)-cyclobutanecarboxylic acid

The title compound was prepared according to the procedure of Example 16A by replacing 3-(3-cyclohexylpropyl)-cyclobutane-1,1-dicarboxylic acid with 3-(cyclobutylmethyl)-cyclobutane-1,1-dicarboxylic acid prepared in Example 15B. The resultant product had the following physical characteristics:

Analysis—NMR(CDCl$_3$): δ1.0–2.8 (14H, multiplet), 1.3 (1H, multiplet), 12.5 ppm (1H, broad singlet).

C. Preparation of 3-(5-cyclododecylpentyl)-cyclobutanecarboxylic acid

The title compound was prepared according to the procedure of Example 16A by replacing 3-(3-cyclohexylpropyl)-cyclobutane-1,1-dicarboxylic acid with 3-(5-cyclododecylpentyl)-cyclobutane-1,1-dicarboxylic acid (prepared in Example 15C). The resultant product had the following physical characteristics:

Analysis—NMR(CDCl$_3$): δ0.7–2.5 (39H, multiplet), 10.5 ppm (1H, broad singlet).

D. Preparation of 3-Ethyl-3-(3-cyclohexylpropyl)-cyclobutanecarboxylic acid

The title compound was prepared according to Example 16A by replacing 3-(3-cyclohexylpropyl)-cyclobutane-1,1-dicarboxylic acid with 3-ethyl-3-(3-cyclohexylpropyl)-cyclobutane-1,1-dicarboxylic acid (prepared in Example 15D). The resultant product had the following physical characteristics:

Analysis—NMR(CDCl$_3$): δ0.6–2.6 (27H, multiplet), 11.3 ppm (1H, broad singlet).

EXAMPLE 17

A. Preparation of 3-(3-Cyclohexylpropyl)-cyclobutanecarboxylic acid chloride The title compound was prepared according to the procedure of Example 1F by replacing 3-ethylcyclobutanecarboxylic acid with 3-(3-cyclohexylpropyl)-cyclobutanecarboxylic acid (prepared in Example 16A). The title compound had the following physical characteristics:

Analysis—NMR(CDCl$_3$): δ0.5–3.0 (22H, multiplet) and 3.5 ppm (1H, multiplet).

B. Preparation of 3-(Cyclobutylmethyl)-cyclobutanecarboxylic acid chloride

The title compound was prepared according to Example 17A by replacing 3-(3-cyclohexylpropyl)-cyclobutanecarboxylic acid with 3-(cyclobutylmethyl)-cyclobutanecarboxylic acid (prepared in Example 16B). The resultant product had the following physical characteristics:

Analysis—NMR(CDCl$_3$): δ1.0–2.9 (14H, multiplet) and 3.45 ppm (1H, multiplet).

C. Preparation of 3-(5-Cyclododecylpentyl)-cyclobutanecarboxylic acid chloride The title compound was prepared according to Example 17A by replacing 3-(3-cyclohexylpropyl)-cyclobutanecarboxylic acid with 3-(5-cyclododecylpentyl)-cyclobutanecarboxylic acid (prepared in Example 16C). The resultant product had the following physical characteristics:

Analysis—NMR(CDCl$_3$): δ1.0–3.0 ppm (39H, multiplet).

D. Preparation of 3-Ethyl-3-(3-cyclohexylpropyl)-cyclobutanecarboxylic acid chloride The title compound was prepared according to Example 17A by replacing 3-(3-cyclohexylpropyl)-cyclobutanecarboxylic acid with 3-ethyl-3-(3-cyclohexylpropyl) cyclobutanecarboxylic acid prepared in Example 16D. The resultant product had the following physical characteristics:

Analysis—NMR(CDCl$_3$): δ0.7–2.2 (26H, multiplet) and 3.3 ppm (1H, multiplet).

EXAMPLE 18
A. Preparation of 3-(3-Cyclohexylpropyl)-cyclobutyl-trans-β-chlorovinyl ketone The title compound was prepared according to the procedure of Example 1G by replacing 3-ethylcyclobutanecarboxylic acid chloride with 3-(3-cyclohexylpropyl)-cyclobutanecarboxylic acid chloride (prepared in Example 17A). The resultant product had the following physical characteristics:

Analysis—NMR(CDCl$_3$): δ0.5–2.6 (22H, multiplet), 3.2 (1H, multiplet), 6.4 (1H, doublet, J=12 Hz), 7.2 ppm (1H, doublet, J=12 Hz).

B. Preparation of 3-(Cyclobutylmethyl)-cyclobutyl-trans-β-chlorovinyl ketone The title compound was prepared according to the procedure of Example 19A by replacing 3-(3-cyclohexylpropyl)-cyclobutanecarboxylic acid chloride with 3-(cyclobutylmethyl)-cyclobutanecarboxylic acid chloride prepared in Example 17B. The resultant product had the following physical characteristics:

Analysis—NMR(CDCl$_3$): δ1.0–2.75 (14H, multiplet), 3.25 (1H, multiplet), 6.48 (1H, doublet, J=13 Hz), 7.3 ppm (1H, doublet, J=13 Hz).

C. Preparation of 3-(5-Cylododecylpentyl)-cyclobutyl-trans-β-chlorovinyl ketone The title compound was prepared according to the procedure of Example 18A by replacing 3-(3-cyclohexylpropyl)-cyclobutanecarboxylic acid chloride with 3-(5-cyclododecylpentyl)-cyclobutanecarboxylic acid chloride prepared in Example 17C. The resultant product had the following physical characteristics:

Analysis—NMR(CDCl$_3$): δ0.5–2.7 (40H, multiplet), 6.3 (1H, doublet, J=13 Hz), 7.2 ppm (1H, doublet, J=13 Hz).

D. Preparation of [3-Ethyl-3-(3-cyclohexyl-propyl)-cyclobutyl]-trans-β-chlorovinyl-ketone The title compound was prepared according to the procedure of Example 18A by replacing 3-(3-cyclohexylpropyl)-cyclobutanecarboxylic acid chloride with 3-ethyl-3-(3-cyclohexylpropyl)-cyclobutanecarboxylic acid chloride prepared in Example 17D. The resultant product had the following physical characteristics:

Analysis—NMR(CDCl$_3$): δ0.6–2.4 (26H, multiplet), 3.3 ppm (1H, multiplet), 6.55 (1H, doublet, J=14 Hz), 7.4 ppm (1H, doublet, J=14 Hz).

EXAMPLE 19
A. Preparation of 3-(3-Cyclohexylpropyl)-cyclobutyl-trans-β-iodovinyl ketone The title compound was prepared according to the procedure of Example 1H by replacing 3-ethylcyclobutyl-trans-β-chlorovinyl ketone with 3-(3-cyclohexylpropyl)-cyclobutyl-trans-β-chlorovinyl ketone (prepared in Example 18A). The resultant product had the following physical characteristics:

Analysis—NMR(CDCl$_3$): δ0.6–2.5 (22H, multiplet), 3.3 (1H, multiplet), 7.15 (1H, doublet, J=15 Hz) and 7.75 ppm (1H, doublet, J=15 Hz).

B. Preparation of 3-(Cyclobutylmethyl)-cyclobutyl-trans-β-iodovinyl ketone

The title compound was prepared according to the procedure of Example 19A by replacing 3-(3-cyclohexylpropyl)-cyclobutyl-trans-β-chlorovinyl ketone with 3-(cyclobutylmethyl)-cyclobutyl-trans-β-chlorovinyl ketone prepared in Example 18B. The resultant product had the following physical characteristics:

Analysis—NMR(CDCl$_3$): δ1.0–2.5 (14H, multiplet), 3.2 (1H, multiplet), 7.0 (1H, doublet, J=16 Hz), 7.7 ppm (1H, doublet, J=16 Hz).

C. Preparation of 3-(5-Cylododecylpentyl)-cyclobutyl-trans-β-iodovinyl ketone The title compound was prepared according to the procedure of Example 19A by replacing 3-(3-cyclohexylpropyl)-cyclobutyl-trans-β-chlorovinyl ketone with 3-(5-cyclododecylpentyl)-cyclobutyl-trans-β-chlorovinyl ketone prepared in Example 18C. The resultant product had the following physical characteristics:

Analysis—NMR(CDCl$_3$): δ0.6–2.5 (38H, multiplet), 3.4 (1H, multiplet), 7.2 (1H, doublet, J=13 Hz), 7.7 ppm (1H, doublet, J=13 Hz).

D. Preparation of [3-Ethyl-3-(3-cyclohexylpropyl)-cyclobutyl]-trans-β-iodovinyl ketone The title compound was prepared according to the procedure of Example 19A by replacing 3-(3-cyclohexylpropyl)-cyclobutyl-trans-β-chlorovinyl ketone with [3-ethyl-3-(3-cyclohexylpropyl)-cyclobutyl]-trans-β-chlorovinyl ketone prepared in Example 18D. The resultant product had the following physical characteristics:

Analysis—NMR(CDCl$_3$): δ0.6–2.5 (27H, multiplet), 7.2 (1H, doublet, J=17 Hz), 7.8 ppm (1H, doublet, J=17 Hz).

EXAMPLE 20
A. Preparation of 1-[3-(Cyclohexylpropyl)-cyclobutyl]-trans-3-iodoprop-2-en-1-ol The title compound was prepared according to the procedure of Example 1I by replacing 3-ethylcyclobutyl-trans-β-iodovinyl ketone with 3-(3-cyclohexylpropyl)-cyclobutyl-trans-β-iodovinyl ketone (prepared in Example 19A). The resultant product had the following physical characteristics:

Analysis—NMR(CDCl$_3$): δ0.6–2.5 (22H, multiplet), 3.8–4.3 (2H, multiplet) and 6.1–6.6 ppm (2H, multiplet).

B. Preparation of 1-[3-(Cyclobutylmethyl)-cyclobutyl]-trans-3-iodoprop-2-en-1-ol The title compound was prepared according to the procedure of Example 20A by replacing 3-(3-cyclohexylpropyl)-cyclobutyl-trans-$\beta$-iodovinyl ketone with 3-(cyclobutylmethyl)-cyclobutyl-trans-$\beta$-iodovinyl ketone prepared in Example 19B. The resultant product had the following physical characteristics:

Analysis—NMR(CDCl$_3$): $\delta$1.0–2.9 (15H, multiplet), 4.25 (1H, multiplet), 6.6 ppm (2H, multiplet).

C. Preparation of 1-[3-(5-Cyclododecylpentyl)-cyclobutyl]-trans-3-iodoprop-2-en-1-ol The title compound was prepared according to the procedure of Example 20A by replacing 3-(3-cyclohexylpropyl)-cyclobutyl-trans-$\beta$-iodovinyl ketone with 1-[3-(5-cyclododecylpentyl)-cyclobutyl]-trans-$\beta$-iodovinyl ketone prepared in Example 19D. The resultant product had the following physical characteristics:

Analysis—NMR(CDCl$_3$): $\delta$0.7–2.2 (39H, multiplet), 2.5 (1H, broad singlet), 4.0 (1H, multiplet), 6.1–6.6 ppm (2H, multiplet).

D. Preparation of 1-[3-Ethyl-3-(3-cyclohexylpropyl)-cyclobutyl]-trans-3-iodoprop-2-en-1-ol The title compound was prepared according to the procedure of Example 20A by replacing 3-(3-cyclohexylpropyl)-cyclobutyl-trans-$\beta$-iodovinyl ketone with [3-ethyl-3-(cyclohexylpropyl)-cyclobutyl]-trans-$\beta$-iodovinyl ketone prepared in Example 19D. The resultant product had the following physical characteristics:

Analysis—NMR(CDCl$_3$): $\delta$0.6–2.5 (29H, multiplet), 4.0 (1H, multiplet).

EXAMPLE 21

A. Preparation of 1-[3-(3-Cyclohexylpropyl)-cyclobutyl]-1-(1-ethoxyethoxy)-trans-3-iodoprop-2-ene The title compound was prepared according to the procedure of Example 1J by replacing 1-(3-ethylcyclobutyl)-trans-3-iodoprop-2-en-1-ol with 1-[3-(3-cyclohexylpropyl)-cyclobutyl]-trans-3-iodoprop-2-en-1-ol (prepared in Example 20A). The resultant product had the following physical characteristics:

Analysis—NMR(CDCl$_3$): $\delta$0.6–2.5 (29H, multiplet), 3.65 (3H, multiplet), 4.75 (1H, quartet, J=6Hz) and 6.0–6.7 ppm (2H, multiplet).

B. Preparation of 1-[3-(Cyclobutylmethyl)-cyclobutyl]-1-(1-ethoxyethoxy)-trans-3-iodoprop-2-ene The title compound was prepared according to Example 21A by replacing 1-[3-(3-cyclohexylpropyl)-cyclobutyl]-trans-3-iodoprop-2-en-1-ol with 1-[3-(cyclobutylmethyl)-cyclobutyl]-trans-3-iodoprop-2-en-1-ol (prepared in Example 20B). The resultant product had the following physical characteristics:

Analysis—NMR(CDCl$_3$): $\delta$1.0–2.7 (21H, multiplet), 3.6 (3H, multiplet), 4.7 (1H, quartet, J=6 Hz) 6.1–6.7 ppm (2H, multiplet).

C. Preparation of 1-[3-(5-Cyclododecylpentyl)-cyclobutyl]-1-(1-ethoxyethoxy)-trans-3-iodoprop-2-ene The title compound was prepared according to Example 21A by replacing 1-[3-(3-cyclohexylpropyl)-cyclobutyl]-trans-3-iodoprop-2-en-1-ol with 1-[3-(5-cyclododecylpentyl)-cyclobutyl]-trans-3-iodoprop-2-en-1-ol prepared in Example 20C. The resultant product had the following physical characteristics:

Analysis—NMR(CDCl$_3$): $\delta$0.7–2.3 (45H, multiplet), 3.5 (3H, multiplet), 4.65 (1H, multiplet), 6.0–6.5 ppm (2H, multiplet).

D. Preparation of 1-[3-Ethyl-3-(3-cyclohexylpropyl)-cyclobutyl]-1-(1-ethoxyethoxy)-trans-3-iodoprop-2-ene The title compound was prepared according to Example 21A by replacing 1-[3-(3-cyclohexylpropyl)-cyclobutyl]-trans-3-iodoprop-2-en-1-ol with 1-[3-ethyl-3-(3-cyclohexylpropyl)-cyclobutyl]-trans-3-iodoprop-2-en-1-ol (prepared in Example 20D). The resultant product had the following physical characteristics:

Analysis—NMR(CDCl$_3$): $\delta$0.8–2.5 (33H, multiplet), 3.3–4.1 (3H, multiplet), 4.75 (1H, quartet, J=6 Hz), 6.15–6.8 ppm (2H, multiplet).

EXAMPLE 22

This example illustrates the preparation of 1-(tetrahydropyran-2-yloxy)-7-[3R-(tetrahydropyran-2-yloxy)-5-oxocyclopent-1-enyl] heptane and 1-(tetrahydropyran-2-yloxy)-6-[3RS-(tetrahydropyran-2-yloxy)-5-oxocyclopent-1-enyl] hexane.

A-1 Preparation of Ethyl 9-oxodecanoate ethylene ketal

A solution containing 77.5 g (362 mmol) of ethyl 9-oxodecanoate (prepared described in J. Amer. Chem. Soc., 68: 832 [1946]), 22.4 g (362 mmol) of ethylene glycol and 438 mg of p-toluenesulfonic acid in 150 ml of dry benzene was refluxed for 4.5 hr with a Dean Stark trap. A 7.0 ml portion of water (theoretical=6.5 g) collected in the trap. The solution was cooled to room temperature and then was washed with saturated aqueous sodium bicarbonate. The aqueous phase was back-extracted twice with ether. The combined ether extracts were dried over Na$_2$SO$_4$ and evaporated in vacuo and distilled in vacuo to give a 83.5% yield of the title compound. The product had the following physical characteristics:

Analysis—bp 101°–110° C. (0.2 mm); NMR(CDCl$_3$) $\delta$1.27 (3H, singlet), 1.23 (3H, triplet, J=7 Hz), 1.0 to 2.5 (14H, multiplet), 3.92 (4H, singlet) and 4.13 ppm (2H, quartet, J=7 Hz).

A-2 Preparation of 9-Oxodecan-1-ol

A solution of 95.4 g (370 mmol) of ethyl 9-oxodecanoate ethylene ketal (prepared in Example 22A-1) in 120 ml of ether was added dropwise to a stirred mixture of 10.5 g (277 mmol) of lithium aluminum hydride and 500 ml of ether under argon. The mixture was stirred for 18 hr and then quenched by the dropwise addition of 18 ml of ethyl acetate. To this mixture there was then sequentially added in dropwise fashion, with stirring, 10.5 ml of water, 10.5 ml of 15% aqueous sodium hydroxide and 31.1 ml of water. The mixture was stirred for about 2 to 3 hr and the mixture was then filtered. The filter pad was rinsed several times with ether. The combined filtrates were evaporated in vacuo. The residue was dissolved in a mixture of 250 ml of 10% hydrochloric acid and 120 ml of methanol and left to stand at room temperature for about 4 hr. The solution was evaporated in vacuo. This residue was dissolved in ether and the resulting solution was washed with saturated aqueous sodium chloride, dried over anhydrous magnesium sulfate and evaporated in vacuo to yield 74.3 g of a yellow oil. The product had the following physical characteristics:

Analysis—NMR(CDCl$_3$): δ1.0–2.0(12H, multiplet), 2.12 (3H, singlet), 3.43 (2H, broad triplet, J=7 Hz), 2.9 (1H, broad singlet), 1.15 (3H, doublet, J=6 Hz) and 3.6 ppm (2H, broad triplet, J=Hz).

B-1 Preparation of Oct-7-en-1-ol

A mixture containing 1.7 liter of anhydrous tetrahydrofuran (distilled from sodium/benzophenone ketyl) and 600 g (5.4 mol) of distilled 1,7-octadiene (Aldrich Chemical Co. Inc.) was prepared under nitrogen. Borane in tetrahydrofuran (1 M, 600 ml, 0.60 mol) was added dropwise to the mixture over a 1.0 hr period while the mixture was maintained at 25° C. The resultant solution was stirred for 1 hr at room temperature and then 25 ml of water was added thereto followed by 300 ml of 3 M sodium hydroxide. These additions were followed by 300 ml of 30% aqueous hydrogen peroxide while maintaining the mixture at 30° to 40° C. The mixture was stirred for 15 min and the phases which formed were separated. The aqueous phase was extracted 3 times with an equal volume of pentane. The combined pentane extracts were washed with 200 ml of 10% aqueous sodium bisulfite, then with saturated aqueous sodium chloride and then dried over magnesium sulfate. The mixture was filtered and the filtrate was evaporated and distilled to yield the title compound (bp 62°–64° C., 20 mm) as a colorless oil having the following physical characteristics:

Analysis—NMR(CDCl$_3$): δ1.35 (8H, multiplet), 1.97 (2H, broad triplet), 2.90 (1H, singlet), 3.57 (2H, broad triplet, J=7 Hz), 4.75.2 (2H, multiplet), 5.56.2 ppm (1H, multiplet); IR(CHCl$_3$)ν: 3600, 3250, 3060, 2930, 2850, 1620, 1040, and 900 cm$^{-1}$.

B-2 Preparation of Oct-7-enoic acid

To a stirred solution of 152 g of oct-7-en-1-ol (prepared in Example 22 B-1) in 3.4 liters of acetone there was added 1.4 M of Jones Reagent (986 ml) while the mixture was maintained at less than 10° C. The mixture was stirred for 10 min and was quenched with 100 ml of isopropanol. The acetone volume was reduced in vacuo and the residue was diluted with water and extracted three times with equal volumes of ethyl acetate. The combined ethyl acetate extracts were washed two times with water, then with saturated aqueous sodium chloride, dried over magnesium sulfate and evaporated in vacuo to yield 164 g of the title compound having the following physical characteristics:

Analysis—NMR(CDCl$_3$): δ1.2–1.9 (6H, multiplet), 2.1 (2H, triplet, J=7 Hz), 2.5 (2H, triplet, J=7 Hz), 5.1 (2H, three doublets, J=14,10,2 Hz), 6.0 (1H, two doublets, one quartet, J=14,10,7H); IR(CHCl$_3$)ν: 3600–3000 (broad), 2925, 1705, 1640 and 905 cm$^{-1}$.

B-3 Preparation of Non-8-en-2-one

To a stirred mixture of 11.0 g lithium hydride in 800 ml of anhydrous ether, there was added dropwise 164 g of oct-7-enoic acid (prepared in Example 22 B-2) in 800 ml of anhydrous ether and the mixture was cooled to 0° C. and 650 ml of 2 M methyllithium in ether was added dropwise and then allowed to warm to room temperature and stir for 4.5 hr. This mixture was quenched by pouring the slurry into rapidly stirred 10% aqueous hydrochloric acid (1.2 liter) and wet ice. The resulting mixture was extracted with ether (3×700 ml). The continued ether extracts were washed with 10% aqueous sodium hydroxide and then with saturated aqueous sodium chloride and dried over anhydrous magnesium sulfate. The solvent was removed in vacuo to yield 118.9 g of the title compound having the following physical characteristics:

Analysis—NMR(CDCl$_3$): δ1.2–1.9 (6H, multiplet), 2.1 (2H, triplet, J=7 Hz), 2.2 (3H, singlet), 2.5 (2H, triplet, J=7 Hz), 5.1 (2H, three doublets, J=14,10,2 Hz), 6.0 (1H, two doublets, one quartet, J=14,10,7 Hz); IR(CHCl$_3$)ν: 2925, 1705, 1640, and 905 cm$^{-1}$.

B-4 Preparation of Non-8-en-2-one ethylene ketal

A solution containing 119.0 g of non-8-en-2-one, (prepared in Example 22 B-3), 1.2 g p-toluenesulfonic acid monohydrate, 63.1 g of ethylene glycol and 420 ml anhydrous benzene was prepared and refluxed for about 15 to 17 hr. Water which formed was collected in a Dean-Stark trap. The solution was cooled to room temperature and 250 ml of 5% aqueous sodium bicarbonate solution was added thereto. The benzene layer was separated and dried over anhydrous magnesium sulfate and evaporated in vacuo. The residue was distilled to yield 116.8 g of title compound having the following physical characteristics:

Analysis—bp 80°–85° C. (5 torr); NMR(CDCl$_3$): δ1.3–2.3 (13H, multiplet), 4.0 (4H, singlet), 5.1 (2H, three doublets, J=14,10,2 Hz), 6.0 (1H, two doublets, one quartet, J=14,10,7 Hz); IR(CHCl$_3$)ν: 2925, 1640, 1380, 1060 and 910 cm$^{-1}$.

B-5 Preparation of 8-oxonononan-1-ol-ethylene ketal

A mixture of 320 ml of anhydrous tetrahydrofuran and 58.4 g (0.32 mol) of non-8-en-2-one ethylene ketal prepared in Example 22 B-4) under nitrogen was prepared and 176 ml of 1 M (0.176 mol) of borane in tetrahydrofuran was added thereto over about a 1.0 hr period while maintaining the mixture at about 25° C. Water (7.5 ml) followed by 88 ml of 3 M sodium hydroxide and then 88 ml of 30% aqueous hydrogen peroxide were slowly added while maintaining the temperature at about 30° to 40° C. The resulting mixture was stirred for about 15 min and the phases which formed were separated. The aqueous layer was extracted three times with an equal volume of pentane. The combined pentane extracts were washed with 10% aqueous sodium bisulfite, then with saturated aqueous sodium chloride and then dried over anhydrous magnesium sulfate. The mixture was filtered, evaporated and the residue distilled to yield the title compound having the following physical characteristics:

Analysis—bp 106°–110° C. (5 mm); NMR(CDCl$_3$): δ1.2–2.1 (16H, multiplet), 3.7 (2H, broad triplet, J=6 Hz), and 4.0 ppm (4H, singlet); IR(CHCl$_3$)ν: 3600, 3450 (broad), 2920, 1460, 1375 and 940 cm$^{-1}$.

B-6 Preparation of 8-oxononan-1-ol

A solution containing 56.6 g of 8-oxononan-1-ol ethylene ketol (prepared in Example 22 B-5) in 210 ml acetone and 50 mg p-toluenesulfonic acid monohydrate was stirred at room temperature for about 15 to 17 hr. The acetone was removed in vacuo to yield the title compound having the following physical characteristics:

Analysis—NMR(CDCl$_3$): δ1.2–2.0 (11H, multiplet), 2.2 (3H, singlet), 2.5 (2H, triplet, J=7 Hz), 3.7 (2H, broad triplet, J=6 Hz); IR(CDCl$_3$)ν: 3600 (sharp), 3450 (broad) 2925, 1710, 1260 and 1045 cm$^{-1}$.

C-1 Preparation of 7-(2,3,5-trioxocyclopentyl)-heptan-1-ol

A 4.63 g (201 mmol) portion of sodium was dissolved in 100 ml of dry ethanol under nitrogen. This solution was cooled to 0° C. and stirred as 17.2 g (100 mmol) of 9-oxo-1-decanol (prepared in Example 22 A-2) in 30 ml of diethyloxolate was added dropwise over 25 min. After stirring for 15 hr at room temperature under nitrogen, the resulting solution was refluxed for 1 hr. The solution was then poured into 100 ml of 10% hydrochloric acid and evaporated in vacuo to yield an oil. This oil was refluxed for 5 hr with 600 ml of 2 N hydrochloric acid. The aqueous phase was separated and the remaining oil was extracted with 100 ml of hot 2 N hydrochloric acid. The combined acidic extracts were cooled for about 15 to 17 at 0° C. A crystalline product which formed was collected by filtration, washed with cold water and dried in vacuo over phosphorus pentoxide to yield the title compound having the following physical characteristics:

Analysis—mp 121°-124° C.; NMR(acetone-d$_6$) δ: 1.1–1.8 (12H, multiplet), 2.38 (2H, broad triplet, J=6.5 Hz), 2.86 (2H, singlet) and 3.53 ppm (2H, broad triplet, J=61 Hz); IR(Nujol)ν: 1060, 1170, 1260, 1380, 1435, 1650, 1680, 1730, 2950, 3200 cm$^{-1}$; UV max (CH$_3$OH) 232 μm (ε11,700) and 325 μm (ε11,400); MS(70 eV) m/e 227, 226 (parent), 208, 198, 180, 153, 152, 151, 140, 139, 138, 137, 126 (base), 55, 43 and 41.

C-2 Preparation of 6-(2,3,5-trioxocyclopentyl)-hexan-1-ol

The title compound was prepared using the procedure of Example 9 C-2 by replacing 9-oxodecan-1-ol with 8-oxononan-1-ol (prepared in Example 22 B-6). The product had the following physical characteristics:

Analysis—NMR(acetone-d$_6$) δ:1.1–1.8 (8H, multiplet) 2.4 (2H, broad triplet, J=7 Hz), 3.0 (2H, singlet), 3.6 (2H, broad triplet J=6 Hz), 5.8–6.8(2H, broad, D$_2$O exchangeable); IR(KBr)ν: 3450(broad), 2925, 1740, 1675, 1650, 1440, 1280, 1240, 1060 cm$^{-1}$; UV(methanol): 324 μm (11,600), 232 μm (11,000); MS(70 eV): 212 (parent) 194 (p-H$_2$O), 184, 166, 126 (base peak).

D-1 Preparation of 7-(3R-Hydroxy-2,5-dioxocyclopentyl)-heptan-1-ol

A soybean-glucose medium containing 50 g soybean meal; 20 g glucose; 50 g yeast extract; 50 g K$_2$HPO$_4$; 50 g NaCl; distilled water to 10 l; and pH adjusted to 6.5 with HCl was prepared. The soybean-glucose medium was innoculated with a culture of Dipodascus uninucleatus and 17 g of 7-(2,3,5-trioxocyclopentyl) heptan-1-ol (prepared in Example 9 C-1) was added thereto and incubated at 25° C. for 24 hr. The resultant beer was extracted several times with ethyl acetate. The contained ethyl acetate extracts were dried over Na$_2$SO$_4$ and evaporated in vacuo to yield the title compound having the following physical characteristics:

Analysis—mp 101°-104° C.; NMR(acetone-d$_6$) δ: 1.1–1.8 (10H, broad), 1.8–2.4 (3H, multiplet), 2.75 (1H, d of d, J=17, 6.5 Hz), 3.53 (2H, broad triplet, J=6 Hz), 4.6 (1H, d of d, J=6,2 Hz) and 5.5 ppm (3H, broad singlet); IR (Nujol mull): 1090, 1380, 1465, 1560, 2940 and 3100-3500 cm$^{-1}$ (broad); CD[d]$_{281}$−95, 400° (c 0.85, CHCl$_3$); MS(70 eV)m/e: 228 (p), 210, (p-H$_2$O), 192 (p-2H$_2$O), 182, 169, 155, 128, 110 and other below 100.

E-1 Preparation of 7-(3R-Hydroxy-5-oxocyclopent-1-enyl) heptan-1-ol

To a stirred solution of 228.2 mg (1.0 mmol) of 7-(3R-hydroxy-2,5-dioxocyclopentyl)-heptan-1-ol (prepared in Example 9 D-1) in 3.0 ml of dry tetrahydrofuran at −10° C. under argon, there was added 0.3 ml (2.15 mol) of dry triethylamine and then 218.3 mg (1.0 mol) of 2-mesitylenesulfonyl chloride (Aldrich Chemical Co., Fieser 1,661) in 2 ml of dry tetrahydrofuran. The resulting mixture was stirred at −10° to 0° C. for 40 min and then at room temperature for 1.5 hr. The mixture was diluted with ether, washed with 10% hydrochloric acid, then saturated aqueous sodium chloride and finally saturated aqueous sodium bicarbonate. The extract was dried over anhydrous magnesium sulfate and evaporated in vacuo to yield 0.3828 g of 7-[3R-hydroxy-5-oxo-2-(mesitylenesulfonyloxy)-cyclopent-1-enyl)]-heptan-1-ol. This mesitylenesulfonate in 6 ml of dry tetrahydrofuran was then added dropwise to a stirred solution of 1.15 g (4.0 mol) of Red-Al ® (Aldrich Chemical Co., 70% solution of sodium bis-(2-methoxyethoxy)-aluminum hydride in benzene; Fieser 2,382;3,260) in 3 ml of dry tetrahydrofuran under argon at −78° C. The resultant solution was stirred for 1.5 hr and then quenched by addition of 1.5 ml of acetic acid. The mixture was diluted with ether and shaken with several ml of 10% hydrochloric acid until all solids had dissolved. The organic phase was separated and washed with saturated aqueous sodium chloride. The combined wash solution was back-extracted twice with ether. The combined ether extracts were washed with aqueous sodium bicarbonate, dried over anhydrous magnesium sulfate, and evaporated in vacuo to yield 7-[4R,5RS-dihydroxy-2-(mesitylenesulfonyloxy)-cyclopent-1-enyl)]-heptan-1-ol as a clear oil. This oil was dissolved in 5 ml of chloroform and stirred under argon with 85 mg of sodium oxalate and 36 mg of oxalic acid (hydrate). After 2 hr, the mixture was washed with saturated aqueous sodium bicarbonate. The wash solution was back-extracted twice with chloroform. The combined chloroform extracts were dried over Na$_2$SO$_4$ and evaporated in vacuo to yield 0.2114 g of the crude title compound which was purified by preparative thin layer chromatography. The pure title compound had the following physical characteristics:

Analysis—mp 62°-64° C.; NMR(CDCl$_3$): δ0.8–1.9 (10H, broad multiplet), 2.2 (2H, broad multiplet), 2.26 (1H, d of d, J=2.5, 19 Hz), 2.82 (1H, d of d, J=6, 19 Hz), 3.6 (2H, broad triplet, J=6 Hz), 4.03 (2H, singlet), 4.9 (1H, multiplet) and 7.2 ppm (1H, broad singlet); IR(CHCl$_3$)ν: 1030, 1710, 2860, 2930, 3005, 3200-3550 (broad) and 3600 cm$^{-1}$; UVmax(CH$_3$OH) 223 μm (ε8,300); Mass Spectrum (70 eV)m/e 213, 212 (parent), 194, 168, 149, 135, 122, 95, 82, 81, 69, 67, 55, 43 (base) and 41. [α]$_D^{25}$+17.2° (c 0.53, CH$_3$OH), +12.7 (c 1.09, CHCl$_3$).

E-2. Preparation of 6-(3RS-Hydroxy-5-oxocyclopent-1-enyl) hexan-1-ol

The title compound was prepared using the procedure of Example 9 E-1 by replacing 7-(3R-hydroxy-2,5-dioxocyclopentyl) heptan-1-ol with 6-(3RS-hydroxy-2,5-dioxocyclopentyl) hexan-1-ol (prepared in Example 21 D-2). The product had the following physical characteristics:

Analysis—NMR(CDCl$_3$): δ1.2–2.0 (8H, multiplet), 2.0–2.6 (2H, multiplet), 2.75 (1H, doublet, J=5.5 Hz), 3.1 (1H, doublet, J=5.5 Hz), 3.4 (2H, broad singlet, D$_2$O exchangeable), 3.7 (2H, broad triplet, J=6 Hz), 5.05 (1H, multiplet), 7.35 (1H, multiplet); IR(CHCl$_3$)ν: 3600 (sharp), 3550-3100 (broad), 2930, 1710, 1210, 1030, 945 cm$^{-1}$; Mass Spectrum (70 eV): 198 (parent), 180 (p±H$_2$O), 168, 154, 149, 95, 85 (base peak).

F-1. Preparation of 1-(Tetrahydropyran-2-yloxy)-7-[3R-(tetrahydropyran-2-yloxy)-5-oxocyclopent-1-enyl] heptane A mixture of 338 mg (1.59 mmol) of 7-(3R-hydroxy-5-oxocyclopent-1-enyl)-heptan-1-ol (prepared in Example 9 E-1); 0.775 ml (8.5 mol) of freshly distilled dihydropyran and 5 mg of toluenesulfonic acid in 5 ml of ether was stirred at room temperature under nitrogen for about 3 hr. The mixture was diluted with ether and washed with a small portion of aqueous sodium bicarbonate. The ether solution was dried over Na$_2$SO$_4$ and evaporated in vacuo to yield the title compound having the following physical characteristics:

Analysis—NMR(CDCl$_3$): δ1.0 to 2.8 (26H, broad multiplet), 3.2 to 4.2 (6H, multiplet), 4.5 to 5.1 (3H, multiplet) and 7.2 ppm (H, broad singlet).

F-2. Preparation of 1-(Tetrahydropyran-2-yloxy)-6-[3RS-(tetrahydropyran-2-yloxy)-5-oxocyclopent-1-enyl] hexane.

The title compound was prepared according to the procedure of Example 9 F-1 by replacing 7-(3R-hydroxy-5-oxocyclopent-1-enyl)heptan-1-al with 6-(3RS-hydroxy-5-oxocyclopent-1-enyl)hexan-1-ol (prepared in Example 21 E-2). The product had the following physical characteristics:

Analysis—NMR(CDCl$_3$): δ1.2–2.0 (20H, multiplet), 2.1–2.4 (2H, multiplet), 2.5–3.0 (2H, H$_A$H$_B$ of ABX pattern), 3.4–4.3 (6H, multiplet) 4.7 (1H, multiplet), 5.0 (2H, multiplet), 7.4 (1H, multiplet); IR(CHCl$_3$)ν: 2930, 1710, 1640, 1340, 1120, 1075, 1020, 980, 900, 860 cm$^{-1}$.

EXAMPLE 23

This example illustrates the preparation of:
A. 16,18-Methano-1,11α,15S-trihydroxyprost-13E-en-9-one (TR-4570); and
B. 16,18-Methano-1,11α,15R-trihydroxyprost-13E-en-9-one (TR-4569).

A solution of 2.54 g (7.5 mol) of 1-iodo-3-(1-ethoxyethoxy)-3-(3-ethylcyclobutyl)-1E-propane prepared in Example 1-J in 15 ml of dry ether was stirred under argon with dry ice-acetone bath cooling as 10.4 ml (15.0 mol) of a solution of t-butyllithium in pentane (1.44 M) was added dropwise over 2 min and stirred for 2 hr at −78° C.

A second solution was prepared by stirring a dispersion of 1.96 g (15 mol) of copper(I) pentyne in 25 ml of dry ether with 6.0 ml of hexamethylphosphorus triamide under argon until the solution becomes homogeneous. One half of the resulting solution was then transferred via syringe to the above alkenyllithium solution as it was stirred at −78° C.

After 45 min, a third solution of 1.90 g (5.0 mol) of 1-(tetrahydropyran-2-yloxy)-7-[3R-(tetrahydropyran-2-yloxy)-5-oxocyclopent-1-enyl]heptane (prepared in Example 22-F-1) in 5 ml of ether was added dropwise to the above alkenyl copper solution as it was stirred at −78° C. The resultant dispersion was stirred at −78° C. for 1.5 hr, then it was warmed over a 1 hr period to −20° C. and stirred at −20° C. for 2 hr.

The resultant mixture was quenched by the addition of 200 ml of 2% aqueous sulfuric acid. The resultant slurry was mixed thoroughly and then filtered through Celite (diatomaceous earth). The phases which formed in the filtrate were separated and the ether phase was washed with saturated aqueous sodium chloride and then with saturated aqueous sodium bicarbonate. The washed ether phase was dried over anhydrous magnesium sulfate and evaporated in vacuo to yield an oily residue. The oily residue was mixed with 45 ml of (65:35 V/V) acetic acid-water and 5 ml of tetrahydrofuran and stirred under argon for 45 hr at room temperature. The solvents were removed by evaporation in vacuo to give 2.56 g of a yellow residue. This residue was chromatographed on silicic acid-Celite (diatomaceous earth) (85:15) using benzene to ethyl acetate gradient elution to yield 324 mg of title compound TR-4570 above and 327 mg of title compound TR-4569. An earlier cut of less polar components (containing tetrahydropyranyl protected forms of TR-4570 and TR-4569) was separated and used as the starting material in Example 28 below.

A. Title compound TR-4570 had the following physical characteristics:

Analysis—NMR(CDCl$_3$): δ0.80 (3H, broad triplet, J=6.5 Hz): 1.0–2.7 (24H, multiplet), 3.2 (3H, broad singlet), 3.64 (2H, broad triplet, J=5.5 Hz), 4.02 (2H, multiplet) and 5.75 ppm (2H, multiplet); IR(film)ν: 970, 1080, 1160, 1460, 1735, 2860, 2930 and 3100 to 3600 cm$^{-1}$ (broad); Mass spectrum (70 eV)m/e: 334 (p-H$_2$O), 316 (p-2H$_2$O), 369 (p-($_6$H$_{11}$), 351 (p-H$_2$O-($_6$H$_{11}$), 234 (p-H$_2$O-HO-($_6$H$_{11}$); Optical Rotation: [α]$_D$−61° (c 1.0, CHCl$_3$).

B. Title compound TR-4569 had the following physical characteristics:

Analysis—NMR(CDCl$_3$): δ0.80 (3H, broad triplet, J=6.5 Hz), 1.0–2.7 (24H, multiplet), 3.4 to 4.2 (7H, multiplet) and 5.61 ppm (2H, multiplet); Optical Rotation [α]$_D$−41.5° C. (c 1.0, CHCl$_3$).

EXAMPLE 24

This example illustrates the preparation of:
A. 16,18-Methano-16-methyl-1,11α,15S-trihydroxyprost-13E-en-9-one (TR-4689); and
B. 16,18-Methano-16-methyl-1,11α,15R-trihydroxyprost-13E-en-9-onc (TR-4688).

Repeating in a similar manner the procedure of Example 23, but replacing 1-iodo-3-(1-ethoxyethoxy)-3-(3-ethyl-cyclobutyl)-1E-propene with 1-iodo-3-(1-ethoxyethoxy)-3-(3-ethyl-1-methylcyclobutyl) 1E-propene (prepared in Example 7-A) yields title compound TR-4689 and title compound TR-4688.

A. Title compound TR-4589 had the following physical characteristics:

Analysis—NMR(CDCl$_3$): δ0.80 (3H, broad triplet, J=6.5 Hz) 1.07 and 1.13 (3H total, two singlets for methyl on isomers at C-16), 1.0 to 3.0 (23H, multiplet), 2.72 (3H, broad singlet), 3.67 (2H, broad triplet, J=5.5 Hz), 3.9–4.3 (2H, multiplet) and 5.80 ppm (2H, multiplet); IR(CHCl$_3$)ν: 970, 1070, 1380, 1465, 1740, 2860, 2940, 3200 to 3600 cm$^{-1}$ (broad); Mass Spectrum (70 eV)m/e: 348 (p-H$_2$O), 330 (p-2H$_2$O), 276, 268 (p-C$_7$H$_{14}$); Optical Rotation: [α]$_D$−64.3° (c 0.96, CHCl$_3$).

B. Title compound TR4688 had the following physical characteristics:

Analysis—NMR,IR and Mass Spectrum similar to title compound TR-4689 above; Optical Rotation [α]−50.1° (c 0.98, CHCl₃).

EXAMPLE 25

This example illustrates the preparation of:
A. 16,19-Cyclo-16-methyl-20-nor-1,11α,15S-trihydroxyprost-13E-en-9-one (TR-4674); and
B. 16,19-Cyclo-16-methyl-20-nor-1,11α,15R-trihydroxyprost-13E-en-9-one (TR-4673).

Repeating in a similar manner the procedure of Example 23, but replacing 1-iodo-3-(1-ethoxyethoxy)-3-(3-ethylcyclobutyl)-1E-propene with 1-iodo-3-(1-ethoxyethoxy)-3-(1-methylcyclobutyl)-1E-propene (prepared in Example 7-B) yields title compound TR-4674 and title compound TR-4673.

A title compound TR-4674 had the following physical characteristics:

Analysis—NMR(CDCl₃): δ1.14 (3H, singlet), 1.0–3.0 (22H, multiplet), 2.9 (3H, broad singlet), 3.67 (2H, broad triplet, J=5.5 Hz), 4.15 (2H, multiplet) and 5.82 ppm (2H, multiplet); IR(CHCl₃)ν: 970, 1070, 1220, 1740, 2860, 2930 and 3200 to 3600 cm⁻¹ (broad); Mass Spectrum (70 eV)m/e: 3.20 (p-H₂O), 302 (p-2H₂O-C₅H₉); Optical Rotation: [α]$_D$−61.7° (c 1.0, CHCl₃).

B. Title compound TR-4673 had the following physical characteristics:

Analysis—NMR, IR, and Mass Spectrum similar to title compound TR-4674 above; Optical Rotation: [α]$_D$−55° (c 1.0, CHCl₃).

EXAMPLE 26

This example illustrates the preparation of:
A. 16,16-Propano-1,11α,15S-trihydroxyprost-13E-en-9-one (TR-4646); and
B. 16,16-Propano-1,11α,15R-trihydroxyprost-13E-en-9-one (TR-4645).

Repeating in a similar manner the procedure of Example 23, but replacing 1-iodo-3-(1-ethoxyethoxy)-3-(3-ethylcyclobutyl)-1E-propene with 1-iodo-3-(1-ethoxyethoxy)-3-(1-butylcyclobutyl)-1E propene (prepared in Example 7-C) yields title compound TR-4646 and title compound TR-4645.

A title compound TR-4646 had the following physical characteristics:

Analysis—NMR(CDCl₃): δ0.80 (3H, broad triplet, J=6.5 Hz), 1.0 to 2.8 (20H, multiplet), 3.68 (2H, broad triplet, J=5.5 Hz), 4.2 (2H, multiplet) and 5.83 ppm (2H, multiplet); IR(CHCl₃)ν: 970, 1070, 1740, 2860, 2930, and 3200 to 3600 cm⁻¹ (broad); Mass Spectrum (70 eV)m/e: 390 (p-H₂O), 297 (p-C₈H₁₅); Optical Rotation: [α]$_D$−52.9° (c 1.09, CHCl₃).

B. Title compound TR-4645 had the following physical characteristics:

Analysis—NMR, IR and Mass Spectrum similar to title compound TR-4646 above; Optical Rotation: [α]$_D$−77.4° (c 0.78, CHCl₃).

EXAMPLE 27

This example illustrates tthe preparation of:
A. (±)16,18-Methano-1-nor-2,11α,15S-trihydroxyprost-13E-en-9-one (TR-4676); and
B. (±)16,18-Methano-1-nor-2,11α,15R-trihydroxyprost-13E-en-9-one (TR-4675).

Repeating in a similar manner the procedure of Example 23, but respectively replacing 1-(tetrahydropyran-2-yloxy)-7-[3R-(tetrahydropyran-2-yloxy)-5-oxocyclopent-1-enyl]heptane with 1-(tetrahydropyran-2-yloxy)-6-[3RS-(tetrahydropyran-2-yloxy)-5-oxocyclopent-1-enyl] hexane (prepared in Example 22 F-2) to yield the title compounds TR-4676 and TR-4675.

A Title compound TR-4676 had the following physical characteristics:

Analysis—NMR(CDCl₃): δ0.9 (3H, triplet, J=6 Hz), 1.1–2.8 (25H, multiplet), 3.65 (2H, triplet, J=6 Hz), 3.9–4.5 (2H, multiplet), 5.75 (2H, multiplet); IR(CHCl₃)ν: 3600 (sharp), 3380 (broad), 2925, 1730, 1450, 1065, 965 cm⁻¹; Mass Spectrum (70 eV)m/e: no parent (338), 320 (p-H₂O), 264 (p-C₄H₁₀O), 251, 249, 237, 220, 121, 83, 49 (base peak); R$_f$=0.29. (system II).

B. Title compound TR4675 had the following physical characteristics:

Analysis—NMR, IR and Mass Spectrum similar to title compound TR-4676 above; R$_f$=0.24 (system II).

EXAMPLE 28

This example illustrates the preparation of:
A. 1-Acetoxy-15S-hydroxy-16,18-methanoprosta-10,13E-dien-9-one (TR-4565); and
B. 1-Acetoxy-15R-hydroxy-16,18-methanoprosta-10,13E-dien-9-one (TR-4568).

The mixture of partially protected forms of title compounds TR-4570 and TR-4569 separated in Example 23 above was stirred with 25 ml of acetic acid-water tetrahydrofuran (65:35:10 V/V/V) under argon at 60° C. for 18 hr. The solvent was removed by evaporation in vacuo. The residue was dissolved in ethyl acetate and washed with aqueous sodium bicarbonate. The resultant organic solution was dried over anhydrous magnesium sulfate and the solvent evaporated in vacuo. The residue was chromatographed on silicic acid-Celite (85:15) using a benzene to ethyl acetate gradient elution to yield the title compounds.

A. Title compound TR-4565 had the following physical characteristics:

Analysis—NMR(CDCl₃): δ0.80 (3H, broad triplet, J=6.5 Hz), 1.0–2.3 (22H, multiplet), 2.07 (3H, singlet), 3.30 (1H, broad singlet), 4.12 (2H, broad triplet, J=6.0 Hz), 3.8 (1H, multiplet), 5.68 (2H, multiplet), 6.23 (1H, d of d, J6 Hz, 2.5 Hz), and 7.6 ppm (1H, d of d, J=6 Hz, 2.5 Hz); IR(film)ν: 970, 1040, 1240, 1370, 1465, 1595, 1710, 1740, 2870, 2980, and 3200 to 3600 cm⁻¹ (broad); Mass Spectrum (70 eV)m/e: 376 (strong p), 358 (p-H₂O), 348, 334 (p-C₂H₃O), 316 (p-C₂H₃o-H₂0), 293 (p-C₆H₁₁), 351 (p-C₆H₁₆-C₂H₃O); Optical Rotation: [α]$_D$+89° (c 1.0, CHCl₃).

B. Title compound TR-4568 had the following physical characteristics:

Analysis—NMR, IR and Mass Spectrum similar to TR-4565 above; Optical Rotation [α]$_D$+100.3 (c 1.0, CHCl₃).

EXAMPLE 29

This example illustrates the preparation of:
A. 16,18-Methanoprost-13E-en-1,9α,11α,15S-tetraol (TR-4626); and
B. 16,18-Methanoprost-13E-en-1,9β,11α,15S-tetraol (TR-4627).

A solution of 1-iodo-3-(1-ethoxyethoxy)-3-(3-ethylcyclobutyl)-1E-propene (2.194 g, 6.49 mmole; prepared in Example 1-J) in 50 ml of dry ether (distilled from sodium benzophenone ketyl) was prepared and cooled to −78° C. To this solution there was added 7.29 ml of 1.78 M (12.98 mol) t-butyllithium in pentane and the mixture was stirred for 2 hr at −78° C. Copper (I) pentyne (1.844 g, 6.49 mol) was slurried in 50 ml of dry ether and 2.24 ml of dry hexamethylphosphorus triamide was added and the mixture was stirred for 30 min and then cooled to −78° C. To this copper reagent solution there was then added the previously prepared organolithium solution. A solution of methyl 7-[3α-(tetrahydropyran-2-yloxy)-5-oxocyclopent-1-enyl] heptanoate (2.034 g, 6.2 mol; preparation described in *J. Amer. Chem. Soc.*, 95:1696[1973]) in 4 ml of dry ether was slowly added to the lithium dialkenyl cuprate solution prepared above. The resultant mixture was stirred for 30 min at −78° C., then for 90 min at −20° C. and then the mixture was quenched with 20% aqueous ammonium sulfate solution. This mixture was shaken for 10 min and the phases which formed were separated. The aqueous phase was extracted with 100 ml (2×50 ml) of ether. The organic phase was shaken with cold 2% aqueous sulfuric acid. This acidified organic phase was then extracted with 100 ml (2×50 ml) of ether. The combined ether extracts were filtered through Celite (diatomaceous earth). The filtrate was washed with 50 ml of saturated sodium bicarbonate solution and then with 50 ml of saturated aqueous sodium chloride solution. The washed extract was dried over anhydrous magnesium sulfate and the solvent was removed by evaporation in vacuo. The residue was stirred with 25 ml of acetic acid-water tetrahydrofuran (65:35:10 V/V/V) for 18 hr at room temperature. The solvents were removed in vacuo and the residue was taken up in 30 ml of water and 30 ml of ether-ethyl acetate (1:1 V/V). The aqueous material was separated and extracted with 60 ml (2×30 ml) of ether-ethyl acetate (1:1 V/V). This extract and the separated organic material were combined and the mixture was washed with 30 ml of saturated aqueous sodium bicarbonate and then with 30 ml of saturated sodium chloride. The washed material was then dried over anhydrous magnesium sulfate and the solvent was removed by evaporation in vacuo. The residue was chromatographed on silicic acid-Celite (85:15 W/W) using a benzene-ethyl acetate gradient elution and the 15R-PGE$_1$ isomer was separated (Optical Rotation: $[\alpha]_D$−39.8° [c1.0, CHCl$_3$]). A solution containing 466 mg of this separated isomer in 25 ml of methanol was prepared and stirred with ice-bath cooling as 700 mg of sodium borohydride was added over 15 min. The resultant mixture was stirred with ice-bath cooling for 0.5 hr and then without cooling for 0.5 hr. Water was added to this reaction mixture and the solvents were removed by evaporation in vacuo. The residue was chromatographed on silicic acid-Celite (85:15) to yield the title compounds.

A. Title compound TR-4626 had the following physical characteristics:

Analysis—NMR(CDCl$_3$): δ0.95 (3H, broad triplet, J=6.5 Hz), 1.0 to 2.5 (24H,, multiplet), 2.7 (4H, broad singlet), 3.77 (2H, broad triplet, J=6 Hz), 4.02 (2H, broad multiplet), 4.23 (1H, broad multiplet) and 5.62 (2H, multiplet); IR(CHCl$_3$)ν: 2860, 2930 and 3200 to 3600 cm$^{-1}$ (broad); Mass Spectrum (70 eV)m/e: 336 (p-H$_2$O), 318 (p-2H$_2$O), 387, 292, 271 (p-C$_6$H$_{11}$), 264, 253 (p-C$_6$H$_{11}$-H$_2$O); Optical Rotation: $[\alpha]_D$+8.5 (c 1.0, CHCl$_3$).

B. Title compound TR-4627 had the following physical characteristics:

Analysis—NMR(CDCl$_3$), IR(CHCl$_3$) and Mass Spectrum similar to TR-4626 above; Optical Rotation: $[\alpha]_D$−23.4° C. (c 1.0, CHCl$_3$).

EXAMPLE 30

This example illustrates the preparation of:

A. Methyl 11α,15R-dihydroxy-16,18-methano-9-oxoprost-13E-en-1-oate (TR-4248); and B. Methyl 11α,15S-dihydroxy-16,18-methano-9-oxoprost-13E-en-1-oate (TR-4249).

A first solution containing (2.194 g, 6.49 mol) of 1-iodo-3-(1-ethoxyethoxy)-3-(3-ethylcyclobutyl)-1E-propene (prepared in Example 1 J) in 50 ml of dry ether (distilled from sodium benzophenone ketyl) was prepared and cooled to −78° C. To this solution there was added 7.29 ml (12.98 mol, ... 78 M) of t-butyllithium in pentane and the resulting mixture was stirred for 2 hr at −78° C. A second solution containing 0.844 g (6.49 mol) of copper (I) pentyne in 50 ml of dry ether and 2.24 ml of dry hexamethylphosphorus triamide was prepared, stirred for 30 min and cooled to −78° C. The second solution was then added to the first solution. A third solution containing 2.035 g (6.2 mol) of methyl 7-[3α-tetrahydropyran-2-yloxy)-5oxocyclopent-1enyl] heptanoate (preparation described in *J. Amer. Chem. Soc.*, 95:1676 [1973]), in 4 ml of dry ether was prepared and added to the above mixture of the first and second solutions. The resulting mixture was stirred for 30 min at −78° C., then 90 min at −20° C. and then quenched with 20% aqueous ammonium sulfate solution. This mixture was shaken for 10 min and the phases were separated. The aqueous phase was extracted with 100 ml (2×50 ml) of ether. The organic phase was shaken with cold 2% aqueous sulfuric acid and the aqueous layer was then extracted with 100 ml (2×50 ml) of ether. The organic extracts were combined and filtered through Celite (diatomaceous earth), washed with 50 ml of saturated aqueous sodium bicarbonate solution and then with 50 ml of saturated aqueous sodium chloride solution. The washed extract was dried over anhydrous magnesium sulfate and the solvent was removed by evaporation in vacuo. The residue was stirred for 18 hr with 25 ml of acetic acid-water-tetrahydrofuran (65:35:10, V/V/V) at room temperature. The solvents were removed in vacuo and the residue was taken up in 30 ml of water and 30 ml of ether-ethyl acetate. The aqueous material was extracted with 60 ml (2×30 ml) of ether-ethyl acetate. The ether-ethyl acetate extract was washed with 30 ml of saturated aqueous sodium bicarbonate and then with 30 ml of saturated aqueous sodium chloride. The wash extract was dried over anhydrous magnesium sulfate and the solvent was removed by evaporation in vacuo. The residue was chromatographed on silicic acid-Celite (85:15 W/W) using a benzene-ethyl acetate gradient elution to yield the title compound TR-4249 and TR-4248.

A. Title compound TR-4248 had the following physical characteristics:

Analysis—NMR(CDCl$_3$): δ0.8 (3H, triplet, J=6 Hz), 1.0-2.9 (24H, multiplet), 3.65 (3H, singlet), 3.8-4.3 (4H, multiplet) and 5.65 ppm (2H, multiplet; IR(CHCl$_3$)ν: 3600-3100, 2950, 1740 cm$^{-1}$; $[\alpha]_D$−39.8° (c 1.0, CHCl$_3$).

B. Title compound TR-4249 had the following physical characteristics:

Analysis—NMR(CHCl$_3$): δ0.8 (3H, triplet, J=6 Hz), 1.0-3.3 (24H, multiplet), 3.65 (3H, singlet), 3.65-4.2 (4H, multiplet) and 5.6 ppm (2H, multiplet); IR(CHCl$_3$)ν: 3600-3100, 2950, 1740 cm$^{-1}$; $[\alpha]_D$−49.6° (c 0.96, CHCl$_3$).

EXAMPLE 31

This example illustrates the preparation of:
A. Methyl 11α,15S-dihydroxy-16,18-methano-16-methyl-9-oxoprost-13E-en-1-oate (TR-4682); and
B. Methyl 11α,15R-dihydroxy-16,18-methano-16-methyl-9-oxoprost-13E-en-1-oate (TR-4681).

Repeating in a similar manner the procedure of Example 30 but replacing 1-iodo-3-(1-ethoxyethoxy)-3-(3-ethylcyclobutyl)-1E-propene with 1-iodo-3-(1-ethoxyethoxy)-3-(3-ethyl-1-methylcyclobutyl)-1E-propene (prepared in Example 8A) yield the above title compounds.

A. Title compound TR-4682 had the following physical characteristics:

Analysis—NMR(CDCl$_3$): δ0.8 (3H, broad triplet, J=6.5 Hz), 1.03 and 1.11 (3H, total, two singlets, isomeric methyl on C-16), 1.0 to 3.3 (23H, multiplet), 3.70 (3H, singlet), 4.02 (3H, multiplet), 4.23 (1H, multiplet), and 5.80 (2H, multiplet); IR(CHCl$_3$)ν: 970, 1075, 1165, 1230, 1740, 2860, 2930, 2960 and 3200 to 3600 cm$^{-1}$; Mass Spectrum (70 eV)m/e: 376 (p-H$_2$O), 358 (p-2H$_2$O), 345 (p-H$_2$O-CH$_3$O), 327 (p-2H$_2$O-CH$_3$O), 297 (p-C$_7$H$_{13}$), 279 (p-H$_2$O-C$_7$H$_{13}$); Optical Rotation: [α]$_D$−65.9° (c 1.0, CHCl$_3$).

B. Title compound TR-4681 had the following physical characteristics:

Analysis—NMR, IR and Mass Spectrum similar to title compound TR-4682 above; Optical Rotation: [α]$_D$−54.3° (c 0.81, CHCl$_3$).

EXAMPLE 32

This example illustrates the preparation of:
A. Methyl 16,19-cyclo-11α,15S-dihydroxy-16-methyl-20-nor-9-oxoprost-13E-en-1-oate (TR-4691); and
B. Methyl 16,19-cyclo-11α,15R-dihydroxy-16-methyl-20-nor-9-oxoprost-13E-en-1-oate (TR-4690).

Repeating in a similar manner the procedure of Example 32, but replacing 1-iodo-3-(1-ethoxyethoxy)-3-(3-ethylcyclobutyl)-1E-propene with 1-iodo-3-(1-ethoxyethoxy)-3-(1-methylcyclobutyl)-1E-propene (prepared in Example 8B) yields the above title compounds.

A. Title compound TR-4691 had the following physical characteristics:

Analysis—NMR(CDCl$_3$): δ1.13 (3H, singlet), 1.0 to 3.3 (22H, multiplet), 3.73 (3H, singlet), 4.2 (4H, multiplet), and 5.83 ppm (2H, multiplet); IR(CHCl$_3$)ν: 975, 1080, 1170, 1230, 1440, 1740, 2870, 2950 and 3200 to 3600 cm$^{-1}$ (broad); Mass Spectrum (70 e/V)m/e: 348 (p-H$_2$O), 330 (p-2H$_2$O), 316 (p-H$_2$O-CH$_3$OH), 299 (p-2H$_2$O-CH$_3$O), 297 (p-C$_5$H$_9$), 279 (p-H$_2$O-C$_5$H$_9$); Optical Rotation: [α]$_D$−65.5° (c 1.10, CHCl$_3$).

B. Title compound TR-4690 had the following physical characteristics:

Analysis—NMR, IR and Mass Spectrum similar to title compound TR-4691 above; Optical Rotation [α]$_D$−50.4° (c 1.39, CHCl$_3$).

EXAMPLE 33

This example illustrates the preparation of:
A. Methyl 11α,15S-dihydroxy-9-oxo-16-,16-propanoprost-13E-en-1-oate (TR-4677); and
B. Methyl 11α,15R-dihydroxy-9-oxo-16,16-propanoprost-13E-en-1-oate (TR-4692).

Repeating in a similar manner the procedure of Example 32, but replacing 1-iodo-3-(1-ethoxyethoxy)-3-(3-ethylcyclobutyl)-1E-propene with 1-iodo-3-(1-ethoxyethoxy)-3-(1-butylcyclobutyl)-1E-propene (prepared in Example 8C) yields the above title compounds.

A. Title compound TR-4677 had the following physical characteristics:

Analysis—NMR(CDCl$_3$): α0.8 (3H, broad triplet, J=6.5 Hz), 1.0–3.2 (28H, multiplet), 3.71 (3H, singlet), 4.18 (4H, multiplet) and 5.83 ppm (2H, multiplet); IR(CHCl$_3$)ν: 970, 1070, 1160, 1230, 1440, 1740, 2860, 2930 and 3200 to 3600 cm$^{-1}$ (broad); Mass Spectrum (70 eV)m/e: 390 (p-H$_2$O), 372 (p-2H$_2$O), 341 (p-2H$_2$O-OMe), 319, 297 (p-C$_8$H$_{15}$), 280, 279, 265, 247, 191, 99, 69 (base peak, C$_5$H$_9$); Optical Rotation [α]$_D$−82.1° (c 1.15, CHCl$_3$).

B. Title compound TR-4692 had the following physical characteristics:

Analysis—NMR, IR and Mass Spectrum similar to title compound TR-4677 above; Optical Rotation: [α]$_D$−61.3° (c 1.13, CHCl$_3$).

EXAMPLE 34

This example illustrates the preparation of:
A. Methyl 15RS-hydroxy-16,18-methano-9-oxoprosta-10,13E-dien-1-oate (TR-4280); and
B. Methyl 15RS-acetoxy-16,18-methano-9-oxoprosta-10,13E-dien-1-oate (TR-4281).

A solution of 1-iodo-3-(1-ethoxyethoxy)-3-(3-ethylcyclobutyl)-1E-propene (prepared in Example 1J) (2.194 g, 6.49 mol) in 50 ml of dry ether (distilled from sodium benzophenone ketyl) was prepared and cooled to −78° C. To this solution, there was added t-butyllithium in pentane (7.29 ml, 12.98 mmol, 1.78 M) and the mixture was stirred for 2 hr at −78° C. Copper(I) pentyne (0.844 g, 6.49 mmol) was slurried in 50 ml of dry ether and 2.24 ml of dry hexamethylphosphorus triamide was added and the mixture was stirred for 30 min and then cooled to −78° C. The organolithium solution was then added to this copper reagent solution. A solution of methyl 7-[3α-(tetrahydropyran-2-yloxy)-5-oxocyclopent-1-enyl] heptanoate (preparation described in J. Amer. Chem. Soc., 95:1676 [1973]) (2.035 g, 6.2 mmol) in 4 ml of dry ether was slowly added to the lithium dialkenyl cuprate solution and the resulting mixture was stirred for 30 min at −78° C., 90 min at −20° C. and then was quenched with 20% aqueous ammonium sulfate solution. The mixture was shaken for 10 min and the phases which formed were separated. The aqueous phase was extracted with 100 ml (2×50 ml of ether. The organic phase was shaken with cold 2% aqueous sulfuric acid. This acidic aqueous phase was then extracted with 100 ml (2×50 ml) of ether. The ether extracts were combined and filtered through Celite (diatomaceous earth). The filtrate was washed with 50 ml of saturated sodium bicarbonate solution and then with 50 ml of saturated aqueous sodium chloride solution. The washed extract was dried over anhydrous magnesium sulfate and the solvent was removed by evaporation in vacuo. The residue was stirred with 25 ml of acetic acid-wafter-tetrahydrofuran (65:35:10 V/V/V) for 18 hr at room temperature. The solvents were removed in vacuo and the residue was taken up in 30 ml of water and 30 ml of ether-ethyl acetate (1:1 V/V). The aqueous material was extracted with 60 ml (2×30 ml) of ether-ethyl acetate (1:1 V/V). This extract and the organic material were combined and washed with 30 ml of saturated aqueous sodium bicarbonate and then with 30 ml of saturated sodium chloride. The washed material was then dried over anhydrous magnesium sulfate and the solvent was removed by evaporation in vacuo. The residue (0.128 g) was taken up with 3 ml of glacial acetic acid and 0.5 ml of water and stirred at 60° C. for 18 hr. This mixture was cooled and the solvents were removed in vacuo. The resulting residue was taken up in 10 ml of water and 20 ml of ether-ethyl acetate (1:1 V/V) and the phases which formed were separated. The aqueous phase was extracted with 40 ml (2×20 ml) of ether-ethyl acetate (1:1 V/V). The ether-ethyl acetate extract was combined with the organic phase and the mixture was washed with 20 ml of saturated aqueous sodium bicarbonate and then with 20 ml of saturated aqueous sodium chloride. The washed mixture was dried over anhydrous magnesium sulfate and the solvent was removed by evaporation in vacuo. The residue was chromatographed on a column of silicic acid-Celite (85:15 W/W) using a benzene-ethyl acetate gradient elution to yield the title compounds.

A. Title compound TR-4280 had the following physical characteristics:

Analysis—NMR(CDCl$_3$): $\delta$0.9 (3H, triplet, J=6 Hz), 0.8–2.8 (22H, multiplet), 3.3 (1H, multiplet), 3.75 (3H, singlet), 4.1 (1H, multiplet) 5.6 (2H, multiplet), 6.2 (1H, multiplet) and 7.6 ppm (1H, multiplet); IR(CHCl$_3$)$\nu$: 2950, 1730, 1710 cm$^{-1}$.

B. Title compound TR-4281 had the following physical characteristics:

Analysis—NMR(CDCl$_3$): $\delta$0.9 (3H, triplet, J=6 Hz), 0.7–2.6(22H, multiplet), 2.2 (3H, singlet), 3.3 (1H, multiplet), 3.8 (3H, singlet), 5.7 (2H, multiplet), 6.3 (1H, multiplet), and 7.5 ppm (1H, multiplet); IR(CHCl$_3$)$\nu$: 2950, 1750, 1730, 1710 cm$^{-1}$.

EXAMPLE 35

This example illustrates the preparation of:
A. Methyl 16,19-cyclo-15S-hydroxy-16-methyl-20-nor-9-oxoprosta-10,13E-dien-1-oate (TR-4684); and
B. Methyl 16,19-cyclo-15R-hydroxy-16-methyl-20-nor-9-oxoprosta-10,13E-dien-1-oate (TR-4683).

Repeating in a similar manner the procedure of Example 34, but replacing 1-iodo-3-(1-ethoxyethoxy)-3-(3-ethylcyclobutyl)-1E-propene with 1-iodo-3-(1-ethoxyethoxy)-3-(1-methylcyclobutyl)-1E-propene (prepared in Example 8B) yields the title compounds.

A. Title compound TR-4884 had the following physical characteristics:

Analysis—NMR(CDCl$_3$): $\delta$1.13 (3H, singlet), 1.2 to 2.8 (20H, multiplet), 3.4 (1H, multiplet), 3.77 (3H, singlet), 4.15 (1H, multiplet), 5.8 (2H, multiplet), 6.38 (1H, multiplet) and 7.7 ppm (1H, multiplet); IR(CHCl$_3$)$\nu$: 970, 1170, 1440, 1705, 1730, 2860, 2940 and 3200 to 3600 cm$^{-1}$ (broad); Mass Spectrum (70 eV)m/e:348 (p), 330(p-H$_2$O), 316(p-CH$_3$OH), 298(p-H$_2$O-CH$_3$OH), 279 (p-C$_5$H$_9$), 261(p-H$_2$O-C$_5$H$_9$); Optical Rotation: $[\alpha]_D$+96.0° (c 1.08,CHCl$_3$).

B. Title compound TR-4683 had the following physical characteristics:

Analysis—NMR,IR and Mass Spectrum similar to title compound TR-4684 above; Optical Rotation: $[\alpha]_D$+97.9° (c 0.95,CHCl$_3$).

EXAMPLE 36

This example illustrates the preparation of:
A. Methyl 15S-hydroxy-16,18-methano-16-methyl-9-oxoprosta-10,13E-dien-1-oate (TR-4695); and
B. Methyl 15R-hydroxy-16,18-methano-16-methyl-9-oxoprosta-10,13E-dien-1-oate (TR-4694).

Repeating in a similar manner the procedure of Example 34, but replacing 1-iodo-3-(1-ethoxyethoxy)-3-(3-ethylcyclobutyl)-1E-propene with 1-iodo-3-(1-ethoxyethocy)-3-(1-methyl-3-ethylcyclobutyl)-1E-propene (prepared in Example 8A) yields the title compound.

A. Title compound TR-4694 had the following physical characteristics:

Analysis—NMR(CDCl$_3$): $\delta$0.80 (3H, triplet, J=7.0 Hz), 1.07 and 1.13 (3H, total, 2 singlets, isomers), 1.0 to 2.7 (21H, multiplet), 3.30 (1H, multiplet), 3.73 (3H, singlet), 4.0 (1H, multiplet), 5.76 (2H, multiplet), 6.30 (1H, multiplet) and 7.63 ppm (1H, multiplet); IR(CHCl$_3$)$\nu$: 970, 1090, 1170, 1220, 1370, 1430, 1455, 1700, 1725, 2850, 2920, 3460 (broad) and 3600 cm$^{-1}$; Mass Spectrum (70 eV)m/e:376 (p),358, 326, 325, 297, 296, 278, 261, 246 (base), 229; Optical Rotation: $[\alpha]_D$+96.8°(c 0.94,CHCl$_3$).

B. Title compound TR-4695 had the following physical characteristics:

Analysis—NMR,IR and Mass Spectrum similar to title compound TR-4694 above; Optical Rotation: $[\alpha]_D$+81° (c 1.07,CHCl$_3$).

EXAMPLE 37

This example illustrates the preparation of:
A. Methyl 16,18-methano-9$\alpha$,1$\alpha$,15S-trihydroxyprost-13E-en-1-oate (TR-4624); and
B. Methyl 16,18-methano-9$\beta$,11$\alpha$,15S-trihydroxyprost-13E-en-1-oate (TR-4625).

A solution of 1-iodo-3-(1-ethoxyethoxy)-3-(3-ethylcyclobutyl)-1E-propene (2.194 g. 6.49 mmol; prepared in Example 1J) in 50 ml of dry ether (distilled from sodium benzophenone ketyl) was prepared and cooled to −78° C. To this solution there was added 7.29 ml of 1.78 M (12.98 mmol) t-butyllithium in pentane and the mixture was stirred for 2 hr at −78° C. Copper (I) pentyne (0.844 g, 6.49 mmol) was slurried in 50 ml of dry ether and 2.24 ml of dry hexamethylphosphorus triamide was added and the mixture was stirred for 30 min and then cooled to −78° C. To this copper reagent solution there was then added the previously prepared organolithium solution. A solution of methyl 7-[3$\alpha$(tetrahydropyran-2-yloxy)-5-oxocyclopent-1-enyl] heptanoate (2.035 g. 6.2 mmol; preparation described in J. Amer. Chem. Soc., 95:1696 [1973]) in 4 ml of dry ether was slowly added to the lithium dialkenyl cuprate solution prepared above. The resulting mixture was stirred for 30 min at −78° C., then for 90 min at −20° C. and then the mixture was quenched with 20% aqueous ammonium sulfate solution. This mixture was shaken for 10 min and the phases which formed were separated. The aqueous phase was extracted with 100 ml (2×50 ml) of ether. The organic phase was shaken with cold 2% aqueous sulfuric acid. This acidic aqueous phase was then extracted with 100 ml (2×50 ml) of ether. The combined ether extracts were filtered through Celite (diatomaceous earth). The filtrate was washed with 50 ml of saturated sodium bicarbonate solution and then with 50 ml of saturated aqueous sodium chloride solution. The washed extract was dried over anhydrous magnesium sulfate and the solvent was removed by evaporation in vacuo. The residue was stirred with 25 ml of acetic acid-water-tetrahydrofuran (65:35:10 V/V/V) for 18 hr at room temperature. The solvents were removed in vacuo and the residue was taken up in 30 ml of water and 30 ml of ether-ethyl acetate (1:1 V/V). This extract and the separated organic material were combined and the mixture was washed with 30 ml of saturated aqueous sodium bicarbonate and then with 30 ml of saturated sodium chloride. The washed material was then dried over anhydrous magnesium sulfate and the solvent was removed by evaporation in vacuo. The residue was chromatographed on silicic acid-Celite (85:15 W/W) using a benzene-ethyl acetate gradient elution and the 15R-PGE$_1$ isomer was separated (Optical Rotation: $[\alpha]_D - 39.8°$[c1.0,CHCl$_3$]). A solution containing 466 mg of this separated isomer in 25 ml of methanol was prepared and stirred with ice-bath cooling as 700 mg of sodium borohydride was added over 15 min. The resultant mixture was stirred with ice-bath cooling for 0.5 hr and then without cooling for 0.5 hr. Water was added to this reaction mixture and the solvents were removed by evaporation in vacuo. The residue was mixed with water and extracted four times with ethyl acetate. The combined ethyl acetate extract was dried over anhydrous magnesium sulfate and evaporated in vacuo. The residue was chromatographed on silicic acid-Celite (85:15) to yield the title compounds.

A. Title compound TR-4624 had the following physical characteristics:

Analysis—NMR(CDCl$_3$): δ0.77 (3H, broad triplet, J=6.5 Hz), 1.0–2.7 (24H, multiplet), 2.65 (3H, broad singlet), 3.7 (3H, singlet), 4.01 (2H, broad multiplet), 4.23 (1H, broad multiplet) and 5.6 ppm (2H, multiplet); IR(CHCl$_3$)ν: 1740, 2950 and 3200 to 3600 cm$^{-1}$(broad); Mass Spectrum (70 eV)m/e:382(p, weak), 364(p-H$_2$O), 346(p-2H$_2$O), 333(p-H$_2$O-CH$_3$O), 315(p-2H$_2$O-CH$_3$O), 299 (p-C$_6$H$_{11}$), 292, 281(p-H$_2$O-C$_6$H$_{11}$), 263,249,236,221; Optical Rotation: $[\alpha]_D + 7.0$(c 1.0,CHCl$_3$).

B. Title compound TR-4625 had the following physical characteristics:

Analysis—NMR(CDCl$_3$): δ0.77 (3H, broad triplet, J=6.5 Hz), 1.0–2.7 (24H, multiplet), 3.5 (3H, singlet), 3.7 (3H, singlet), 4.02 (3H, broad multiplt) and 5.61 ppm (2H, multiplet); IR and Mass Spectrum similar to TR-4624 above; Optical Rotation: $[\alpha]_D - 21.0°$ (c 1.0,CHCl$_3$).

EXAMPLE 38

This example illustrates the preparation of:
A. Methyl 11α,15R-dihydroxy-16,18-methano-20,20-propano-9-oxoprost-13E-en-1-oate (TR-4796); and
B. Methyl 11α,15S-dihydroxy-16,19-methano-20,20-propano-9-oxoprost-13E-en-1-oate (TR-4797)

Repeating in a similar manner the procedure of Example 30, but replacing 1-iodo-3-(1-ethoxyethoxy)-3-(3-ethylcyclobutyl)-1E-propene with 1-[3-(cyclobutylmethyl)-cyclobutyl]-1-(1-ethoxyethoxy)-trans-3-iodoprop-2-ene (prepared in Example 21B) yields the title compounds.

A. Title compound 4796 had the following physical characteristics:

Analysis—NMR(CDCl$_3$): δ3.65 (s,3H), 3.2–4.2 (complex, 4H) and 5.50 (complex, 2H); IR(CHCl$_3$) λ$_{max}$: 2.78, 2.95 (broad), 5.75, 6.95 and 10.40μ; Mass Spectrum (70 eV)m/e:402(p-H$_2$O), 384(p-2H$_2$O) and 271(p-H$_2$O-OCH$_3$); Optical Rotation: $[\alpha]_D - 32.1°$ (c 1.0,CHCl$_3$).

B. Title compound 4797 had the following physical characteristics:

Analysis—NMR(CDCl$_3$): δ3.65 (s, 3H), 3.8–4.2 (complex, 2H) and 5.65 (complex, 2H); IR(CHCl$_3$) λ$_{max}$: 2.78, 2.90 (broad), 5.75 and 10.4μ; Mass Spectrum: essentially same as TR-4796 above; Optical Rotation: $[\alpha]_D - 57.4°$ (c 0.73,CHCl$_3$).

EXAMPLE 39

This example illustrates the preparation of:

A. 1,11α,15R-Trihydroxy-16,18-methano-20,20-propanoprost-13E-en-9-one (TR-4832); and
B. 1,11α,15S-Trihydroxy-16,18-methano-20,20-propanoprost-13E-en-9-one (TR-4833).

Repeating in a similar manner the procedure of Example 23, but replacing 1-iodo-3-(1-ethoxyethoxy)-3-(3-ethylcyclobutyl)-1E-propene with 1-[3-(cyclobutylmethyl)-cyclobutyl]-1-(1-ethoxyethoxy)-trans-3-iodoprop-2-ene (prepared in Example 21B) yields the title compounds.

A. Title compound 4832 had the following physical characteristics:

Analysis—NMR(CDCl$_3$): δ3.65 (t,J=5.0 Hz,2H), 3.20 (broad s, 3H), 3.92 (complex, 3H) and 5.56 (complex, 2H); IR(CHCl$_3$) λ$_{max}$: 2.78, 2.90 (broad), 5.75 and 10.4μ; Mass Spectrum (70 eV)m/e:374(p-H$_2$O) and 356(p-2H$_2$O); Optical Rotation: $[\alpha]_D - 57.2°$(c 0.76,CHCl$_3$).

B. Title compound 4833 had the following physical characteristics:

Analysis—NMR(CDCl$_3$): δ3.65 (t,J=5.0 Hz, 2H), 4.00 (complex, 2H) and 5.65 (complex, 2H); IR(CHCl$_3$) λ$_{max}$: 2.78, 2.92 (broad), 5.75, 9.25 and 10.4μ; Mass Spectrum: essentially same as TR-4832 above; Optical Rotation: $[\alpha]_D - 66.3°$(c 0.93,CHCl$_3$).

EXAMPLE 40

This example illustrates the preparation of:
A. 1,11α,15S-Trihydroxy-16,18-methano-19,20-ethanoprost-13E-en-9-one (TR-4880); and
B. 1,11α,15R-Trihydroxy-16,18-methano-19,20-ethanoprost-13E-en-9-one (TR-4881).

Repeating in a similar manner the procedure of Example 23, but replacing 1-iodo-3-(1-ethoxyethoxy)-2-(3-ethylcyclobutyl)-1E-propene with 1-iodo-3-(1-ethoxyethoxy)-3-(3-cyclobutyl) cyclobutyl-1E-propene (prepared in Example 42) yields the title compounds.

A. Title compound 4881 had the following physical characteristics:

Analysis—NMR(CDCl$_3$): δ3.33 (broad s, 3H), 3.62 (t,J=6.0 Hz, 2H), 3.90 (complex, 2H) and 5.56 (complex, 2H); IR(CHCl$_3$) λ$_{max}$: 2.78, 2.90 (broad), 5.75 and 10.4μ; Mass Spectrum (70 eV)m/e: 360(p-H$_2$O), 342(p-2H$_2$O) and 332(p-H$_2$O-C$_2$H$_4$); Optical Rotation: $[\alpha]_D - 43.4°$(c 1.2,CHCl$_3$).

B. Title compound 4880 had the following physical characteristics:

Analysis—NMR(CHCl$_3$): δ3.63 (t,J=6.0 Hz, 2H), 3.96 (complex, 2H) and 3.66 (complex, 2H); IR and Mass Spectrum: essentially same as TR-4881 above; Optical Rotation: $[\alpha]_D - 53.6°$(c 0.75,CHCl$_3$).

EXAMPLE 41

This example illustrates the preparation of:
A. Methyl 11α,15R-dihydroxy-16,18-methano-19,20-ethano-9-oxoprost-13E-en-1-oate (TR-4882); and
B. Methyl 11α,15S-dihydroxy-16,18-methano-19,20-ethano-9-oxoprost-13E-en-1-oate (TR-4887).

Repeating in a similar manner the procedures of Example 30, but replacing 1-iodo-3-(1-ethoxyethoxy)-3-(3-ethyl) cyclobutyl-1E-propene with 1-iodo-3-(1-ethoxyethoxy)-3-(3-cyclobutyl) cyclobutyl-1E-propene (prepared in Example 42) yields the title compounds.

A. Title compound 4882 had the following physical characteristics:

Analysis—NMR(CDCl$_3$): δ3.66 (s, 3H), 4.00 (complex, 4H) and 5.53 (complex, 2H); IR(CHCl$_3$) λ$_{max}$: 2.90 (broad), 5.75, 6.95 and 10.4μ; Mass Spectrum (70 eV)m/e: 370(p-H$_2$O), 357(p-2H$_2$O) and 339(p-H$_2$O-C$_2$H$_4$); Optical Rotation: [α]$_D$−57.2°(c 1.2,CHCl$_3$).

B. Title compound 4887 had the following physical characteristics:

Analysis—NMR(CDCl$_3$): δ3.66 (s, 3H), 4.00 (complex, 2H) and 4.67 (complex, 2H); IR(CHCl$_3$) λ$_{max}$: 2.78, 2.90 (broad), 5.75, 6.99 and 10.4μ; Optical Rotation: [α]$_D$−43.8°(c 0.99,CHCl$_3$).

EXAMPLE 42

This example illustrates the preparation of 1-iodo-3-(1-ethoxyethoxy)-3-(3-cyclobutyl) cyclobutyl-1E-propene.

A. Preparation of Cyclobutane carbinol

A slurry of 21.0 g (0.55 moles) of lithium aluminum hydride (LAH) in 500 ml ether was stirred under argon at 0° C. and a solution of 50.0 g of cyclobutane-carboxylic acid in 250 ml ether added dropwise. The reaction mixture was refluxed for 2.0 hr. The reaction mixture was cooled to 0° C. and 75 ml of ethyl acetate cautiously added, followed successively by 21 ml H$_2$O, 21 ml of 15% NaOH, and 45 ml of H$_2$O. The resultant mixture was stirred for 0.5 hr at 25° C. and then filtered. The residue was washed with ether. The filtrate was washed with brine, then dried (MgSO$_4$) and filtered. Product was isolated by distillation (aspirator vacuum) to yield 24.4 g of the title compound having the following physical characteristics:

Analysis—NMR(CDCl$_3$): δ3.55 (d,J=7.0H$_2$, 2H); IR(CHCl$_3$)ν: 3600, 3450 (broad) and 1020 cm$^{-1}$; bp 55°-60° C.

B. Preparation of (p-Toluenesulfonyloxy) (cyclobutyl) methane

A solution of 24.4 g of Cyclobutane carbinol (prepared in Example 42A) in 570 ml of dry pyridine was stirred under argon at −10° C. and 81.0 g of tosyl chloride added in small portions. The reaction mixture was stirred at −10° C. to −0° C. for 4.5 hr, then poured into 1 liter of chilled 6 N HCl. The layers were separated and the aqueous layer extracted with ether-ethyl acetate. The combined extracts were washed with 10% aqueous sodium bicarbonate (NaHCO$_3$), dried (MgSO$_4$), filtered and evaporated in vacuo to yield 72.0 g of the title compound having the following physical characteristics:

Analysis—NMR(CDCl$_3$): δ2.42 (s, 3H), 4.0 (d,J=7.0 Hz, 2H), 7.35 (d,J=7.0 Hz, 2H), 7.35 (d,J=9.0 Hz, 2H) and 7.80 (d,J=9.0 Hz, 2H); IR(CHCl$_3$)ν: 1600, 1260, 1170 and 1090 cm$^{-1}$; no 3600 or 3450 cm$^{-1}$ signals observed.

C. Preparation of Cyclobutyl Acetonitrile

A solution of 68.0 g of (p-Toluenesulfonyloxy) (cyclobutyl) methane (prepared in Example 42B) and 22.0 g of sodium cyanide in 450 ml of dry dimethyl sulfoxide was stirred and heated to 100° C. for 18.0 hr under argon. The reaction mixture was cooled to 0° C. and poured into 400 ml of 20% aqueous NH$_4$Cl. The aqueous layer was extracted with 1:1 ether-hexane. The combined extracts were washed with water, dried (Na$_2$SO$_4$), filtered, and evaporated at 25° C. to yield 22.6 g of the title compound having the following physical characteristics:

Analysis—NMR(CDCl$_3$): δ2.4(d,J=5.0 Hz, 2H); IR(CHCl$_3$)ν: 2250 cm$^{-1}$.

D. Preparation of Cyclobutyl acetic acid

A 2 liter, 3-necked, round-bottom flask was equipped with a reflux condenser, mechanical stirring, serum cap, and a long needle (used as an argon inlet). A solution of 22.6 g of Cyclobutyl acetonitrile (prepared in Example 42C) in 480 ml of 95% ethanol and 450 ml of 30% aqueous hydrogen peroxide was added to the reaction vessel and stirred at 50° C. while argon was passed through the solution for 5.0 hr. The reaction mixture was cooled to 0° C. and brine added to the solution, followed by sodium chloride. The mixture was acidified with 6 N HCl, and extracted with 1:1 ether-ethyl acetate. The combined extracts were washed with brine, dried (MgSO$_4$), filtered and evaporated in vacuo to afford 22.9 g of the title compound having the following physical characteristics:

Analysis—NMR(CDCl$_3$): δ2.50 (d,J=3.0 Hz, 2H) and 8.2 (broad s, 1H); IR(CHCl$_3$)ν: 3500, 3600-2400(broad), 1700 and 1600 cm$^{-1}$; mp 148°-149° C.

E. Preparation of Ethyl cyclobutyl acetate

A solution of 22.9 g of cyclobutyl acetic acid (prepared in Example 42D) in 46 ml of absolute ethanol was stirred under argon at 25° C. and 9.30 ml of conc. H$_2$SO$_4$ added. The reaction mixture was refluxed under argon for 16.0 hr. The reaction mixture was cooled to 25° C. and diluted with ether. The ether layer was washed with water and 1 N aqueous K$_2$CO$_3$, dried (MgSO$_4$), filtered and isolated by distillation (aspirator vacuum) to yield 19.9 g. of the title compound having the following physical characteristics:

Analysis—NMR(CDCl$_3$): δ1.22(t,J=7.0 Hz, 3H), 2.40 (d,J=6.0 Hz, 2H) and 4.10(q,J=7.0 Hz, 2H); IR(CHCl$_3$): ν1725, 1450, 1380 and 1030 cm$^{-1}$; bp 60°-65° C.

F. Preparation of Ethyl 2-cyclobutyl malonate

A solution of 10.2 ml of diisopropyl amine in 83.0 ml of dry THF was cooled to 0° C. with stirring under argon and 40.0 ml of 2.3 M n-butyllithium in hexane injected dropwise. After 15.0 min at 0° C., the reaction mixture was cooled to −78° C. and a solution of 11.6 g of ethyl cyclobutyl acetate (prepared in Example 42E) in 43.0 ml of THF added dropwise. After 15 min at −78° C., a solution of 7.70 ml of ethyl chloroformate in 3.3 ml of THF was added to the reaction mixture. The reaction mixture was stirred for 1.5 hr at −78° C. The reaction mixture was partitioned between 20% aqueous NH$_4$Cl and ether. The ether layer was washed with brine, then dried (MgSO$_4$), filtered and isolated by distillation (oil pump vacuum) to yield 7.49 g of the title compounds having the following physical characteristics:

Analysis—NMR(CDCl$_3$): δ1.23(t,J=7.0 Hz, 3H), 3.36(d,J=10.0 Hz, 1H) and 4.18(q,J=7.0 Hz, 2H); bp 66°-70° C.

G. Preparation of 2-Cyclobutyl-propane-1,3-diol

The title compound was prepared according to the procedure of Example 1A by replacing diethyl ethylmalonate with ethyl 2-cyclobutyl malonate (prepared in Example 42F). The resulting product had the following physical characteristics:

Analysis—NMR(CDCl$_3$): δ3.2-4.2 (complex, 6H), and 1.4-2.5 (complex, 8H); IR(CHCl$_3$)ν: 3610 and 3400 (broad) cm$^{-1}$; bp 90°-95° C.

H. Preparation of 2-Cyclobutyl-1,3-ditosyloxypropane

The title compound was prepared according to the procedure of Example 1B by replacing 2-ethylpropane-1,3-dial with 2-cyclobutyl-propane-1,3-dial (prepared in Example 42G). The resulting product had the follow physical characteristics:

Analysis—NMR(CDCl$_3$): $\delta$2.42 (s, 2H), 3.92 (broad t, 4H), 7.35 (d,J=9.0 Hz, 2H) and 7.75 (d,J=9.0 Hz, 2H); IR(CHCl$_3$)$\nu$: 1600, 1360, 1180, 1090 and 1000 cm$^{-1}$.

I. Preparation of 1,1-Bis ethoxy-carbonyl-3-cyclobutyl cyclobutane

The title compound was prepared according to the procedure of Example 1C by replacing 2-ethyl-propyl-1,3-ditosylate with 2-cyclobutyl-1,3-ditosyloxypropane (prepared in Example 42H), the resulting product had the following physical characteristics:

Analysis—NMR(CDCl$_3$): $\delta$1.22 (t,J=7.0 Hz, 6H) and 4.20(q,J=7.0 Hz, 4H); IR(CHCl$_3$): $\nu$1720, 1370, 1270, 1020 and 860 cm$^{-1}$; bp 125°–129° C.

J. Preparation of 3-cyclobutyl-cyclobutane-1,1-dicarboxylic acid

The title compound was prepared according to the procedure of Example 1D replacing 3-ethyl-1,1-dicarbethoxycyclobutane with 1,1-bis-ethoxy-carbonyl-3-cyclobutyl (prepared in Example 42I). The resulting product had the following physical characteristics:

Analysis—NMR(CDCl$_3$): $\delta$1.3–3.0 (complex, 12H), 9.7 (broad s, 2H); IR(CHCl$_3$): $\nu$3600, 2400, 1700, 1410 and 1290 cm$^{-1}$; mp 150°–151° C.

K. Preparation of 3-Cyclobutyl-cyclobutane-1-carboxylic acid

The title compound was prepared according to the procedure of Example 1E by replacing 3-ethylcyclobutane-1,1-dicarboxylic acid with 3-cyclobutyl-cyclobutane-1,1-dicarboxylic acid (prepared in Example 42J). The resulting product had the following physical characteristics:

Analysis—NMR(CDCl$_3$): $\delta$1.2–2.6 (complex, 12H), 2.9 (complex, 1H), 11.2 (broad s, 1H); IR(CHCl$_3$): $\nu$3400–2300, 1700, and 1420 cm$^{-1}$; bp 91°–93° C.

L. Preparation of 3-Cyclobutyl-cyclobutane-1-carboxylic acid chloride

The title compound was prepared according to the procedure of Example 1F by replacing 3-ethylcyclobutane carboxylic acid with 3-cyclobutyl-cyclobutane-1-carboxylic acid (prepared in Example 42K). The resulting product had the following physical characteristics:

Analysis—NMR(CDCl$_3$): $\delta$1.3–3.0 (complex, 12H), 3.5 (complex, 1H), no CO$_2$H signal observed; IR(CHCl$_3$): $\nu$1790 and 1060 cm$^{-1}$; bp 43°–45° C.

M. Preparation of (3-Cyclobutyl-cyclobutyl) (2-chlorovinyl) ketone

The title compound was prepared using the procedure of Example 1G by replacing 3-ethylcyclobutane carboxylic acid chloride with 3-cyclobutyl-cyclobutane-1-carboxylic acid chloride (prepared in Example 42L). The resulting product had the following physical characteristics:

Analysis—NMR(CDCl$_3$): $\delta$1.3–2.9 (complex, 12H), 3.2 (complex, 1H), 6.42 (d,J=14.0 Hz), 1H) and 7.25 (d,J=14.0 Hz, 1H); IR(CHCl$_3$): $\nu$1670, 1490 and 935 cm$^{-1}$; bp 75°–80° C.

N. Preparation of (3-Cyclobutyl-cyclobutyl) (2-iodovinyl) ketone

The title compound was prepared using the procedure of Example 1H by replacing 3-ethylcyclobutyl-trans-$\beta$-chlorovinyl ketone with (3-cyclobutyl-cyclobutyl)(2-chlorovinyl) ketone (prepared in Example 42M). The resulting product had the following physical characteristics:

Analysis—NMR(CDCl$_3$): $\delta$1.3–2.7 (complex, 12H) 7.08 (d,J=16.0 Hz, 1H) and 7.80 (d,J=16.0 Hz, 1H).

O. Preparation of 1-Iodo-3-(3-cyclobutyl-cyclobutyl)-3RS-hydroxy-1E-propene

The title compound was prepared using the procedure of Example II by replacing 3-ethylcyclobutyl-trans-$\beta$-iodovinyl ketone with (3-cyclobutyl-cyclobutyl)(2-iodovinyl) ketone (prepared in Example 42N). The resulting product had the following physical characteristics:

Analysis—NMR(CDCl$_3$): $\delta$0.9–2.8 (complex, 14H), 4.0 (complex, 1H), 6.40 (complex, 2H); IR(CHCl$_3$): $\nu$ 3600, 3450 (broad), 1610, 940 cm$^{-1}$.

P. Preparation of 1-Iodo-3-(3-cyclobutyl-cyclobutyl)-3RS-(1-ethoxy)ethoxy-1E-propene The title compound was prepared using the procedure of Example 1J by replacing 1-(3-ethylcyclobutyl)-trans-3-iodoprop-2-en-1-ol with 1-iodo-3-(3-cyclobutyl-cyclobutyl)-3RS-hydroxy-1E-propene (prepared in Example 42-0). The resulting product had the following physical characteristics:

Analysis—NMR(CDCl$_3$): $\delta$1.2 (t,J=8.0 Hz, 3H), 1.28 (d,J=8.0 Hz, 3H), 3.6 (complex, 4H), 4.68 (q,J=8.0 Hz, 1H), 6.35 (complex, 2H); IR(CHCl$_3$): $\nu$ 1610, 1450, 945 cm$^{-1}$.

EXAMPLE 43

A. Evaluation of Inhibition of Human Platelet Aggregation by Analogs of Prostaglandins Structure III The ability of test compounds to inhibit platelet aggregation was determined by a modification of the turbidimetric technique of Born (Nature, 194:927 [1962]). Blood was collected from human volunteer who had not ingested aspirin or aspirin-containing products within the preceding two weeks in heparinized containers and was allowed to settle for one hr. The platelet rich plasma (PRP) supernates were collected and cooled. Siliconized glassware was used throughout.

In a representative assay 1.9 ml of PRP and 0.2 ml of test compound at the appropriate concentrations (0.001 to 100 mcgm), or 0.2 ml of distilled water (control procedure) were placed in sample cuvettes. The cuvettes were placed in a 37° C. incubation block for 15 min, and then in a spectrophotometer linked to a strip chart recorder. After 30 to 60 seconds, 0.2 ml of a solution, prepared by diluting a calf-skin collagen solution 1:9 with Tyrodes' Solution, was added to each cuvette. Platelet aggregation was evidenced by a decrease in optical density.

Calculation of the degree of inhibition of platelet aggregation exhibited by each concentration of test compound was accomplished according to the method of Caprino et al., (Arzneim-Forsch., 23:1277 [1973]). An ED$_{50}$ value was then determined graphically. Activity of the compounds was scored as follows:

| ED$_{50}$(mcg/kg) | Activity Value |
|---|---|
| No activity | 0 |
| >1.0 | 1 |
| >0.1 ≦1.0 | 2 |
| >0.01 ≦0.1 | 3 |
| >0.001 ≦0.01 | 4 |
| ≦0.001 | 5 |

B. Evaluation of the Effects of Prostaglandin Analogs III on Gastric Secretion in the Rat A procedure based on that described by Lipmann (J. Pharm. Pharmacol., 21:335 [1968]) was used to assess the influence of test compounds on gastric secretion. Rats of one sex weighing 150 to 200 g were randomly divided into groups of six animals each and fasted for 48 hr previous to the experiments, water being available ad limitum. The animals were anesthetized with ether, the abdomen was opened through a midline incision and the pylorus was ligated. Test compounds were diluted from stock solution so as to administer a dose of 1.5 mg/kg in a volume equivalent to 1 ml/kg. Subcutaneous injections were applied immediately after surgery and again 2 hr later, so that a total dose of 3.0 mg/kg was administered. Dilutions were made with phosphate buffer (pH 7.38) as recommended by Lee et al. (Prostaglandins 3:29 [1973]), in order to insure adequate stability of drugs at the subcutaneous depot. Each compound was tested in one group of rats; an additional control group received only the vehicle.

Four hr after pyloric ligation the animals were killed with ether, the cardias ligated and the stomachs removed. The volume of gastric secretion was measured and the contents centrifuged at 5000 rpm for 10 min. Total acid in the supernatant was titrated against a 0.1 N sodium hydroxide solution and the amount expressed in mEq.

Volume and total acid values of the treated group were compared with those of the controls by the "T" test. Anti-secretory activity was scored according to the following scale:

| % decrease in acidity | Activity Value |
|---|---|
| <26 | 0 |
| 26-50, not significant | 1 |
| 26-50, significant | 2 |
| 51-75 | 3 |
| 76-100 | 4 |

C. Evaluation of the Effects of Prostaglandin Analogs III on the Femoral Blood Flow in the Dog The peripheral vasodilator or constrictor effects of test compounds were determined in mongrel dogs of either sex, weighing between 10 and 20 kg anesthestized intravenously with 35 mg/kg of sodium pentobarbital. An external iliac artery was dissected immediately above the femoral arch for a length of approximately 5 cm and a previously calibrated, non-connulating electromagnetic flowmeter sensor with a lumen between 2.5 and 3.5 mm was placed snugly around the vessel. Cannulas were placed in a branch of the artery arising distally to the location of the flowmeter sensor for intraarterial drug administrations, in the contralateral femoral artery for systemic blood pressure recordings and in the trachea for artificial respiration with room air. Femoral blood flow and systemic blood pressure were continuously recorded with an electromagnetic flowmeter and pressure transducer, respectively.

After an adequate control period, test compounds were injected intraarterially at one log-spaced doses ranging from 0.001 to 10 mcg., in a volume of 0.5 ml and at 5 to 10 min intervals. Maximum changes in blood-flow, as well as any variations in blood pressure, were tabulated for each dose in absolute values (ml/min and mmHg). The calculations were made taking as control values those existing immediately before administration of each dose. The direction of the observed change (+ for increase and − for decrease) was also noted. The dose changing bloodflow by 100 ml/min (ED$_{100ml/min}$) was calculated graphically and was used for scoring activity as follows:

| ED$_{100ml/min}$, mcg | Activity Value |
|---|---|
| >10.0 | 0 |
| 1.0–10.0 | 1 |
| 0.11–1.0 | 2 |
| 0.01–0.1 | 3 |

D. Evaluation of the Effects of Prostaglandin Analogs III on Blood Pressure and Heart Rate in the Anesthetized Cat The acute effects of test compounds on blood pressure and heart rate were determined in cats of either sex anesthetized with a mixture of pentobarbital sodium (35 mg/kg, i.v.) and barbital sodium (100 mg/kg, i.v.). Cannulas were placed in the trachea to allow adequate spontaneous ventilation, in a femoral artery for blood pressure recording with a strain gage transducer, and in a saphenous vein for drug administration. Heart rate was recorded by means of a cardiotachometer driven by the R wave of the electrocardiogram. After a period of 10 min of stable recordings of blood pressure and heart rate, the test compound was administered intravenously at doses increasing from 0.01 to 10.0 mcg/kg, spaced one log and injected at 10 min intervals. All doses were injected in a volume of 0.1 ml/kg. Modifications of blood pressure and heart rate induced by the test compound were expressed both in absolute units (mmHg and beats/min) and as percent of values recorded immediately before administration of each dose. Biphasic responses were tabulated in the order in which they occur. The direction of the observed changes was also noted (+ for increase and − for decrease).

Activity of compounds in this test was judged only on the basis of the degree of hypotension observed. Thus, the ED$_{50}$ mmHg (dose decreasing blood pressure by 50 mmHg) was calculated graphically and the compound scored according to the following scale:

| ED$_{50}$ mmHg, mcg/kg | Activity Value |
|---|---|
| >10.1 | 0 |
| 1.01–10.0 | 1 |
| 0.11–1.0 | 2 |
| 0.01–0.1 | 3 |

E. Evaluation of the Effects of Prostaglandin Analogs III on Blood Pressure in the Hypertensive Rat The acute antihypertensive activity of test compounds is determined in rats made hypertensive by the procedure of Grollman (A. Proc. Soc. Exper. Biol. Med., 57:102, [1944]). Female rats weighing between 60 and 100 g are anesthetized with ether, the right kidney approached through a flank retroperitoneal incision, decapsulated and tied with a figure-of-eight ligature. The animals are left to recover and two weeks later are again anesthetized and the contralateral kidney removed. Four weeks after the second operation the rats are subjected to indirect blood pressure measurements and those showing systolic pressure values greater than 160 mmHg are selected for drug testing.

Blood pressure is measured in the tail with an inflatable occluding cuff placed at the base of the extremity and a pulse detector located distally. The cuff is inflated to approximately 300 mmHg and is slowly deflated until pulsations appear, indicating the level of systolic pressure; diastolic pressure is not recorded by this procedure. All measurements are carried out in unanesthetized, unsedated animals maintained in a warm environment during the recording procedure and for at least 6 hr before. In all cases, three pressure readings are obtained in succession and mean values are calculated thereof.

Experiments are carried out in groups of five hypertensive rats in which systolic pressure is determined immediately before and 2, 4, 6 and 8 hr after the intraperitoneal administration of the test compound at a dose of 1 mg/kg. Drugs are diluted from stock solutions with phosphate buffer (Lee et al., Prostaglandins 3:29 [1973]), so as to inject this quantity in a volume of 1 ml/kg. Changes from control blood pressure values are calculated for each interval both in mmHg and in per-cent, and evaluated for significance by means of Wilcoxon's signed rank test (Wilcoxon and Wilcox, Some rapid approximate statistical procedures, Lederle Laboratories, Pearl River [1964]). Activity of the compound is scored as follows:

| Blood pressure decrease | Activity Value |
|---|---|
| Not significant at any time interval | 0 |
| Significant at one time interval | 1 |
| Significant at two time intervals | 2 |
| Significant at three time intervals | 3 |
| Significant at all four intervals | 4 |

F. Evaluation of the Effects of Prostaglandin Analogs III on the Rat Uterus

The uterine stimulant effect of test compounds is determined in segments of uterus obtained from rats (140-160 g) pretreated subcutaneously with 1 mg/kg of diethylstibesterol 18 hr before the experiment. The tissues are placed in 10 ml chambers filled with de-Jalon solution at 29° C. and bubbled with 95% $O_2$ and 5% $CO_2$, and prepared for isometric recording with force displacement transducers. Preparations are stretched to an initial tension of 1 g and are left undisturbed for 30 min, after which two responses to 1 mcg/ml of carbachol added to the bath at a 10 min interval, are obtained (the value of the second response is recorded). Responses to increasing concentrations of the test compound (0.001 to 10.0 mcg/ml with one log intervals) are then recorded every 10 min. Preparations are washed four times after each response. All doses of drugs are administered in a 0.1 ml volume. Since it has been observed that the magnitude of the second response to carbachol, which is approximately 10% greater than the first, is close to the maximal response of the tissue, such value is taken as a measure of the sensititity of the particular segment. Responses to each concentration of the test compound are expressed in terms of percentage of the second response to carbachol and the $ED_{50}$ (dose producing a response of 50% that of carbachol) is calculated graphically. Activity is scored according to the following scale:

| $ED_{50}$(mcg/ml) | Activity Value |
|---|---|
| >10 | 0 |
| 1.001-10 | 1 |
| 0.101-1.0 | 2 |
| 0.01-0.1 | 3 |
| <0.01 | 4 |

G. Evaluation of the Effects of Prostaglandin Analogs III on the Guinea Pig Trachea A male guinea pig weighing 200-500 g is killed by a blow on the head. A 20 mm length of the trachea is dissected (FIG. 1) from the animal, transferred to a petri dish containing Krebs' solution aerated with 95% $O_2$ and 5% $CO_2$ at 37° C. and cut longitudinally opposite the tracheal muscle (FIG. 2). The tissue is then cut transversely three quarters of the distance across, a second cut in the opposite procedure is continued for the whole tissue. The ends of the trachea can be pulled to form a zig-zag shaped strip (FIG. 3). The tracheal strip used in the experiment is approximately 30 mm when extended under 0.25-0.5 g load in the tissue bath. Cotton thread is tied to one end of the tissue, and linen thread to the other. It is attached via the linen thread to a glass hook in a 5 ml isolated tissue bath containing Krebs' solution at 37° C. aerated with a mixture of 95% $O_2$ and 5% $CO_2$. The opposite end is attached via cotton to an isotonic Harvard transducer[1]. The load on the transducer lever is small, usually 0.3 g, with a range of 0.25 0.5 g, and the magnification high, 80 fold using an appropriate twin-channel pen recorder. A minimum of thirty min is allowed before applying a drug to the tissue. Drugs are then applied (in volumes of 0.5 ml) at thirty min intervals, being in contact with the tissue for five min followed by an overflow washout time of twenty sec.

Prostaglandin $E_1$, at a bath concentration of 0.1 mcg/ml, is then tested repeatedly on two such strips, obtained from two different animals, until two responses (the values of which are recorded) differing by no more than 25% occur. This concentration of $PGE_1$ should elicit a relaxation expressed as from 10 to 30 mm of recorder pan excursion. A test compound is then added to the same two strips at bath concentrations of 0.01, 0.1, 1.0, and 10.0 mcg/ml and the effects of the compound are recorded. After the test compound has been evaluated at the highest concentration, $PGE_1$ is retested at 0.1 mcg/ml (and the value of the response recorded) to insure that the viability of the strips was retained during the experiment. The mean of the effects of the test compound on the two strips is then calculated for each concentration, and, based on the resulting values, a value judgement is assigned as follows:

| Response | Value Judgement |
|---|---|
| More relaxation at 0.01 mcg/ml than that elicited by PGE$_1$ | R4 |
| More relaxation at 0.1 mcg/ml than that elicited by PGE$_1$ | R3 |
| More relaxation at 1.0 mcg/ml than that elicited by PGE$_1$ | R2 |
| More relaxation at 10.0 mcg/ml that that elicited by PGE$_1$ | R1 |
| No effect at any concentration greater than that elicited by PGE$_1$ | 0 |
| More contraction at 10.0 mcg/ml than the degree of relaxation elicited by PGE$_1$ | C1 |
| More contraction at 1.0 mcg/ml that the degree of relaxation elicited by PGE$_1$ | C2 |
| More contraction at 0.1 mcg/ml than the degree of relaxation elicited by PGE$_1$ | C3 |
| More contraction at 0.01 mcg/ml than the degree of relaxation elicited by PGE$_1$ | C4 |

Table E summarizes the results of the preceeding assays utilizing preferred examples.

TABLE E

Summary of activity of Prostaglandin Analogs of Formula III in:

| Test A: | Inhibition of Human Platelet Aggregation; |
|---|---|
| Test B: | Inhibition of a Rodent Gastric Secretion; |
| Test C: | Increase in Canidae Femoral Blood Flow; |
| Test D: | Increase in Normal Feline Blood Pressure and Heart Rate; |
| Test E: | Effects on Blood Pressure in Hypertensive Rat; |
| Test F: | Effects on Rat Uterus; and |
| Test G: | Effects on Guinea Pig Trachea. |

| TR No. | EXAMPLE No. | A | B | C | D | E | F | G |
|---|---|---|---|---|---|---|---|---|
| 4569 | 23B | 2 | 4 | 0 | 0 | 0 | 0 | R3 |
| 4570 | 23A | 1 | 0 | 0 | 0 | 0 | 2 | C2 |
| 4645 | 26B | 1 | 4 | 1 | 0 | 0 | 0 | 0 |
| 4646 | 26A | 1 | 0 | 0 | 0 | 0 | 0 | C1 |
| 4673 | 25B | 1 | 3 | 0 | 0 | 1 | 0 | R3 |
| 4674 | 25A | 1 | 2 | NT | 0 | 0 | 0 | 0 |
| 4675 | 27B | 1 | 2 | 0 | 0 | NT | 0 | 0 |
| 4676 | 27A | 1 | 0 | 0 | 0 | 0 | 0 | 0 |
| 4688 | 24B | 1 | 3 | 0 | 0 | 0 | 0 | R2 |
| 4689 | 24A | 1 | 2 | 0 | 0 | NT | 0 | 0 |
| 4565 | 28A | 1 | 0 | 1 | 0 | NT | 0 | C1 |
| 4568 | 28B | 1 | 0 | 0 | 0 | 0 | 0 | 0 |
| 4626 | 29A | 1 | NT | NT | NT | NT | 0 | C1 |
| 4627 | 29B | 1 | 0 | NT | NT | NT | 0 | 0 |
| 4248 | 30A | 5 | 4 | 2 | 2 | 1 | 2 | R3 |
| 4249 | 30B | 1 | 0 | 0 | 0 | 0 | 0 | 0 |
| 4682 | 31A | 1 | 2 | 3 | 1 | 0 | 0 | 0 |
| 4681 | 31B | 2 | 4 | 2 | 1 | NT | 0 | R3 |
| 4691 | 32A | 1 | 1 | 2 | 0 | 0 | 0 | R2 |
| 4690 | 32B | 4 | 4 | 2 | 1 | 0 | 0 | R3 |
| 4677 | 33A | 1 | 3 | 0 | 0 | 0 | 3 | R1 |
| 4692 | 33B | 1 | 4 | NT | 1 | 0 | 0 | 0 |
| 4280 | 34A | 1 | 0 | NT | NT | NT | 0 | 0 |
| 4281 | 35A | 1 | 0 | NT | NT | NT | 0 | 0 |
| 4683 | 35B | 1 | 0 | NT | NT | NT | 0 | 0 |
| 4695 | 36A | 1 | 0 | NT | NT | NT | 0 | 0 |
| 4694 | 36B | 1 | 0 | NT | NT | NT | 0 | 0 |
| 4624 | 37A | 1 | 0 | 0 | 0 | 0 | 0 | 0 |
| 4625 | 37B | 1 | 0 | 0 | 0 | 0 | 0 | 0 |
| 4796 | 38A | 2 | 2 | NT | NT | NT | 0 | C3 |
| 4797 | 38B | 1 | 0 | NT | NT | NT | 0 | NT |
| 4832 | 39A | 1 | 2 | NT | NT | NT | 0 | C0 |
| 4833 | 39B | 1 | 0 | NT | NT | NT | 0 | C0 |
| 4880 | 40A | 1 | 0 | NT | NT | NT | 0 | C0 |
| 4881 | 40B | 1 | 0 | NT | NT | NT | 0 | C4 |
| 4882 | 41A | 2 | 1 | NT | NT | NT | 0 | C4 |
| 4887 | 41B | 1 | 0 | NT | NT | NT | 0 | C0 |

NT: Not tested.

What is claimed is:

1. Methyl 11α,15R-dihydroxy-16,18-methano-16-methyl-9-oxoprost-13E-en-1-oate.

2. Methyl 11α, 15R-dihydroxy-16,18-methano-20,20-propano-9-oxoprost-13E-en-1-oate.

3. Methyl 11α,15S-dihydroxy-16,18-methano-20,20-propano-9-oxoprost-13E-en-1-oate.

4. Methyl 11α,15R-dihydroxy-16,18-methano-19,20-ethano-9-oxoprost-13E-en-1-oate.

5. Methyl 11α,15S-dihydroxy-16,18-methano-19,20-ethano-9-oxoprost-13E-en-1-oate.

6. A compound having the formula:

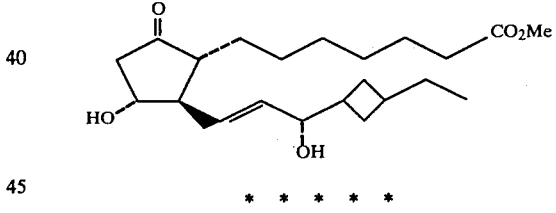

* * * * *